US012797422B2

(12) United States Patent
Hallenbeck

(10) Patent No.: US 12,797,422 B2
(45) Date of Patent: Nov. 17, 2026

(54) COMPOSITIONS AND METHODS OF USING SENECA VALLEY VIRUS (SVV) FOR TREATING CANCER

(71) Applicant: SENECA THERAPEUTICS, INC., Blue Bell, PA (US)

(72) Inventor: Paul L. Hallenbeck, Blue Bell, PA (US)

(73) Assignee: SENECA THERAPEUTICS, INC., Blue Bell, PA (US)

( * ) Notice: Subject to any disclaimer, the term of this patent is extended or adjusted under 35 U.S.C. 154(b) by 1275 days.

(21) Appl. No.: 17/601,768

(22) PCT Filed: Apr. 10, 2020

(86) PCT No.: PCT/US2020/027784
§ 371 (c)(1),
(2) Date: Oct. 6, 2021

(87) PCT Pub. No.: WO2020/210711
PCT Pub. Date: Oct. 15, 2020

(65) Prior Publication Data

US 2022/0202884 A1 Jun. 30, 2022

Related U.S. Application Data

(60) Provisional application No. 62/832,509, filed on Apr. 11, 2019.

(51) Int. Cl.
*A61K 35/76* (2015.01)
*A61K 31/167* (2006.01)
(Continued)

(52) U.S. Cl.
CPC ............ *A61K 35/76* (2013.01); *A61K 31/167* (2013.01); *A61K 31/519* (2013.01);
(Continued)

(58) Field of Classification Search
CPC ....... A61P 35/00; A61K 35/76; A61K 31/167; A61K 31/519; A61K 35/768; A61K 39/3955; A61K 45/06
See application file for complete search history.

(56) References Cited

U.S. PATENT DOCUMENTS 6,015,815 A 1/2000 Mollison
6,329,386 B1 12/2001 Mollison
(Continued)

FOREIGN PATENT DOCUMENTS

CN 1875028 A 12/2006
CN 108601802 A 9/2018
(Continued)

OTHER PUBLICATIONS

Rafferty, et al., Cell Mol Life Sci (2017) 74(14): 2525-2535 (Year: 2017).*
(Continued)

*Primary Examiner* — Evelyn Y Pyla
*Assistant Examiner* — Katherine R Small
(74) *Attorney, Agent, or Firm* — BakerHostetler

(57) ABSTRACT

Provided herein are compositions and methods of using Seneca Valley Virus (SW), or a derivative thereof, combined with an IFN-I inhibitor for treating a cancer in a subject. The disclosed methods particularly rely upon the expression level of an ANTXR1 and the expression level of IFN-I in the cancer from the subject. Also provided herein are methods for predicting the efficacy of an SW treatment and a kit for determining the same.

6 Claims, 42 Drawing Sheets

(51) Int. Cl.

| | |
|---|---|
| ***A61K 31/519*** | (2006.01) |
| ***A61K 35/768*** | (2015.01) |
| ***A61K 39/395*** | (2006.01) |
| ***A61K 45/06*** | (2006.01) |
| ***A61P 35/00*** | (2006.01) |
| *A61K 39/00* | (2006.01) |

(52) U.S. Cl.
CPC ........ *A61K 35/768* (2013.01); *A61K 39/3955* (2013.01); *A61K 45/06* (2013.01); *A61P 35/00* (2018.01); *A61K 2039/545* (2013.01)

(56) References Cited

U.S. PATENT DOCUMENTS

| | | | | |
|---|---|---|---|---|
| 7,638,318 | B2 | 12/2009 | Hallenbeck et al. | |
| 8,039,606 | B2 | 10/2011 | Hallenbeck et al. | |
| 8,753,622 | B2 | 6/2014 | Hallenbeck et al. | |
| 9,309,322 | B2 | 4/2016 | Frankel et al. | |
| 10,537,599 | B2 | 1/2020 | Miles et al. | |
| 11,096,972 | B2 | 8/2021 | Miles et al. | |
| 11,738,058 | B2 | 8/2023 | Miles et al. | |
| 2002/0123505 | A1 | 9/2002 | Mollison et al. | |
| 2003/0129215 | A1 | 7/2003 | Mollison et al. | |
| 2006/0159659 | A1 | 7/2006 | Hallenbeck | |
| 2009/0304728 | A1 | 12/2009 | Concette et al. | |
| 2010/0183633 | A1 | 7/2010 | Davis et al. | |
| 2012/0244112 | A1 | 9/2012 | Ast et al. | |
| 2012/0276125 | A1 | 11/2012 | Ast et al. | |
| 2014/0348798 | A1 | 11/2014 | Hallenbeck et al. | |
| 2019/0030099 | A1 * | 1/2019 | Miles et al. | ......... A61K 35/768 |
| 2019/0070233 | A1 | 3/2019 | Yeung et al. | |
| 2019/0358277 | A1 | 11/2019 | Yun et al. | |
| 2020/0197457 | A1 | 6/2020 | Silvestre et al. | |
| 2020/0222480 | A1 | 7/2020 | Miles et al. | |
| 2022/0054564 | A1 | 2/2022 | Miles et al. | |

FOREIGN PATENT DOCUMENTS

| | | | | |
|---|---|---|---|---|
| CN | 109022374 | A | 12/2018 | |
| CN | 111154806 | A | 5/2020 | |
| WO | WO 2005/030139 | A2 | 4/2005 | |
| WO | 2008/112891 | A2 | 9/2008 | |
| WO | WO-2014053852 | A1 * | 4/2014 | ........... A61K 35/763 |
| WO | 2014089124 | A1 | 6/2014 | |
| WO | 2017096201 | A1 | 6/2017 | |
| WO | WO 2017/143449 | A1 | 8/2017 | |
| WO | 2018049248 | A1 | 3/2018 | |
| WO | 2018234862 | A1 | 12/2018 | |
| WO | 2020037206 | A1 | 2/2020 | |
| WO | WO 2020/106843 | A1 | 5/2020 | |
| WO | WO 2020/142725 | A1 | 7/2020 | |
| WO | WO 2020/150402 | A2 | 7/2020 | |
| WO | WO 2020/210711 | A1 | 10/2020 | |
| WO | 2022150769 | A1 | 7/2022 | |
| WO | 2023107878 | A1 | 6/2023 | |

OTHER PUBLICATIONS

Rmali KA et al., 2005. Prognostic values of tumor endothelial markers in patients with colorectal cancer; World J Gastroenterol; vol. 11(9); p. 1283-1286.
Rmali KA et al., 2005. TEM-8 and tubule formation in endothelial cells, its potential role of its vW/TM domains; Biochem Biophys Res Commun; vol. 334; p. 231-238.
Rmali KA et al., 2004. Tumour endothelial marker 8 (TEM-8) in human colon cancer and its association with tumour progression; Eur J Surg Oncol; vol. 30; p. 948-953.
Ruan Z et al., 2009. DNA vaccine against tumor endothelial marker 8 inhibits tumor angiogenesis and growth; J Immunother; vol. 32 No. 5; p. 486-491.
Saleiro D et al., 2016. Mesenchymal stromal cells and Interferon alpha (IFNalpha) in cancer immunotherapy; Translational Cancer Research; vol. 5; p. S1039-S1043.
Sarbassov et al., 2004. Rictor, a Novel Binding Partner of mTOR, Defines a Rapamycin-Insensitive and Raptor-Independent Pathway that Regulates the Cytoskeleton; Current Biology; vol. 14; p. 1296-1302.
Sarbassov et al., 2005. Phosphorylation and regulation of Akt/PKB by the Rictor-mTOR Complex; Science; vol. 307; p. 1098-1101.
Shahid S et al., 2015. Mutations of the human interferon alpha-2b gene in brain tumor patients exposed to different environmental conditions; Cancer Gene Therapy; vol. 22; p. 246-261.
Shankaran V et al., 2001. IFNgamma and lymphocytes prevent primary tumour development and shape tumour immunogenicity; Nature; vol. 410; p. 1107-1111.
St Croix B et al., 2000. Genes expressed in human tumor endothelium; Science; vol. 289; p. 1197-1202.
Stojdl DF et al., 2000. Exploiting tumor-specific defects in the interferon pathway with a previously unknown oncolytic virus; Nature Medicine; vol. 6 No. 7; p. 821-825.
Stojdl DF et al., 2003. VSV strains with defects in their ability to shutdown innate immunity are potent systemic anti-cancer agents; Cancer Cell; vol. 4; p. 263-275.
Szot C et al., 2018. Tumor stroma-targeted antibody-drug conjugate triggers localized anticancer drug release; J Clin Invest; vol. 128(7); p. 2927-2943.
Van Beijnum JR et al., 2006. Gene expression of tumor angiogenesis dissected: specific targeting of colon cancer angiogenic vasculature; Blood; vol. 108 No. 7; p. 2339-2348.
Vannucci FA et al., 2015. Identification and Complete Genome of Seneca Valley Virus in Vesicular Fluid and Sera of Pigs Affected with Idiopathic Vesicular Disease, Brazil; Transboundary and Emerging Diseases; vol. 62; p. 589-93.
Venanzi FM et al., 2010. Tumor endothelial marker 8 expression levels in dendritic cell-based cancer vaccines are related to clinical outcome; Cancer Immunol Immunother; vol. 59; p. 27-34.
Verma K et al., 2011. Tumor endothelial marker 8 amplifies canonical Wnt signaling in blood vessels; PLoS One; vol. 6 e22334; 9 pages.
Wadhwa L et al., 2007. Treatment of invasive retinoblastoma in a murine model using an oncolytic picornavirus; Cancer Res; vol. 67; p. 10653-10656.
Werner E et al., 2006. Anthrax toxin receptor 1/tumor endothelium marker 8 mediates cell spreading by coupling extracellular ligands to the actin cytoskeleton; The Journal of Biological Chemistry; vol. 281 No. 32; p. 23227-23236.
Wollmann G et al., 2007. Variable deficiencies in the interferon response enhance susceptibility to vesicular stomatitis virus oncolytic actions in glioblastoma cells but not in normal human glial cells; Journal of Virology; vol. 81 No. 3; p. 1479-1491.
Wong LH et al., 1997. Interferon-resistant human melanoma cells are deficient in ISGF3 components, STAT1, STAT2, and p48-ISGF3y; The Journal of Biological Chemistry; vol. 272 No. 45; 28779-28785.
Wu Q et al., 2016. Complete Genome Sequence of Seneca Valley Virus CH-01-2015 Identified in China; Genome Announcements; vol. 4 Issue 1; one page.
Yang MY et al., 2011. The cell surface structure of tumor endothelial marker 8 (TEM8) is regulated by the actin cytoskeleton; Biochimica Biophysica Acta; vol. 1813; p. 39-49.
Yang X et al., 2010. Dendritic cells transduced with TEM8 recombinant adenovirus prevents hepatocellular carcinoma angiogenesis and inhibits cells growth; Vaccine; vol. 28; p. 7130-7135.
Yu L et al., 2011. A single intravenous injection of oncolytic picornavirus SVV-001 eliminates medulloblastomas in primary tumor-based orthotopic xenograft mouse models; Neuro-Oncology; vol. 13; p. 14-27.
Zhang J et al., 2015. Full-Length Genome Sequences of Senecavirus A from Recent Idiopathic Vesicular Disease Outbreaks in U.S. Swine; Genome Announcement; vol. 3 Issue 6; 2 pages.
International Patent Application No. PCT/US2020/42795; Int'; Search Report and the Written Opinion; dated Oct. 28, 2020; 11 pages.
Das et al.; "Interferon-Inducible Protein IFI35 Negatively Regulates RIG-I Antiviral Signaling and Supports Vesicular Stomatitis Virus"; Journal of Virology; vol. 88 No. 6; Mar. 2014; p. 3103-3113.

(56) References Cited

OTHER PUBLICATIONS

Nguyen et al.; "Chemical targeting of the innate antiviral response by histone deacetylase inhibitors renders refractory cancers sensitive to viral oncolysis"; PNAS; vol. 105 No. 39; Sep. 2008; p. 14981-14986.
Kubo et al.; "Janus Kinase Inhibitor Baricitinib Modulates Human Innate and Adaptive Immune System"; Frontier in Immunology; vol. 9 Article 1510; Jun. 2018; 11 pages.
International Patent Application No. PCT/US2020/027784; Int'l Search Report and the Written Opinion; dated Jul. 9, 2020; 18 pages.
Isella et al.; "Stromal contribution to the colorectal cancer transcriptome"; Nature Genetics; vol. 47 No. 4; Apr. 2015; p. 312-319.
Morton et al.; "Initial Testing of the Replication Competent Seneca Valley Virus (NXT-010) by the Pediatric Preclinical Testing Program"; Pediatr Blood Cancer; vol. 55; 2010; p. 295-303.
Croft et al.; "The Reactome pathway knowledgebase"; Nucleic Acids Research; vol. 42; 2014; p. D472-D477.
European Patent Application No. 16871597.7; Extended Search Report; dated Jul. 1, 2019; 2 pages.
"GeneChip Human Genome Arrays"; Affymetrix Data Sheet; Jan. 2003; 4 pages.
Gunturi et al.; "Nivolumab for the treatment of cancer; Expert Opinion on Investigational Drugs"; vol. 24(2); 2015; p. 253-260.
Mindell et al.; "Accurate determination of local defocus and specimen tilt in electron microscopy"; Journal of Structural Biology; vol. 142; 2003; p. 334-347.
Carette et al.; "Ebola virus entry requires the cholesterol transporter Niemann-Pick C1"; Nature; vol. 477; Sep. 2011; p. 340-343.
Poirier et al.; "Selective Tropism of Seneca Valley Virus for Variant Subtype Small Cell Lung Cancer"; JNCI Brief Communications; vol. 105 Issue 14; Jul. 2013; p. 1059-1065.
Bradley et al.; "Identification of the cellular receptor for anthrax toxin"; Nature; vol. 414; Nov. 2001; 4 pages.
Organtini et al.; "Kinetic and Structural Analysis of Coxsackievirus B3 Receptor Interactions and Formation of the A-Particle"; Journal of Virology; vol. 88 No. 10; May 2014; p. 5755-5765.
Lynch et al.; "Ipilimumab in Combination With Paclitaxel and Carboplatin As First-Line Treatment in Stage IIIB/IV Non-Small-Cell Lung Cancer: Results from a Randomized, Double-Blind, Multicenter Phase II Study"; Journal of Clinical Oncology; vol. 30 No. 17; Jun. 2012; p. 2046-2054.
Milacic et al.; "Annotating Cancer Variants and Anti-Cancer Therapeutics in Reactome"; Cancer; vol. 4; 2012; p. 1180-1211.
Strauss et al.; "Nectin-Like Interactions between Poliovirus and Its Receptor Trigger Conformational Changes Associated with Cell Entry"; Journal of Virology; vol. 89 No. 8; Apr. 2015; p. 4143-4157.
McDermott et al.; "Pembrolizumab: PD-1 Inhibition as a Therapeutic Strategy in Cancer"; Drugs Today; vol. 51(1); Jan. 2015; p. 7-20.
Vargas et al.; "Broad Expression Analysis of Human ANTXR1/TM8 Transcripts Reveals Differential Expression and Novel Splizce Variants"; PLOS One; vol. 7 Issue 8; Aug. 2012; 14 pages.
European Patent Application No. 20787585.7; Extended Search Report; dated Dec. 9, 2022; 11 pages.
Liu et al.; "Intravenous injection of oncolytic picornavirus SVV-001 prolongs animal survival in a panel or primary tumor-based orthotopic xenograft mouse models of pediatric glioma"; Neuro-Oncology; vol. 15(9); 2013; p. 1173-1185.
Zhang et al.; "Review of Seneca Valley Virus: A Call for Increased Surveillance and Research"; Frontiers in Microbiology; vol. 9; May 2018; 8 pages.
[HG-U133_Plus_2] Affymetrix Human Genome U133 Plus 2.0 Array; https://www.ncbi.nlm.nih.gov/geo/query/acc.cgi?acc=GPL570; Nov. 2003; accessed Mar. 2, 2023; 4 pages.
Bachran C. et al., 2016. Tumor Targeting and Drug Delivery by Anthrax Toxin; Toxins; vol. 8; 16 pages.
Balachandran S. et al., 2001. Oncolytic activity of vesicular stomatitis virus is effective against tumors exhibiting aberrant p53, Ras, or myc function and involves the induction of apoptosis; Journal of Virology; vol. 75 No. 7; p. 3474-3479.
Beevers et al. 2006, Curcumin inhibits the mammalian target of rapamycin-mediated Signaling Pathways in cancer cells, Int. J. Cancer; vol. 119(4); p. 757-764.
Besschetnova TY et al., 2015. Regulatory mechanisms of anthrax toxin receptor 1-dependent vascular and connective tissue homeostasis; Matrix Biology; vol. 42; p. 56-73.
Bonuccelli G et al., 2005. ATR/TEM8 is highly expressed in epithelial cells lining Bacillus anthracis' three sites of entry: implications for the pathogenesis of anthrax infection; Am J Physiol Cell Physiol; vol. 288; p. C1402-C1410.
Bradley KA, et al., 2001. Identification of the cellular receptor for anthrax toxin; Nature; vol. 414; p. 225-229.
Burke MJ, et al., 2015. Phase I trial of Seneca Valley Virus (NTX-010) in children with relapsed/refractory solid tumors: a report of the Children's Oncology Group; Pediatr Blood Cancer; vol. 62(5); p. 743-750.
Burke MJ. 2016. Oncolytic Seneca Valley Virus: past perspectives and future directions; Oncolytic Virotherapy; vol. 5; p. 81-89.
Byrd TT, et al., 2018. TEM8/ANTXR1-Specific CAR T Cells as a Targeted Therapy for Triple-Negative Breast Cancer; Cancer Research; vol. 78; p. 489-500.
Carson-Walter EB, et al., 2001. Cell surface tumor endothelial markers are conserved in mice and humans; Cancer Research; vol. 61; p. 6649-6655.
"Leading Causes of Death—Males—All races and origins", Mar. 2022; Centers for Disease Control and Prevention; cdc.gov/healthequity/lcod/men/2018/all-races-origins/index.htm; 5 pages.
Chandra et al., HCV Infection Selectively Impairs Type 1 but Not Type III IFN Signaling, The Amercian Journal of Pathology, Jan. 2014, vol. 184, No. 1, pp. 214-229.
Chang HM et al., 2004. Induction of interferon-stimulated gene expression and antiviral responses require protein deacetylase activity; Proc Natl Acad Science; vol. 101 No. 26; p. 9578-9583.
Chaudhary A et al., 2012. TEM8/ANTXR1 blockade inhibits pathological angiogenesis and potentiates tumoricidal responses against multiple cancer types; Cancer Cell; vol. 21; p. 212-226.
Chen D et al., 2013. ANTXR1, a stem cell-enriched functional biomarker, connects collagen signaling to cancer stem-like cells and metastasis in breast cancer; Cancer Res; vol. 73; p. 5821-5833.
Colamonici OR et al., 1992. Correlation between interferon (IFN) alpha resistance and deletion of the IFN alpha/beta genes in acute leukemia cell lines suggests selection against the IFN system; Blood; vol. 80 No. 3; p. 744-749.
Colina R et al., 2008. Translational control of the innate immune response through IRF-7; Nature; vol. 452; 31 pages.
Cryan LM et al., 2011. Targeting the anthrax receptors, TEM-8 and CMG-2, for anti-angiogenic therapy; Frontiers in Bioscience; vol. 16; p. 1574-1588.
Cullen M et al., 2009. Host-derived tumor endothelial marker 8 promotes the growth of melanoma; Cancer Res; vol. 69; p. 6021-6026.
Davies G et al., 2004. Levels of expression of endothelial markers specific to tumour-associated endothelial cells and their correlation with prognosis in patients with breast cancer; Clinical & Experimental Metastasis; vol. 21; p. 31-37.
Dold C et al., 2016. Application of interferon modulators to overcome partial resistance of human ovarian cancers to VSV-GP oncolytic viral therapy; Molecular Therapeutics—Oncolytics; vol. 3; 11 pages.
Duan HF et al., 2007. Antitumor activities of TEM8-Fc: an engineered antibody-like molecule targeting tumor endothelial marker 8; J Natl Cancer Inst; vol. 99; p. 1551-1555.
Felicetti P et al., 2007. Tumor endothelial marker 8 enhances tumor immunity in conjunction with immunization against differentiation Ag; Cytotherapy; vol. 9 No. 1; p. 23-34.
Fernando S et al., 2009. Targeting tumor endothelial marker 8 in the tumor vasculature of colorectal carcinomas in mice; Cancer Res; vol. 69; p. 5126-5132.
Genin P et al., 2003. Impairment of interferon-induced IRF-7 gene expression due to inhibition of ISGF3 formation by Trichostatin A; Journal of Virology; vol. 77; p. 7113-7119.

(56) References Cited

OTHER PUBLICATIONS

Gu J et al., 2010. Endosomal recycling regulates Anthrax Toxin Receptor 1/Tumor Endothelial Marker 8-dependent cell spreading; Exp Cell Res; vol. 316(12); p. 1946-1957.
Guo B et al., 2016. Novel Senecavirus A in Swine with Vesicular Disease, United States, Jul. 2015; Emerging Infectious Diseases; vol. 22 No. 7; p. 1325-1327.
Hales LM et al., 2008. Complete genome sequence analysis of Seneca Valley virus-001, a novel oncolytic picornavirus; Journal of General Virology; vol. 89; p. 1265-1275.
Halsall JA et al., 2016. Histone deacetylase inhibitors for cancer therapy: An evolutionarily ancient resistance response may explain their limited success; Bioessays; vol. 38; p. 1102-1110.
Hanahan D et al., 2011. Hallmarks of cancer: the next generation; Cell; vol. 144; p. 646-674.
Hotchkiss KA et al., 2005. TEM8 expression stimulates endothelial cell adhesion and migration by regulating cell-matrix interactions on collagen; Exp Cell Res; vol. 305; p. 133-144.
Ida-Hosonuma M et al., 2005. The alpha/beta interferon response controls tissue tropism and pathogenicity of poliovirus; Journal of Virology; vol. 79; p. 4460-4469.
Ida-Hosonuma M et al., 2003. Host range of poliovirus is restricted to simians because of a rapid sequence change of the poliovirus receptor gene during evolution; Arch Virol; vol. 148; p. 29-44.
Joseph J et al., 2004. Expression profiling of sodium butyrate (NaB)-treated cells: identification of regulation of genes related to cytokine signaling and cancer metastasis by NaB; Oncogene; vol. 23; p. 6304-6315.
Katsoulidis E et al., 2010. Deregulation of Interferon Signaling in Malignant Cells; Pharmaceuticals; vol. 3; p. 406-418.
Kaur S et al., 2007. Regulatory effects of mammalian target of rapamycin-activated pathways in type I and II interferon signaling; The Journal of Biological Chemistry; vol. 282 No. 3; p. 1757-1768.
Kelly WK et al., 2005. Drug insight: Histone deacetylase inhibitors—development of the new targeted anticancer agent suberoylanilide hydroxamic acid; Nature Clinical Practice Oncology; vol. 2; p. 150-157.
Kotredes KP et al., 2013. Interferons as inducers of apoptosis in malignant cells; Journal of Interferon & Cytokine Research; vol. 33 No. 4; p. 162-170.
Lamborn IT et al., 2017. Recurrent rhinovirus infections in a child with inherited MDA5 deficiency; J Exp Med; vol. 214 No. 7; p. 1949-1972.
Leme RA et al., 2015. Senecavirus A: An Emerging Vesicular Infection in Brazilian Pig Herds; Transboundary Emerging Diseases; vol. 62; p. 603-611.
Liu S et al., 2003. Cell surface tumor endothelium marker 8 cytoplasmic tail-independent anthrax toxin binding, proteolytic processing, oligomer formation, and internalization; The Journal of Biological Chemistry; vol. 278 No. 7; p. 5227-5234.
McMahon et al., 2005. Farnesylthiosalicylic Acid Inhibits Mammalian Target of Rapamycin (mTOR) Activity Both in Cells and in Vitro by Promoting Dissociation of the mTORRaptor Complex; Molecular Endocrinology; vol. 19(1); p. 175-183.
Mehnert JM et al., 2007. Histone deacetylase inhibitors: biology and mechanism of action; The Cancer Journal; vol. 13 No. 1; p. 23-29.
Miles LA et al., 2017. Anthrax toxin receptor 1 is the cellular receptor for Seneca Valley virus. J Clin Invest.; vol. 127; p. 2957-2967.
Minucci S et al., 2006. Histone deacetylase inhibitors and the promise of epigenetic (and more) treatments for cancer. Nature Reviews Cancer; vol. 6; p. 38-51.
Morton CL et al., 2010. Initial testing of the replication competent Seneca Valley virus (NTX-010) by the pediatric preclinical testing program; Pediatr Blood Cancer; vol. 55(2); p. 295-303.
Joseph et al, 2004. Expression profiling of sodium butyrate (NaB)-treated cells: identification of regulation of genes related to cytokine signaling and cancer metastasis by NaB; Oncogene; vol. 23; 12 pages.
Nanda A et al., 2004. TEM8 interacts with the cleaved C5 domain of collagen alpha 3(VI); Cancer Research; vol. 64; p. 817-820.
Nusinzon I et al., 2006. Positive and negative regulation of the innate antiviral response and beta interferon gene expression by deacetylation; Molecular and Cellular Biology; vol. 26; p. 3106-3113.
Pang L et al., 2014. A polymorphism in melanoma differentiation-associated gene 5 may be a risk factor for enterovirus 71 infection; Clin Microbiol Infect; vol. 20; p. 0711-0717.
International Patent Application No. PCT/US2022/011994; Int'l Search Report and the Written Opinion; dated Jun. 8, 2022; 15 pages.
International Patent Application No. PCT/US2022/011994; Int'l Preliminary Report on Patentability; dated Jul. 20, 2023; 8 pages.
Chen et al.; "Construction and characterization of a full-length cDNA infectious clone of emerging porcine Senecavirus A"; Virology; vol. 497; 2016; p. 111-124.
International Patent Application No. PCT/US2022/13001; Int'l Search Report and the Written Opinion; dated Jun. 8, 2022; 20 pages.
International Patent Application No. PCT/US2022/13001; Int'l Preliminary Report on Patentability; dated Aug. 3, 2023; 14 pages.
European Patent Application No. 20843259.1; Extended Search Report; dated Jul. 21, 2023; 8 pages.
Jayawardena et al.; "Structural basis for anthrax toxin receptor 1 recognition by Seneca Valley Virus"; PNAS; vol. 115 No. 46; Oct. 2018; p. E10934-E10940.
Kolatkar et al.; "Structural studies of two rhinovirus serotypes complexed with fragments of their cellular receptor"; The EMBO Journal; vol. 18 No. 22; 1999; p. 6429-6259.
"QuantiFERON-TB Gold (QFT) ELISA Package Insert"; Qiagen; Aug. 2016; 36 pages.
Tuthill et al.; "Picornaviruses"; Current Topics in Microbiology and Immunology; vol. 343; 2010; p. 43-89.
Wu et al.; "Camera: a competitive gene set test accounting for inter-gene correlation"; Nucleic Acids Research; vol. 40 No. 17; 2012; 12 pages.
Pettersen et al.; "UCSF Chimera—A Visualization System for Exploratory Research and Analysis"; Journal of Computational Chemistry; vol. 25; 2004; p. 1605-1612.
Neale et al.; "Molecular Characterization of the Pediatric Preclinical Testing Panel"; Clinical Cancer Research; vol. 14(14); Jul. 2008; p. 4572-4583.
Tang et al.; "EMAN2: An extensible image processing suite for electron microscopy"; Journal of Structural Biology; vol. 157; 2007; p. 38-46.
Barretina et al.; "The Cancer Cell Line Encyclopedia enables predictive modelling of anticancer drug sensitivity"; Nature; vol. 483; Mar. 2012; p. 603-607.
Poirier et al.; "Characterization of a full-length infectious cDNA clone and a GFP reporter derivative of the oncolytic picornavirus SVV-001"; Journal of General Virology; vol. 93; 2012; p. 2606-2613.
Cong et al.; "Multiplex Genome Engineering Using CRISPR/Cas Systems"; Science; vol. 339; Feb. 2013; p. 819-823.
Hansson et al.; "PCR-mediated deletion of plasmid DNA"; Analytical Biochemistry; vol. 375; 2008; p. 373-375.
Jinek et al.; "A Programmable Dual-RNA-Guided DNA Endonuclease in Adaptive Bacterial Immunity"; Science; vol. 337; Aug. 2012; p. 816-821.
Zilliox et al. "A gene expression bar code for microarray data"; Nature Methods; vol. 4 No. 11; Nov. 2007; p. 911-913.
Sanjana et al.; "Improved vectors and genome-wide libraries for CRISPR screening"; Nature Methods; vol. 11 No. 8; Aug. 2014; p. 783-784.
Shalem et al.; "Genome-Scale CRISPR-Cas9 Knockout Screening in Human Cells"; Science; vol. 343; Jan. 2014; p. 84-87.
Mali et al.; "RNA-Guided Human Genome Engineering via Cas9"; Science; vol. 339; Feb. 2013; p. 823-826.
Reddy et al.; "Seneca Valley Virus, a Systemically Deliverable Oncolytic Picornavirus, and the Treatment of Neuroendocrine Cancers"; J Nat'l Cancer Inst; vol. 99; 2007; p. 1623-1633.

(56) References Cited

OTHER PUBLICATIONS

Hanzelmann et al.; "GSVA: gene set variation analysis for microarray and RNA-Seq data"; BMC Bioinformatics; vol. 14(7); 2013; 15 pages.
Scheres; "RELION: Implementation of a Byesian approach to cryo-EM structure determination"; Journal of Structural Biology; vol. 180; 2012; p. 519-530.
Venkataraman et al.; "Structure of Seneca Valley Virus-001: An Oncolytic Picornavirus Representing a New Genus"; Structure; vol. 16; Oct. 2008; p. 1555-1561.
International Patent Application No. PCT/US2016/64679; Int'l Search Report and the Written Opinion; dated Feb. 7, 2017; 11 pages.
Melonie Heron; "Deaths: Leading Causes for 2016"; National Vital Statistics Reports; vol. 67 No. 6; Jul. 2018; 77 pages.
International Patent Application No. PCT/US2020/042795; Int'l Preliminary Report on Patentability; dated Feb. 3, 2022; 9 pages.
Alain et al., Vesicular stomatitis virus oncolysis is ptentiated by impariring mTORC1-dependent type I IFN production, PNAS, 107(4):1576-1581, 2010. www.pnas.org/cgi/doi/10.1073/pnas.0912344107.
Guo, Oncolytic immunotherapy for metastatic cancer: lessons and future strategies, Annals of Translational Medicine, 8(17): 1113, 2020. doi: 10.21037/atm.2020.04.42.
Hagberg et al., IFN-α Production by Plasmacytoid Dendritic Cells Stimulated with RNA-Containing Immune Complexes Is Promoted by NK Cells via MIP-1β and LFA-1, The Journal of Immunology, 186(9): 5085-5094, 2011. https://doi.org/10.4049/jimmunol.1003349.
LOVGREN et at., Induction of interferon-α production in plasmacytoid dendritic cells by immune complexes containing nucleic acid released by necrotic or late apoptotic cells and lupus IgG, Arthritis & Rheumatology, 50(6): 1861-1872, 2004. https://doi.org/10.1002/art.20254.
Mendoza et al., Review of dimethyl fumarate (Tecfidera) Part 1: Mechanism of action and efficacy formultiple sclerosis patients, Clinical Practice and New Drugs, 54: 873-882, 2017.
Moerdyk-Schauwecker et al., Resistance of pancreatic cancer cells to oncolytic vesicular stomatitis virus: role of type I interferon signaling, Virology, 436(1): 221-234, 2013. doi: 10.1016/j.virol.2012.11.014.
Notification of Transmittal of the International Search Report and the Written Opinion of the International Searching Authority for International Application No. PCT/US2023/073767, mailed Jan. 18, 2024, 13 pages.
Qian et al., Seneca Valley Virus Suppresses Host Type I Interferon Production by Targeting Adaptor Proteins MAVS, TRIF and TANK for Cleavage, J. Virol., 91(16):e00823-17, 2017. doi: 10.1128/JVI.00823-17.
Cao et al., Toll-like receptor-mediated induction of type 1 interferon in plasmacytoid dendritic cells requires the rapamycin-sensitive PI(3)K-mTOR-p7OS6K pathway, Nature Immunology, 9(10): 1157-1164, Oct. 2008.
Liu et al., Construction of eGFP-Tagged Senecavirus A for Facilitating Virus Neutralization Test and Antiviral Assay, Viruses, 12(283): 18 pages, 2020.
Rudin et al., Phase 1 Clinical Study of Seneca Valley Virus (SVV-001 ), a Replication-Competent Picornavirus, in Advanced Solid Tumors with Neuroendocrine Features, Clinical Cancer Research 17(4): 888-895, Feb. 15, 2011.

* cited by examiner

TO FIG. 9B

FROM FIG. 9A

TO FIG. 9C

FROM FIG. 9B

| Cell Line Name | Primary site | Histology | IFN | ANTXR1 | Predictor |
|---|---|---|---|---|---|
| A101D | skin | malignant_melanoma | NP | P | NP |
| A1207 | central_nervous_system | glioma | NP | P | NP |
| A172 | central_nervous_system | glioma | NP | P | NP |
| A204 | soft_tissue | rhabdoid_tumour | NP | P | NP |
| A2058 | skin | malignant_melanoma | NP | P | NP |
| A253 | salivary_gland | carcinoma | NP | P | NP |
| A2780 | ovary | carcinoma | NP | P | NP |
| A673 | bone | Ewings_sarcoma | NP | P | NP |
| A704 | kidney | carcinoma | NP | NP | NP |
| ABC1 | lung | carcinoma | P | P | P |
| ACCMESO1 | pleura | mesothelioma | NP | P | NP |
| AGS | stomach | carcinoma | NP | NP | NP |
| ALLSIL | haematopoietic_and_lymphoid_tissue | lymphoid_neoplasm | NP | P | NP |
| AM38 | central_nervous_system | glioma | NP | P | NP |
| AML193 | haematopoietic_and_lymphoid_tissue | haematopoietic_neoplasm | NP | NP | NP |
| AMO1 | haematopoietic_and_lymphoid_tissue | lymphoid_neoplasm | NP | NP | NP |
| AU565 | breast | carcinoma | NP | NP | NP |
| AZ521 | stomach | carcinoma | NP | NP | NP |
| BC3C | urinary_tract | carcinoma | NP | P | NP |
| BCP1 | haematopoietic_and_lymphoid_tissue | lymphoid_neoplasm | NP | NP | NP |
| BCPAP | thyroid | carcinoma | NP | P | NP |
| BDCM | haematopoietic_and_lymphoid_tissue | lymphoid_neoplasm | NP | NP | NP |
| BEN | lung | carcinoma | NP | NP | NP |
| BFTC905 | urinary_tract | carcinoma | NP | P | NP |
| BFTC909 | kidney | carcinoma | NP | P | NP |
| BHT101 | thyroid | carcinoma | NP | P | NP |
| BHY | upper_aerodigestive_tract | carcinoma | NP | P | NP |
| BL41 | haematopoietic_and_lymphoid_tissue | lymphoid_neoplasm | NP | NP | NP |
| BL70 | haematopoietic_and_lymphoid_tissue | lymphoid_neoplasm | NP | NP | NP |
| BT20 | breast | carcinoma | NP | P | NP |
| BT474 | breast | carcinoma | NP | P | NP |
| BT483 | breast | carcinoma | NP | NP | NP |
| BV173 | haematopoietic_and_lymphoid_tissue | haematopoietic_neoplasm | NP | NP | NP |
| C32 | skin | malignant_melanoma | NP | P | NP |
| C3A | liver | carcinoma | NP | P | NP |
| CA46 | haematopoietic_and_lymphoid_tissue | lymphoid_neoplasm | NP | NP | NP |

FIG. 19

| Cell Line Name | Primary site | Histology | IFN | ANTXR1 | Predictor |
|---|---|---|---|---|---|
| CADOES1 | bone | Ewings_sarcoma | P | P | P |
| CAL120 | breast | carcinoma | NP | P | NP |
| CAL12T | lung | carcinoma | NP | P | NP |
| CAL148 | breast | carcinoma | P | NP | NP |
| CAL29 | urinary_tract | carcinoma | NP | P | NP |
| CAL33 | upper_aerodigestive_tract | carcinoma | NP | NP | NP |
| CAL51 | breast | carcinoma | P | P | P |
| CAL54 | kidney | carcinoma | NP | P | NP |
| CAL62 | thyroid | carcinoma | NP | P | NP |
| CAL78 | bone | chondrosarcoma | NP | P | NP |
| CAL851 | breast | carcinoma | NP | P | NP |
| CAMA1 | breast | carcinoma | NP | P | NP |
| CAS1 | central_nervous_system | glioma | NP | P | NP |
| CCFSTTG1 | central_nervous_system | glioma | NP | P | NP |
| CCK81 | large_intestine | carcinoma | NP | NP | NP |
| CFPAC1 | pancreas | carcinoma | NP | NP | NP |
| CGTHW1 | thyroid | carcinoma | NP | P | NP |
| CH157MN | central_nervous_system | meningioma | NP | P | NP |
| CHL1 | skin | malignant_melanoma | NP | P | NP |
| CHP126 | autonomic_ganglia | neuroblastoma | P | P | P |
| CHP212 | autonomic_ganglia | neuroblastoma | NP | P | NP |
| CI1 | haematopoietic_and_lymphoid_tissue | lymphoid_neoplasm | NP | NP | NP |
| CJM | skin | malignant_melanoma | NP | P | NP |
| CL11 | large_intestine | carcinoma | NP | NP | NP |
| CL14 | large_intestine | carcinoma | NP | NP | NP |
| CL34 | large_intestine | carcinoma | NP | NP | NP |
| CL40 | large_intestine | carcinoma | NP | NP | NP |
| CMK115 | haematopoietic_and_lymphoid_tissue | haematopoietic_neoplasm | NP | NP | NP |
| CMK86 | haematopoietic_and_lymphoid_tissue | haematopoietic_neoplasm | NP | NP | NP |
| CMK | haematopoietic_and_lymphoid_tissue | haematopoietic_neoplasm | NP | NP | NP |
| CMLT1 | haematopoietic_and_lymphoid_tissue | haematopoietic_neoplasm | NP | P | NP |
| COLO320 | large_intestine | carcinoma | NP | P | NP |
| COLO677 | haematopoietic_and_lymphoid_tissue | lymphoid_neoplasm | NP | NP | NP |
| COLO678 | large_intestine | carcinoma | NP | NP | NP |
| COLO679 | skin | malignant_melanoma | NP | NP | NP |
| COLO680N | oesophagus | carcinoma | NP | P | NP |

FIG. 19 (cont.)

| Cell Line Name | Primary_site | Histology | IFN | ANTXR1 | Predictor |
|---|---|---|---|---|---|
| COLO704 | ovary | carcinoma | P | P | P |
| COLO783 | skin | malignant_melanoma | NP | P | NP |
| COLO800 | skin | malignant_melanoma | NP | P | NP |
| COLO818 | skin | malignant_melanoma | NP | P | NP |
| COLO849 | skin | malignant_melanoma | NP | P | NP |
| CORL105 | lung | carcinoma | NP | P | NP |
| CORL23 | lung | carcinoma | NP | NP | NP |
| CORL24 | lung | carcinoma | P | P | P |
| CORL279 | lung | carcinoma | P | NP | NP |
| CORL311 | lung | carcinoma | P | NP | NP |
| CORL47 | lung | carcinoma | NP | NP | NP |
| CORL51 | lung | carcinoma | P | NP | NP |
| CORL88 | lung | carcinoma | P | NP | NP |
| CORL95 | lung | carcinoma | NP | P | NP |
| COV318 | ovary | carcinoma | NP | P | NP |
| COV362 | ovary | carcinoma | NP | P | NP |
| COV434 | ovary | sex_cord-stromal_tumour | NP | NP | NP |
| COV504 | ovary | carcinoma | NP | P | NP |
| COV644 | ovary | carcinoma | NP | P | NP |
| CPCN | lung | carcinoma | NP | NP | NP |
| CW2 | large_intestine | carcinoma | NP | NP | NP |
| DANG | pancreas | carcinoma | NP | P | NP |
| DB | haematopoietic_and_lymphoid_tissue | lymphoid_neoplasm | NP | NP | NP |
| DBTRG05MG | central_nervous_system | glioma | NP | P | NP |
| DEL | haematopoietic_and_lymphoid_tissue | lymphoid_neoplasm | NP | NP | NP |
| DFCI024 | lung | carcinoma | NP | P | NP |
| DKMG | central_nervous_system | glioma | NP | P | NP |
| DLD1 | large_intestine | carcinoma | NP | NP | NP |
| DM3 | pleura | mesothelioma | NP | P | NP |
| DND41 | haematopoietic_and_lymphoid_tissue | lymphoid_neoplasm | NP | P | NP |
| DOHH2 | haematopoietic_and_lymphoid_tissue | lymphoid_neoplasm | NP | NP | NP |
| DU4475 | breast | carcinoma | P | NP | NP |
| DV90 | lung | carcinoma | NP | NP | NP |
| EB1 | haematopoietic_and_lymphoid_tissue | lymphoid_neoplasm | NP | NP | NP |
| EB2 | haematopoietic_and_lymphoid_tissue | lymphoid_neoplasm | NP | NP | NP |
| EBC1 | lung | carcinoma | NP | P | NP |

FIG. 19 (cont.)

| Cell Line Name | Primary site | Histology | IFN | ANTXR1 | Predictor |
|---|---|---|---|---|---|
| ECC10 | stomach | carcinoma | P | NP | NP |
| ECC12 | stomach | carcinoma | NP | NP | NP |
| ECGI10 | oesophagus | carcinoma | NP | P | NP |
| EFE184 | endometrium | carcinoma | NP | P | NP |
| EFM192A | breast | carcinoma | NP | NP | NP |
| EFM19 | breast | carcinoma | NP | P | NP |
| EFO21 | ovary | carcinoma | NP | P | NP |
| EFO27 | ovary | carcinoma | NP | P | NP |
| EHEB | haematopoietic_and_lymphoid_tissue | lymphoid_neoplasm | NP | NP | NP |
| EJM | haematopoietic_and_lymphoid_tissue | lymphoid_neoplasm | NP | NP | NP |
| EM2 | haematopoietic_and_lymphoid_tissue | haematopoietic_neoplasm | NP | NP | NP |
| EN | endometrium | carcinoma | P | P | P |
| EOL1 | haematopoietic_and_lymphoid_tissue | haematopoietic_neoplasm | NP | NP | NP |
| EPLC272H | lung | carcinoma | NP | P | NP |
| ES2 | ovary | carcinoma | NP | P | NP |
| ESS1 | endometrium | carcinoma | NP | P | NP |
| EVSAT | breast | carcinoma | P | NP | NP |
| EW8 | bone | Ewings_sarcoma | NP | P | NP |
| EWS502 | bone | Ewings_sarcoma | P | P | P |
| F36P | haematopoietic_and_lymphoid_tissue | haematopoietic_neoplasm | NP | NP | NP |
| F5 | central_nervous_system | meningioma | NP | P | NP |
| FTC133 | thyroid | carcinoma | NP | P | NP |
| FTC238 | thyroid | carcinoma | NP | P | NP |
| FU97 | stomach | carcinoma | NP | NP | NP |
| FUOV1 | ovary | carcinoma | NP | P | NP |
| G361 | skin | malignant_melanoma | NP | P | NP |
| G401 | soft_tissue | rhabdoid_tumour | NP | P | NP |
| G402 | soft_tissue | rhabdoid_tumour | NP | NP | NP |
| GA10 | haematopoietic_and_lymphoid_tissue | lymphoid_neoplasm | NP | NP | NP |
| GAMG | central_nervous_system | glioma | NP | P | NP |
| GB1 | central_nervous_system | glioma | NP | P | NP |
| GCIY | stomach | carcinoma | NP | P | NP |
| GCT | soft_tissue | malignant_fibrous_sarcoma | NP | P | NP |
| GDM1 | haematopoietic_and_lymphoid_tissue | haematopoietic_neoplasm | NP | NP | NP |
| GI1 | central_nervous_system | glioma | NP | P | NP |
| GMS10 | central_nervous_system | glioma | NP | P | NP |

FIG. 19 (cont.)

| Cell Line Name | Primary site | Histology | IFN | ANTXR1 | Predictor |
|---|---|---|---|---|---|
| GOS3 | central_nervous_system | glioma | NP | P | NP |
| GRANTA519 | haematopoietic_and_lymphoid_tissue | lymphoid_neoplasm | NP | NP | NP |
| GRM | skin | malignant_melanoma | NP | P | NP |
| GSS | stomach | carcinoma | NP | NP | NP |
| GSU | stomach | carcinoma | NP | NP | NP |
| H4 | central_nervous_system | glioma | NP | P | NP |
| HARA | lung | carcinoma | NP | P | NP |
| HCC1143 | breast | carcinoma | NP | P | NP |
| HCC1171 | lung | carcinoma | NP | P | NP |
| HCC1187 | breast | carcinoma | NP | P | NP |
| HCC1195 | lung | carcinoma | NP | P | NP |
| HCC1359 | lung | carcinoma | NP | P | NP |
| HCC1395 | breast | carcinoma | NP | P | NP |
| HCC1419 | breast | carcinoma | NP | NP | NP |
| HCC1428 | breast | carcinoma | NP | NP | NP |
| HCC1438 | lung | carcinoma | NP | P | NP |
| HCC1500 | breast | carcinoma | NP | NP | NP |
| HCC1569 | breast | carcinoma | NP | P | NP |
| HCC1588 | lung | carcinoma | NP | NP | NP |
| HCC1599 | breast | carcinoma | NP | P | NP |
| HCC15 | lung | carcinoma | NP | P | NP |
| HCC1806 | breast | carcinoma | NP | P | NP |
| HCC1833 | lung | carcinoma | P | NP | NP |
| HCC1897 | lung | carcinoma | NP | NP | NP |
| HCC1937 | breast | carcinoma | NP | P | NP |
| HCC1954 | breast | carcinoma | NP | P | NP |
| HCC202 | breast | carcinoma | NP | NP | NP |
| HCC2108 | lung | carcinoma | NP | P | NP |
| HCC2157 | breast | carcinoma | P | P | P |
| HCC2218 | breast | carcinoma | NP | NP | NP |
| HCC2279 | lung | carcinoma | NP | P | NP |
| HCC2814 | lung | carcinoma | NP | P | NP |
| HCC2935 | lung | carcinoma | NP | NP | NP |
| HCC364 | lung | carcinoma | NP | NP | NP |
| HCC366 | lung | carcinoma | NP | P | NP |
| HCC38 | breast | carcinoma | NP | P | NP |

FIG. 19 (cont.)

| Cell Line Name | Primary site | Histology | IFN | ANTXR1 | Predictor |
|---|---|---|---|---|---|
| HCC4006 | lung | carcinoma | NP | P | NP |
| HCC44 | lung | carcinoma | NP | P | NP |
| HCC56 | large_intestine | carcinoma | NP | NP | NP |
| HCC70 | breast | carcinoma | NP | P | NP |
| HCC78 | lung | carcinoma | NP | NP | NP |
| HCC827GR5 | lung | carcinoma | NP | NP | NP |
| HCC827 | lung | carcinoma | NP | NP | NP |
| HCC95 | lung | carcinoma | NP | P | NP |
| HCT8 | large_intestine | carcinoma | NP | NP | NP |
| HDLM2 | Haematopoietic_lymphoid_tissue | lymphoid_neoplasm | NP | NP | NP |
| HDMYZ | haematopoietic_lymphoid_tissue | lymphoid_neoplasm | NP | P | NP |
| HDQP1 | breast | carcinoma | NP | P | NP |
| HEC108 | endometrium | carcinoma | NP | NP | NP |
| HEC151 | endometrium | carcinoma | NP | P | NP |
| HEC1A | endometrium | carcinoma | NP | P | NP |
| HEC1B | endometrium | carcinoma | NP | P | NP |
| HEC251 | endometrium | carcinoma | NP | P | NP |
| HEC265 | endometrium | carcinoma | P | P | P |
| HEC50B | endometrium | carcinoma | NP | NP | NP |
| HEC59 | endometrium | carcinoma | NP | NP | NP |
| HEC6 | endometrium | carcinoma | NP | P | NP |
| HEL | haematopoietic_lymphoid_tissue | haematopoietic_neoplasm | NP | NP | NP |
| HGC27 | stomach | carcinoma | NP | P | NP |
| HH | haematopoietic _lymphoid_tissue | lymphoid_neoplasm | NP | NP | NP |
| HK2 | kidney | other | NP | P | NP |
| HLC1 | lung | carcinoma | NP | P | NP |
| HLE | liver | carcinoma | NP | P | NP |
| HLF | liver | carcinoma | NP | P | NP |
| HMC18 | breast | carcinoma | NP | P | NP |
| HMCB | skin | malignant_melanoma | NP | P | NP |
| HMEL | breast | other | NP | P | NP |
| HOS | bone | osteosarcoma | P | P | P |
| HPAC | pancreas | carcinoma | P | P | P |
| HPAFII | pancreas | carcinoma | NP | NP | NP |
| HPBALL | haematopoietic _lymphoid_tissue | lymphoid_neoplasm | NP | P | NP |
| HSC2 | upper_aerodigestive_tract | carcinoma | NP | P | NP |

FIG. 19 (cont.)

| Cell Line Name | Primary_site | Histology | IFN | ANTXR1 | Predictor |
|---|---|---|---|---|---|
| HSC3 | upper_aerodigestive_tract | carcinoma | NP | P | NP |
| HSC4 | upper_aerodigestive_tract | carcinoma | NP | P | NP |
| HT1080 | soft_tissue | fibrosarcoma | NP | P | NP |
| HT115 | large_intestine | carcinoma | NP | NP | NP |
| HT1197 | urinary_tract | carcinoma | NP | NP | NP |
| HT1376 | urinary_tract | carcinoma | NP | P | NP |
| HT144 | skin | malignant_melanoma | NP | P | NP |
| HT55 | large_intestine | carcinoma | NP | NP | NP |
| HT | haematopoietic_and_lymphoid_tissue | lymphoid_neoplasm | NP | NP | NP |
| HTK | haematopoietic_and_lymphoid_tissue | lymphoid_neoplasm | NP | P | NP |
| HUPT3 | pancreas | carcinoma | NP | P | NP |
| HUPT4 | pancreas | carcinoma | NP | P | NP |
| IALM | lung | carcinoma | NP | P | NP |
| IGR1 | skin | malignant_melanoma | NP | P | NP |
| IGR37 | skin | malignant_melanoma | NP | P | NP |
| IGR39 | skin | malignant_melanoma | NP | P | NP |
| IM95 | stomach | carcinoma | NP | NP | NP |
| IPC298 | skin | malignant_melanoma | NP | P | NP |
| ISTMES1 | pleura | mesothelioma | NP | P | NP |
| ISTMES2 | pleura | mesothelioma | NP | P | NP |
| J82 | urinary_tract | carcinoma | NP | P | NP |
| JHH1 | liver | carcinoma | NP | NP | NP |
| JHH2 | liver | carcinoma | NP | NP | NP |
| JHH4 | liver | carcinoma | NP | P | NP |
| JHH5 | liver | carcinoma | NP | NP | NP |
| JHH6 | liver | carcinoma | NP | P | NP |
| JHH7 | liver | carcinoma | NP | NP | NP |
| JHOC5 | ovary | carcinoma | NP | P | NP |
| JHOM1 | ovary | carcinoma | NP | P | NP |
| JHOM2B | ovary | carcinoma | NP | NP | NP |
| JHOS2 | ovary | carcinoma | NP | P | NP |
| JHOS4 | ovary | carcinoma | NP | NP | NP |
| JHUEM1 | endometrium | carcinoma | NP | P | NP |
| JHUEM2 | endometrium | carcinoma | P | P | P |
| JHUEM3 | endometrium | carcinoma | NP | P | NP |
| JIMT1 | breast | carcinoma | NP | P | NP |

FIG. 19 (cont.)

| Cell Line Name | Primary site | Histology | IFN | ANTXR1 | Predictor |
|---|---|---|---|---|---|
| JJN3 | haematopoietic_and_lymphoid_tissue | lymphoid_neoplasm | NP | NP | NP |
| JK1 | haematopoietic_and_lymphoid_tissue | haematopoietic_neoplasm | NP | NP | NP |
| JL1 | pleura | mesothelioma | NP | P | NP |
| JM1 | haematopoietic_and_lymphoid_tissue | lymphoid_neoplasm | NP | NP | NP |
| JMSU1 | urinary_tract | carcinoma | NP | P | NP |
| JURKAT | haematopoietic_and_lymphoid_tissue | lymphoid_neoplasm | NP | P | NP |
| JURLMK1 | haematopoietic_and_lymphoid_tissue | haematopoietic_neoplasm | NP | NP | NP |
| JVM2 | haematopoietic_and_lymphoid_tissue | lymphoid_neoplasm | NP | NP | NP |
| JVM3 | haematopoietic_and_lymphoid_tissue | lymphoid_neoplasm | NP | NP | NP |
| K029AX | skin | malignant_melanoma | NP | P | NP |
| KALS1 | central_nervous_system | glioma | NP | P | NP |
| KARPAS422 | haematopoietic_and_lymphoid_tissue | lymphoid_neoplasm | NP | NP | NP |
| KARPAS620 | haematopoietic_and_lymphoid_tissue | lymphoid_neoplasm | NP | NP | NP |
| KASUMI2 | haematopoietic_and_lymphoid_tissue | lymphoid_neoplasm | NP | NP | NP |
| KCIMOH1 | pancreas | carcinoma | NP | P | NP |
| KCL22 | haematopoietic_and_lymphoid_tissue | haematopoietic_neoplasm | NP | P | NP |
| KE37 | haematopoietic_and_lymphoid_tissue | lymphoid_neoplasm | NP | P | NP |
| KE39 | stomach | carcinoma | NP | NP | NP |
| KE97 | haematopoietic_and_lymphoid_tissue | lymphoid_neoplasm | NP | NP | NP |
| KELLY | autonomic_ganglia | neuroblastoma | P | P | P |
| KG1C | central_nervous_system | glioma | NP | P | NP |
| KG1 | haematopoietic_and_lymphoid_tissue | haematopoietic_neoplasm | NP | NP | NP |
| KHM1B | haematopoietic_and_lymphoid_tissue | lymphoid_neoplasm | NP | NP | NP |
| KLE | endometrium | carcinoma | NP | P | NP |
| KLM1 | pancreas | carcinoma | NP | P | NP |
| KMBC2 | urinary_tract | carcinoma | NP | P | NP |
| KMH2 | haematopoietic_and_lymphoid_tissue | lymphoid_neoplasm | NP | NP | NP |
| KMM1 | haematopoietic_and_lymphoid_tissue | lymphoid_neoplasm | NP | P | NP |
| KMRC1 | kidney | carcinoma | NP | P | NP |
| KMRC20 | kidney | carcinoma | NP | NP | NP |
| KMRC2 | kidney | carcinoma | NP | P | NP |
| KMRC3 | kidney | carcinoma | NP | P | NP |
| KMS11 | haematopoietic_and_lymphoid_tissue | lymphoid_neoplasm | NP | NP | NP |
| KMS12BM | haematopoietic_and_lymphoid_tissue | lymphoid_neoplasm | NP | NP | NP |
| KMS18 | haematopoietic_and_lymphoid_tissue | lymphoid_neoplasm | NP | NP | NP |
| KMS20 | haematopoietic_and_lymphoid_tissue | lymphoid_neoplasm | NP | P | NP |

FIG. 19 (cont.)

| Cell Line Name | Primary site | Histology | IFN | ANTXR1 | Predictor |
|---|---|---|---|---|---|
| KMS21BM | haematopoietic_and_lymphoid_tissue | lymphoid_neoplasm | NP | NP | NP |
| KMS26 | haematopoietic_and_lymphoid_tissue | lymphoid_neoplasm | NP | NP | NP |
| KMS27 | haematopoietic_and_lymphoid_tissue | lymphoid_neoplasm | NP | NP | NP |
| KMS28BM | haematopoietic_and_lymphoid_tissue | lymphoid_neoplasm | NP | P | NP |
| KMS34 | haematopoietic_and_lymphoid_tissue | lymphoid_neoplasm | NP | P | NP |
| KNS42 | central_nervous_system | glioma | NP | P | NP |
| KNS60 | central_nervous_system | glioma | NP | P | NP |
| KNS62 | lung | carcinoma | NP | P | NP |
| KNS81 | central_nervous_system | glioma | NP | P | NP |
| KO52 | haematopoietic_and_lymphoid_tissue | haematopoietic_neoplasm | NP | NP | NP |
| KOPN8 | haematopoietic_and_lymphoid_tissue | lymphoid_neoplasm | NP | NP | NP |
| KP2 | pancreas | carcinoma | NP | P | NP |
| KP3 | pancreas | carcinoma | NP | NP | NP |
| KP4 | pancreas | carcinoma | NP | P | NP |
| KPL1 | breast | carcinoma | NP | NP | NP |
| KPNRTBM1 | autonomic_ganglia | neuroblastoma | P | P | P |
| KPNYN | autonomic_ganglia | neuroblastoma | P | P | P |
| KS1 | central_nervous_system | glioma | NP | P | NP |
| KU1919 | urinary_tract | carcinoma | P | P | P |
| KU812 | haematopoietic_and_lymphoid_tissue | haematopoietic_neoplasm | NP | NP | NP |
| KURAMOCHI | ovary | carcinoma | NP | P | NP |
| KYM1 | soft_tissue | rhabdomyosarcoma | NP | NP | NP |
| KYO1 | haematopoietic_and_lymphoid_tissue | haematopoietic_neoplasm | NP | P | NP |
| KYSE140 | oesophagus | carcinoma | P | P | P |
| KYSE150 | oesophagus | carcinoma | NP | P | NP |
| KYSE180 | oesophagus | carcinoma | NP | P | NP |
| KYSE270 | oesophagus | carcinoma | NP | P | NP |
| KYSE30 | oesophagus | carcinoma | NP | P | NP |
| KYSE410 | oesophagus | carcinoma | NP | P | NP |
| KYSE450 | oesophagus | carcinoma | NP | P | NP |
| KYSE510 | oesophagus | carcinoma | NP | P | NP |
| KYSE520 | oesophagus | carcinoma | NP | P | NP |
| KYSE70 | oesophagus | carcinoma | NP | P | NP |
| L1236 | haematopoietic_and_lymphoid_tissue | lymphoid_neoplasm | NP | NP | NP |
| L363 | haematopoietic_and_lymphoid_tissue | lymphoid_neoplasm | NP | NP | NP |
| L428 | haematopoietic_and_lymphoid_tissue | lymphoid_neoplasm | NP | NP | NP |

FIG. 19 (cont.)

| Cell Line Name | Primary site | Histology | IFN | ANTXR1 | Predictor |
|---|---|---|---|---|---|
| L540 | haematopoietic_and_lymphoid_tissue | lymphoid_neoplasm | NP | NP | NP |
| LAMA84 | haematopoietic_and_lymphoid_tissue | haematopoietic_neoplasm | NP | NP | NP |
| LC1F | lung | carcinoma | NP | P | NP |
| LCLC103H | lung | carcinoma | NP | P | NP |
| LCLC97TM1 | lung | carcinoma | NP | NP | NP |
| LK2 | lung | carcinoma | P | P | P |
| LMSU | stomach | carcinoma | NP | P | NP |
| LN18 | central_nervous_system | glioma | NP | P | NP |
| LN215 | central_nervous_system | glioma | NP | P | NP |
| LN229 | central_nervous_system | glioma | NP | P | NP |
| LN235 | central_nervous_system | glioma | NP | P | NP |
| LN319 | central_nervous_system | glioma | NP | P | NP |
| LN340 | central_nervous_system | glioma | NP | P | NP |
| LN382 | central_nervous_system | glioma | NP | P | NP |
| LN428 | central_nervous_system | glioma | NP | P | NP |
| LN443 | central_nervous_system | glioma | NP | P | NP |
| LN464 | central_nervous_system | glioma | NP | P | NP |
| LNZ308 | central_nervous_system | glioma | NP | P | NP |
| LOUNH91 | lung | carcinoma | NP | P | NP |
| LP1 | haematopoietic_and_lymphoid_tissue | lymphoid_neoplasm | NP | P | NP |
| LS1034 | large_intestine | carcinoma | NP | NP | NP |
| LS123 | large_intestine | carcinoma | NP | P | NP |
| LS411N | large_intestine | carcinoma | NP | NP | NP |
| LS513 | large_intestine | carcinoma | NP | NP | NP |
| LU65 | lung | carcinoma | P | NP | NP |
| LU99 | lung | carcinoma | NP | P | NP |
| LUDLU1 | lung | carcinoma | NP | NP | NP |
| LXF289 | lung | carcinoma | NP | P | NP |
| MC116 | haematopoietic_and_lymphoid_tissue | lymphoid_neoplasm | NP | NP | NP |
| MCAS | ovary | carcinoma | NP | P | NP |
| MDAMB134VI | breast | carcinoma | NP | NP | NP |
| MDAMB157 | breast | carcinoma | NP | P | NP |
| MDAMB175VII | breast | carcinoma | NP | NP | NP |
| MDAMB361 | breast | carcinoma | NP | P | NP |
| MDAMB415 | breast | carcinoma | NP | NP | NP |
| MDAMB435S | skin | malignant_melanoma | NP | P | NP |

FIG. 19 (cont.)

| Cell Line Name | Primary site | Histology | IFN | ANTXR1 | Predictor |
|---|---|---|---|---|---|
| MDAMB436 | breast | carcinoma | NP | P | NP |
| MDAMB453 | breast | carcinoma | P | NP | NP |
| MDAMB468 | breast | carcinoma | NP | P | NP |
| MDST8 | large_intestine | carcinoma | NP | P | NP |
| ME1 | haematopoietic_and_lymphoid_tissue | haematopoietic_neoplasm | NP | NP | NP |
| MEC1 | haematopoietic_and_lymphoid_tissue | lymphoid_neoplasm | NP | NP | NP |
| MEC2 | haematopoietic_and_lymphoid_tissue | lymphoid_neoplasm | NP | NP | NP |
| MEG01 | haematopoietic_and_lymphoid_tissue | haematopoietic_neoplasm | NP | NP | NP |
| MELHO | skin | malignant_melanoma | NP | P | NP |
| MELJUSO | skin | malignant_melanoma | NP | P | NP |
| MESSA | soft_tissue | sarcoma | NP | P | NP |
| MFE280 | endometrium | carcinoma | NP | P | NP |
| MFE296 | endometrium | carcinoma | NP | P | NP |
| MFE319 | endometrium | carcinoma | NP | P | NP |
| MG63 | bone | osteosarcoma | NP | P | NP |
| MHHCALL2 | haematopoietic_and_lymphoid_tissue | lymphoid_neoplasm | NP | NP | NP |
| MHHCALL3 | haematopoietic_and_lymphoid_tissue | lymphoid_neoplasm | NP | NP | NP |
| MHHCALL4 | haematopoietic_and_lymphoid_tissue | lymphoid_neoplasm | NP | NP | NP |
| MHHES1 | bone | Ewings_sarcoma | NP | P | NP |
| MHHNB11 | autonomic_ganglia | neuroblastoma | P | P | P |
| MJ | haematopoietic_and_lymphoid_tissue | lymphoid_neoplasm | NP | NP | NP |
| MKN1 | stomach | carcinoma | NP | P | NP |
| MKN45 | stomach | carcinoma | NP | NP | NP |
| MKN74 | stomach | carcinoma | NP | NP | NP |
| MKN7 | stomach | carcinoma | NP | P | NP |
| ML1 | thyroid | carcinoma | NP | P | NP |
| MM1S | haematopoietic_and_lymphoid_tissue | lymphoid_neoplasm | NP | NP | NP |
| MOGGCCM | central_nervous_system | glioma | NP | P | NP |
| MOGGUVW | central_nervous_system | glioma | NP | P | NP |
| MOLM13 | haematopoietic_and_lymphoid_tissue | haematopoietic_neoplasm | NP | NP | NP |
| MOLM16 | haematopoietic_and_lymphoid_tissue | haematopoietic_neoplasm | NP | NP | NP |
| MOLM6 | haematopoietic_and_lymphoid_tissue | haematopoietic_neoplasm | NP | NP | NP |
| MOLP2 | haematopoietic_and_lymphoid_tissue | lymphoid_neoplasm | NP | NP | NP |
| MOLP8 | haematopoietic_and_lymphoid_tissue | lymphoid_neoplasm | NP | P | NP |
| MOLT13 | haematopoietic_and_lymphoid_tissue | lymphoid_neoplasm | NP | P | NP |
| MOLT16 | haematopoietic_and_lymphoid_tissue | lymphoid_neoplasm | NP | NP | NP |

FIG. 19 (cont.)

| Cell Line Name | Primary site | Histology | IFN | ANTXR1 | Predictor |
|---|---|---|---|---|---|
| MONOMAC1 | haematopoietic_and_lymphoid_tissue | haematopoietic_neoplasm | NP | NP | NP |
| MONOMAC6 | haematopoietic_and_lymphoid_tissue | haematopoietic_neoplasm | NP | NP | NP |
| MOTN1 | haematopoietic_and_lymphoid_tissue | lymphoid_neoplasm | NP | NP | NP |
| MSTO211H | pleura | mesothelioma | NP | P | NP |
| MUTZ5 | haematopoietic_and_lymphoid_tissue | lymphoid_neoplasm | NP | NP | NP |
| MV411 | haematopoietic_and_lymphoid_tissue | haematopoietic_neoplasm | NP | NP | NP |
| NALM19 | haematopoietic_and_lymphoid_tissue | lymphoid_neoplasm | NP | NP | NP |
| NALM1 | haematopoietic_and_lymphoid_tissue | haematopoietic_neoplasm | NP | NP | NP |
| NAMALWA | haematopoietic_and_lymphoid_tissue | lymphoid_neoplasm | NP | NP | NP |
| NB1 | autonomic_ganglia | neuroblastoma | P | P | P |
| NB4 | haematopoietic_and_lymphoid_tissue | haematopoietic_neoplasm | NP | NP | NP |
| NCIH1048 | lung | carcinoma | NP | P | NP |
| NCIH1092 | lung | carcinoma | P | P | P |
| NCIH1105 | lung | carcinoma | P | P | P |
| NCIH1155 | lung | carcinoma | NP | P | NP |
| NCIH1341 | lung | carcinoma | P | P | P |
| NCIH1355 | lung | carcinoma | NP | P | NP |
| NCIH1373 | lung | carcinoma | NP | P | NP |
| NCIH1385 | lung | carcinoma | NP | NP | NP |
| NCIH1395 | lung | carcinoma | NP | NP | NP |
| NCIH1435 | lung | carcinoma | NP | NP | NP |
| NCIH1436 | lung | carcinoma | P | P | P |
| NCIH1437 | lung | carcinoma | NP | NP | NP |
| NCIH1563 | lung | carcinoma | NP | P | NP |
| NCIH1568 | lung | carcinoma | NP | P | NP |
| NCIH1573 | lung | carcinoma | NP | NP | NP |
| NCIH1581 | lung | carcinoma | NP | NP | NP |
| NCIH1623 | lung | carcinoma | NP | P | NP |
| NCIH1648 | lung | carcinoma | NP | P | NP |
| NCIH1650 | lung | carcinoma | NP | P | NP |
| NCIH1651 | lung | carcinoma | NP | P | NP |
| NCIH1666 | lung | carcinoma | NP | P | NP |
| NCIH1693 | lung | carcinoma | NP | P | NP |
| NCIH1694 | lung | carcinoma | P | P | P |
| NCIH1703 | lung | carcinoma | NP | P | NP |
| NCIH1734 | lung | carcinoma | NP | P | NP |

FIG. 19 (cont.)

| Cell Line Name | Primary site | Histology | IFN | ANTXR1 | Predictor |
|---|---|---|---|---|---|
| NCIH1755 | lung | carcinoma | NP | P | NP |
| NCIH1781 | lung | carcinoma | NP | NP | NP |
| NCIH1792 | lung | carcinoma | NP | P | NP |
| NCIH1793 | lung | carcinoma | NP | P | NP |
| NCIH1836 | lung | carcinoma | NP | NP | NP |
| NCIH1838 | lung | carcinoma | NP | NP | NP |
| NCIH1869 | lung | carcinoma | NP | NP | NP |
| NCIH1876 | lung | carcinoma | P | P | P |
| NCIH1915 | lung | carcinoma | NP | P | NP |
| NCIH1930 | lung | carcinoma | P | P | P |
| NCIH1944 | lung | carcinoma | NP | NP | NP |
| NCIH196 | lung | carcinoma | NP | P | NP |
| NCIH1975 | lung | carcinoma | NP | NP | NP |
| NCIH2009 | lung | carcinoma | NP | P | NP |
| NCIH2023 | lung | carcinoma | NP | P | NP |
| NCIH2029 | lung | carcinoma | NP | P | NP |
| NCIH2030 | lung | carcinoma | NP | P | NP |
| NCIH2052 | pleura | mesothelioma | NP | P | NP |
| NCIH2066 | lung | carcinoma | P | NP | NP |
| NCIH2081 | lung | carcinoma | NP | NP | NP |
| NCIH2085 | lung | carcinoma | P | P | P |
| NCIH2087 | lung | carcinoma | NP | NP | NP |
| NCIH2106 | lung | carcinoma | P | P | P |
| NCIH2110 | lung | carcinoma | NP | NP | NP |
| NCIH211 | lung | carcinoma | P | NP | NP |
| NCIH2122 | lung | carcinoma | NP | NP | NP |
| NCIH2126 | lung | carcinoma | NP | NP | NP |
| NCIH2141 | lung | carcinoma | P | P | P |
| NCIH2170 | lung | carcinoma | NP | NP | NP |
| NCIH2171 | lung | carcinoma | P | P | P |
| NCIH2172 | lung | carcinoma | NP | P | NP |
| NCIH2196 | lung | carcinoma | NP | P | NP |
| NCIH2227 | lung | carcinoma | NP | P | NP |
| NCIH2228 | lung | carcinoma | NP | P | NP |
| NCIH2286 | lung | carcinoma | NP | P | NP |
| NCIH2291 | lung | carcinoma | NP | NP | NP |

FIG. 19 (cont.)

| Cell Line Name | Primary site | Histology | IFN | ANTXR1 | Predictor |
|---|---|---|---|---|---|
| NCIH2342 | lung | carcinoma | P | P | P |
| NCIH2347 | lung | carcinoma | NP | NP | NP |
| NCIH2405 | lung | carcinoma | NP | NP | NP |
| NCIH2444 | lung | carcinoma | NP | P | NP |
| NCIH2452 | pleura | mesothelioma | NP | P | NP |
| NCIH28 | pleura | mesothelioma | NP | P | NP |
| NCIH292 | lung | carcinoma | NP | P | NP |
| NCIH322 | lung | carcinoma | P | NP | NP |
| NCIH3255 | lung | carcinoma | NP | P | NP |
| NCIH358 | lung | carcinoma | NP | NP | NP |
| NCIH441 | lung | carcinoma | NP | NP | NP |
| NCIH508 | large_intestine | carcinoma | NP | NP | NP |
| NCIH510 | lung | carcinoma | P | P | P |
| NCIH520 | lung | carcinoma | NP | P | NP |
| NCIH524 | lung | carcinoma | P | P | P |
| NCIH596 | lung | carcinoma | NP | P | NP |
| NCIH647 | lung | carcinoma | NP | P | NP |
| NCIH650 | lung | carcinoma | NP | NP | NP |
| NCIH660 | prostate | carcinoma | NP | P | NP |
| NCIH661 | lung | carcinoma | NP | P | NP |
| NCIH684 | liver | other | NP | NP | NP |
| NCIH716 | large_intestine | carcinoma | NP | NP | NP |
| NCIH747 | large_intestine | carcinoma | NP | NP | NP |
| NCIH810 | lung | carcinoma | P | NP | NP |
| NCIH838 | lung | carcinoma | NP | P | NP |
| NCIH841 | lung | carcinoma | NP | NP | NP |
| NCIH854 | lung | carcinoma | NP | NP | NP |
| NCIH889 | lung | carcinoma | NP | NP | NP |
| NCIH929 | haematopoietic_and_lymphoid_tissue | lymphoid_neoplasm | NP | NP | NP |
| NCIN87 | stomach | carcinoma | NP | P | NP |
| NCO2 | haematopoietic_and_lymphoid_tissue | haematopoietic_neoplasm | NP | NP | NP |
| NH6 | autonomic_ganglia | neuroblastoma | P | P | P |
| NMCG1 | central_nervous_system | glioma | NP | P | NP |
| NOMO1 | haematopoietic_and_lymphoid_tissue | haematopoietic_neoplasm | NP | NP | NP |
| NUDHL1 | haematopoietic_and_lymphoid_tissue | lymphoid_neoplasm | NP | NP | NP |
| NUDUL1 | haematopoietic_and_lymphoid_tissue | lymphoid_neoplasm | NP | NP | NP |

FIG. 19 (cont.)

| Cell Line Name | Primary site | Histology | IFN | ANTXR1 | Predictor |
|---|---|---|---|---|---|
| NUGC2 | stomach | carcinoma | NP | P | NP |
| NUGC3 | stomach | carcinoma | NP | NP | NP |
| NUGC4 | stomach | carcinoma | NP | NP | NP |
| OAW28 | ovary | carcinoma | NP | P | NP |
| OAW42 | ovary | carcinoma | NP | NP | NP |
| OCIAML2 | haematopoietic_and_lymphoid_tissue | haematopoietic_neoplasm | NP | NP | NP |
| OCIAML3 | haematopoietic_and_lymphoid_tissue | haematopoietic_neoplasm | NP | NP | NP |
| OCIAML5 | haematopoietic_and_lymphoid_tissue | haematopoietic_neoplasm | NP | NP | NP |
| OCILY10 | haematopoietic_and_lymphoid_tissue | lymphoid_neoplasm | NP | NP | NP |
| OCILY19 | haematopoietic_and_lymphoid_tissue | lymphoid_neoplasm | NP | NP | NP |
| OCILY3 | haematopoietic_and_lymphoid_tissue | lymphoid_neoplasm | NP | NP | NP |
| OCIM1 | haematopoietic_and_lymphoid_tissue | haematopoietic_neoplasm | NP | NP | NP |
| OCUM1 | stomach | carcinoma | NP | NP | NP |
| OE19 | oesophagus | carcinoma | NP | NP | NP |
| OE33 | oesophagus | other | NP | NP | NP |
| OELE | ovary | other | NP | P | NP |
| ONCODG1 | ovary | carcinoma | P | P | P |
| ONS76 | central_nervous_system | primitive_neuroectodermal | NP | P | NP |
| OPM2 | haematopoietic_and_lymphoid_tissue | lymphoid_neoplasm | NP | NP | NP |
| OSRC2 | kidney | carcinoma | NP | P | NP |
| OUMS23 | large_intestine | carcinoma | P | P | P |
| OUMS27 | bone | chondrosarcoma | P | P | P |
| OV56 | ovary | carcinoma | NP | P | NP |
| OV7 | ovary | carcinoma | NP | P | NP |
| OV90 | ovary | carcinoma | NP | P | NP |
| OVISE | ovary | carcinoma | NP | NP | NP |
| OVK18 | ovary | carcinoma | NP | NP | NP |
| OVKATE | ovary | carcinoma | NP | P | NP |
| OVMANA | ovary | carcinoma | NP | NP | NP |
| OVSAHO | ovary | carcinoma | NP | P | NP |
| OVTOKO | ovary | carcinoma | NP | NP | NP |
| P12ICHIKAWA | haematopoietic_and_lymphoid_tissue | lymphoid_neoplasm | NP | P | NP |
| P3HR1 | haematopoietic_and_lymphoid_tissue | lymphoid_neoplasm | NP | NP | NP |
| PANC1 | pancreas | carcinoma | NP | P | NP |
| PATU8902 | pancreas | carcinoma | NP | NP | NP |
| PATU8988S | pancreas | carcinoma | NP | NP | NP |

FIG. 19 (cont.)

| Cell Line Name | Primary site | Histology | IFN | ANTXR1 | Predictor |
|---|---|---|---|---|---|
| PATU8988T | pancreas | carcinoma | NP | P | NP |
| PC14 | lung | carcinoma | NP | P | NP |
| PCM6 | haematopoietic_and_lymphoid_tissue | lymphoid_neoplasm | NP | NP | NP |
| PEER | haematopoietic_and_lymphoid_tissue | lymphoid_neoplasm | NP | NP | NP |
| PF382 | haematopoietic_and_lymphoid_tissue | lymphoid_neoplasm | NP | P | NP |
| PK1 | pancreas | carcinoma | NP | P | NP |
| PK45H | pancreas | carcinoma | NP | P | NP |
| PK59 | pancreas | carcinoma | NP | NP | NP |
| PL21 | haematopoietic_and_lymphoid_tissue | haematopoietic_neoplasm | NP | NP | NP |
| PL45 | pancreas | carcinoma | NP | P | NP |
| PSN1 | pancreas | carcinoma | NP | P | NP |
| QGP1 | pancreas | carcinoma | NP | P | NP |
| RCC10RGB | kidney | carcinoma | NP | P | NP |
| RCC4 | kidney | carcinoma | NP | P | NP |
| RCHACV | haematopoietic_and_lymphoid_tissue | lymphoid_neoplasm | NP | P | NP |
| RCM1 | large_intestine | carcinoma | NP | NP | NP |
| RDES | bone | Ewings_sarcoma | P | P | P |
| REC1 | haematopoietic_and_lymphoid_tissue | lymphoid_neoplasm | NP | NP | NP |
| RERFGC1B | stomach | carcinoma | NP | P | NP |
| RERFLCAI | lung | carcinoma | NP | P | NP |
| RERFLCKJ | lung | carcinoma | NP | NP | NP |
| RERFLCMS | lung | carcinoma | NP | P | NP |
| RI1 | haematopoietic_and_lymphoid_tissue | lymphoid_neoplasm | NP | NP | NP |
| RKN | soft_tissue | leiomyosarcoma | NP | P | NP |
| RKO | large_intestine | carcinoma | NP | NP | NP |
| RL952 | endometrium | carcinoma | NP | P | NP |
| RL | haematopoietic_and_lymphoid_tissue | lymphoid_neoplasm | NP | NP | NP |
| RMGI | ovary | carcinoma | NP | P | NP |
| RMUGS | ovary | carcinoma | NP | P | NP |
| RPMI7951 | skin | malignant_melanoma | NP | P | NP |
| RPMI8402 | haematopoietic_and_lymphoid_tissue | lymphoid_neoplasm | NP | P | NP |
| RS5 | pleura | mesothelioma | NP | P | NP |
| RT112 | urinary_tract | carcinoma | NP | P | NP |
| RT4 | urinary_tract | carcinoma | NP | P | NP |
| RVH421 | skin | malignant_melanoma | NP | P | NP |
| S117 | soft_tissue | sarcoma | NP | P | NP |

FIG. 19 (cont.)

| Cell Line Name | Primary site | Histology | IFN | ANTXR1 | Predictor |
|---|---|---|---|---|---|
| SALE | lung | other | NP | P | NP |
| SBC5 | lung | carcinoma | NP | NP | NP |
| SCC15 | upper_aerodigestive_tract | carcinoma | NP | P | NP |
| SCC25 | upper_aerodigestive_tract | carcinoma | NP | P | NP |
| SCC4 | upper_aerodigestive_tract | carcinoma | P | P | P |
| SCC9 | upper_aerodigestive_tract | carcinoma | NP | P | NP |
| SCLC21H | lung | carcinoma | P | P | P |
| SEM | haematopoietic_and_lymphoid_tissue | lymphoid_neoplasm | NP | P | NP |
| SF126 | central_nervous_system | glioma | NP | P | NP |
| SF172 | central_nervous_system | glioma | NP | P | NP |
| SF767 | central_nervous_system | glioma | NP | P | NP |
| SH10TC | stomach | carcinoma | NP | P | NP |
| SH4 | skin | malignant_melanoma | NP | P | NP |
| SHP77 | lung | carcinoma | P | P | P |
| SHSY5Y | autonomic_ganglia | neuroblastoma | P | P | P |
| SIGM5 | haematopoietic_and_lymphoid_tissue | haematopoietic_neoplasm | NP | NP | NP |
| SIMA | autonomic_ganglia | neuroblastoma | P | P | P |
| SJRH30 | soft_tissue | rhabdomyosarcoma | P | P | P |
| SJSA1 | bone | osteosarcoma | NP | P | NP |
| SKBR3 | breast | carcinoma | NP | NP | NP |
| SKCO1 | large_intestine | carcinoma | NP | NP | NP |
| SKES1 | bone | Ewings_sarcoma | P | P | P |
| SKHEP1 | liver | carcinoma | NP | P | NP |
| SKLMS1 | soft_tissue | sarcoma | NP | P | NP |
| SKLU1 | lung | carcinoma | NP | P | NP |
| SKM1 | haematopoietic_and_lymphoid_tissue | haematopoietic_neoplasm | NP | NP | NP |
| SKMEL1 | skin | malignant_melanoma | NP | NP | NP |
| SKMEL24 | skin | malignant_melanoma | NP | P | NP |
| SKMEL30 | skin | malignant_melanoma | NP | P | NP |
| SKMEL31 | skin | malignant_melanoma | NP | P | NP |
| SKMEL3 | skin | malignant_melanoma | NP | P | NP |
| SKMES1 | lung | carcinoma | NP | P | NP |
| SKMM2 | haematopoietic_and_lymphoid_tissue | lymphoid_neoplasm | NP | NP | NP |
| SKNDZ | autonomic_ganglia | neuroblastoma | P | P | P |
| SKNFI | autonomic_ganglia | neuroblastoma | P | P | P |
| SKRC20 | kidney | carcinoma | NP | P | NP |

FIG. 19 (cont.)

| Cell Line Name | Primary site | Histology | IFN | ANTXR1 | Predictor |
|---|---|---|---|---|---|
| SKUT1 | soft_tissue | leiomyosarcoma | NP | P | NP |
| SNGM | endometrium | carcinoma | NP | P | NP |
| SNU1033 | large_intestine | carcinoma | NP | NP | NP |
| SNU1040 | large_intestine | carcinoma | NP | NP | NP |
| SNU1041 | upper_aerodigestive_tract | carcinoma | NP | P | NP |
| SNU1066 | upper_aerodigestive_tract | carcinoma | NP | P | NP |
| SNU1076 | upper_aerodigestive_tract | carcinoma | NP | P | NP |
| SNU1077 | endometrium | carcinoma | NP | P | NP |
| SNU1079 | biliary_tract | carcinoma | NP | NP | NP |
| SNU1105 | central_nervous_system | glioma | NP | P | NP |
| SNU1196 | biliary_tract | carcinoma | NP | NP | NP |
| SNU1197 | large_intestine | carcinoma | NP | NP | NP |
| SNU119 | ovary | carcinoma | NP | NP | NP |
| SNU1214 | upper_aerodigestive_tract | carcinoma | NP | P | NP |
| SNU1272 | kidney | carcinoma | NP | P | NP |
| SNU16 | stomach | carcinoma | NP | NP | NP |
| SNU175 | large_intestine | carcinoma | NP | NP | NP |
| SNU182 | liver | carcinoma | P | P | P |
| SNU1 | stomach | carcinoma | P | P | P |
| SNU201 | central_nervous_system | glioma | NP | P | NP |
| SNU213 | pancreas | carcinoma | NP | P | NP |
| SNU216 | stomach | carcinoma | NP | P | NP |
| SNU245 | biliary_tract | carcinoma | NP | NP | NP |
| SNU283 | large_intestine | carcinoma | NP | NP | NP |
| SNU308 | biliary_tract | carcinoma | NP | P | NP |
| SNU324 | pancreas | carcinoma | NP | P | NP |
| SNU349 | kidney | carcinoma | NP | P | NP |
| SNU387 | liver | carcinoma | NP | P | NP |
| SNU398 | liver | carcinoma | NP | P | NP |
| SNU407 | large_intestine | carcinoma | NP | NP | NP |
| SNU410 | pancreas | carcinoma | NP | P | NP |
| SNU423 | liver | carcinoma | NP | P | NP |
| SNU449 | liver | carcinoma | NP | P | NP |
| SNU466 | central_nervous_system | glioma | NP | P | NP |
| SNU46 | upper_aerodigestive_tract | carcinoma | NP | P | NP |
| SNU475 | liver | carcinoma | NP | P | NP |

FIG. 19 (cont.)

| Cell Line Name | Primary site | Histology | IFN | ANTXR1 | Predictor |
|---|---|---|---|---|---|
| SNU478 | biliary_tract | carcinoma | NP | NP | NP |
| SNU489 | central_nervous_system | glioma | NP | P | NP |
| SNU503 | large_intestine | carcinoma | NP | P | NP |
| SNU520 | stomach | carcinoma | NP | NP | NP |
| SNU5 | stomach | carcinoma | NP | NP | NP |
| SNU601 | stomach | carcinoma | NP | NP | NP |
| SNU61 | large_intestine | carcinoma | NP | NP | NP |
| SNU620 | stomach | carcinoma | NP | NP | NP |
| SNU626 | central_nervous_system | glioma | NP | P | NP |
| SNU668 | stomach | carcinoma | NP | P | NP |
| SNU685 | endometrium | carcinoma | P | P | P |
| SNU719 | stomach | carcinoma | NP | NP | NP |
| SNU738 | central_nervous_system | glioma | NP | P | NP |
| SNU761 | liver | carcinoma | NP | P | NP |
| SNU81 | large_intestine | carcinoma | NP | NP | NP |
| SNU840 | ovary | carcinoma | NP | P | NP |
| SNU869 | biliary_tract | carcinoma | NP | NP | NP |
| SNU878 | liver | carcinoma | NP | P | NP |
| SNU886 | liver | carcinoma | NP | P | NP |
| SNU899 | upper_aerodigestive_tract | carcinoma | NP | P | NP |
| SNU8 | ovary | carcinoma | NP | P | NP |
| SNUC1 | large_intestine | carcinoma | NP | NP | NP |
| SNUC2A | large_intestine | carcinoma | NP | P | NP |
| SNUC4 | large_intestine | carcinoma | NP | NP | NP |
| SNUC5 | large_intestine | carcinoma | NP | NP | NP |
| SR786 | haematopoietic_and_lymphoid_tissue | lymphoid_neoplasm | NP | NP | NP |
| ST486 | haematopoietic_and_lymphoid_tissue | lymphoid_neoplasm | NP | NP | NP |
| SUDHL10 | haematopoietic_and_lymphoid_tissue | lymphoid_neoplasm | NP | NP | NP |
| SUDHL1 | haematopoietic_and_lymphoid_tissue | lymphoid_neoplasm | NP | NP | NP |
| SUDHL4 | haematopoietic_and_lymphoid_tissue | lymphoid_neoplasm | NP | NP | NP |
| SUDHL5 | haematopoietic_and_lymphoid_tissue | lymphoid_neoplasm | NP | NP | NP |
| SUDHL6 | haematopoietic_and_lymphoid_tissue | lymphoid_neoplasm | NP | NP | NP |
| SUDHL8 | haematopoietic_and_lymphoid_tissue | lymphoid_neoplasm | NP | NP | NP |
| SUIT2 | pancreas | carcinoma | NP | NP | NP |
| SUPB15 | haematopoietic_and_lymphoid_tissue | lymphoid_neoplasm | NP | P | NP |
| SUPHD1 | haematopoietic_and_lymphoid_tissue | lymphoid_neoplasm | NP | NP | NP |

FIG. 19 (cont.)

| Cell Line Name | Primary site | Histology | IFN | ANTXR1 | Predictor |
|---|---|---|---|---|---|
| SUPM2 | haematopoietic_and_lymphoid_tissue | lymphoid_neoplasm | NP | NP | NP |
| SUPT11 | haematopoietic_and_lymphoid_tissue | lymphoid_neoplasm | NP | P | NP |
| SUPT1 | haematopoietic_and_lymphoid_tissue | lymphoid_neoplasm | NP | P | NP |
| SW1116 | large_intestine | carcinoma | NP | NP | NP |
| SW1417 | large_intestine | carcinoma | NP | NP | NP |
| SW1463 | large_intestine | carcinoma | NP | NP | NP |
| SW1710 | urinary_tract | carcinoma | NP | P | NP |
| SW403 | large_intestine | carcinoma | NP | NP | NP |
| SW480 | large_intestine | carcinoma | NP | P | NP |
| SW48 | large_intestine | carcinoma | NP | NP | NP |
| SW579 | thyroid | carcinoma | NP | P | NP |
| SW837 | large_intestine | carcinoma | NP | NP | NP |
| SW948 | large_intestine | carcinoma | NP | NP | NP |
| T173 | bone | osteosarcoma | NP | P | NP |
| T24 | urinary_tract | carcinoma | NP | P | NP |
| T3M10 | lung | carcinoma | NP | P | NP |
| T3M4 | pancreas | carcinoma | NP | NP | NP |
| T84 | large_intestine | carcinoma | NP | NP | NP |
| T98G | central_nervous_system | glioma | NP | P | NP |
| TALL1 | haematopoietic_and_lymphoid_tissue | lymphoid_neoplasm | NP | P | NP |
| TC32 | bone | Ewings_sarcoma | NP | P | NP |
| TCCPAN2 | pancreas | carcinoma | NP | NP | NP |
| TCCSUP | urinary_tract | carcinoma | NP | P | NP |
| TE10 | oesophagus | carcinoma | NP | P | NP |
| TE11 | oesophagus | carcinoma | NP | P | NP |
| TE14 | oesophagus | carcinoma | NP | P | NP |
| TE15 | oesophagus | carcinoma | NP | NP | NP |
| TE1 | oesophagus | carcinoma | NP | P | NP |
| TE4 | oesophagus | carcinoma | P | P | P |
| TE5 | oesophagus | carcinoma | NP | NP | NP |
| TE6 | oesophagus | carcinoma | NP | P | NP |
| TE8 | oesophagus | carcinoma | NP | P | NP |
| TE9 | oesophagus | carcinoma | NP | P | NP |
| TEN | endometrium | carcinoma | NP | P | NP |
| TF1 | haematopoietic_and_lymphoid_tissue | haematopoietic_neoplasm | NP | NP | NP |
| TGBC11TKB | stomach | carcinoma | NP | NP | NP |

FIG. 19 (cont.)

| Cell Line Name | Primary_site | Histology | IFN | ANTXR1 | Predictor |
|---|---|---|---|---|---|
| THP1 | haematopoietic_and_lymphoid_tissue | haematopoietic_neoplasm | NP | NP | NP |
| TM31 | central_nervous_system | glioma | NP | P | NP |
| TOV112D | ovary | carcinoma | NP | P | NP |
| TOV21G | ovary | carcinoma | NP | P | NP |
| TT2609C02 | thyroid | carcinoma | NP | P | NP |
| TT | thyroid | carcinoma | NP | NP | NP |
| TUHR10TKB | kidney | carcinoma | NP | P | NP |
| TUHR14TKB | kidney | carcinoma | NP | P | NP |
| TUHR4TKB | kidney | carcinoma | NP | P | NP |
| U178 | central_nervous_system | glioma | NP | P | NP |
| U266B1 | haematopoietic_and_lymphoid_tissue | lymphoid_neoplasm | NP | NP | NP |
| U343 | central_nervous_system | glioma | NP | P | NP |
| U937 | haematopoietic_and_lymphoid_tissue | lymphoid_neoplasm | NP | NP | NP |
| UACC812 | breast | carcinoma | NP | NP | NP |
| UACC893 | breast | carcinoma | NP | NP | NP |
| UBLC1 | urinary_tract | carcinoma | NP | P | NP |
| UMRC2 | kidney | carcinoma | NP | P | NP |
| UMRC6 | kidney | carcinoma | NP | P | NP |
| UMUC1 | urinary_tract | carcinoma | NP | P | NP |
| UMUC3 | urinary_tract | carcinoma | NP | P | NP |
| UOK101 | kidney | carcinoma | NP | P | NP |
| UT7 | haematopoietic_and_lymphoid_tissue | haematopoietic_neoplasm | NP | NP | NP |
| VMCUB1 | urinary_tract | carcinoma | NP | P | NP |
| VMRCLCD | lung | carcinoma | NP | NP | NP |
| VMRCLCP | lung | carcinoma | NP | P | NP |
| VMRCRCW | kidney | carcinoma | NP | NP | NP |
| VMRCRCZ | kidney | carcinoma | NP | P | NP |
| WM115 | skin | malignant_melanoma | NP | P | NP |
| WM1799 | skin | malignant_melanoma | NP | P | NP |
| WM2664 | skin | malignant_melanoma | NP | P | NP |
| WM793 | skin | malignant_melanoma | NP | P | NP |
| WM88 | skin | malignant_melanoma | NP | P | NP |
| WM983B | skin | malignant_melanoma | NP | P | NP |
| WSUDLCL2 | haematopoietic_and_lymphoid_tissue | lymphoid_neoplasm | NP | NP | NP |
| YAPC | pancreas | carcinoma | NP | P | NP |
| YD10B | upper_aerodigestive_tract | carcinoma | NP | P | NP |

FIG. 19 (cont.)

| Cell Line Name | Primary site | Histology | IFN | ANTXR1 | Predictor |
|---|---|---|---|---|---|
| YD15 | salivary_gland | carcinoma | NP | P | NP |
| YD38 | upper_aerodigestive_tract | carcinoma | NP | P | NP |
| YD8 | upper_aerodigestive_tract | carcinoma | NP | P | NP |
| YH13 | central_nervous_system | glioma | NP | P | NP |
| YKG1 | central_nervous_system | glioma | NP | P | NP |
| YMB1 | breast | carcinoma | P | NP | NP |
| ZR751 | breast | carcinoma | NP | NP | NP |
| ZR7530 | breast | carcinoma | NP | NP | NP |

FIG. 19 (cont.)

COMPOSITIONS AND METHODS OF USING SENECA VALLEY VIRUS (SVV) FOR TREATING CANCER

CROSS-REFERENCE TO RELATED APPLICATIONS

This application is the National Stage Application of International Patent Application No. PCT/US2020/027784, filed Apr. 10, 2020, which claims priority to U.S. provisional application No. 62/832,509, filed Apr. 11, 2019, the disclosures of which is are incorporated herein by reference in their entireties.

TECHNICAL FIELD

The disclosed inventions relate to compositions and methods for treating cancer. More particularly, the disclosed inventions relate to the field of treating cancer in a subject using an oncolytic virus.

BACKGROUND

Oncolytic viruses have shown great potential as anti-cancer agents thanks to their ability kill tumors in the absence of damage to normal cells. The oncolytic virus Seneca Valley Virus (SVV) was originally shown to replicate and kill cancer cells with neuroendocrine properties, such as small cell lung cancer (SCLC), a variety of solid pediatric cancers, and carcinoid cancers. Unfortunately, both SCLC and solid pediatric cancer patients are some of the most difficult cancers to treat because of the short life span of patients following their failure to respond to standard of care therapy or have developed resistance. Data from clinical trials showed no evidence of SVV infection or replication within normal tissue surrounding the tumor. However, despite great potential for SVV based oncolytic viral therapies many tumors did not respond to SVV therapy.

Anthrax toxin receptor 1 (ANTXR1) is known to promote angiogenesis during disease development and is not required for normal cellular physiology. Recently, ANTXR1 was shown to interact directly and specifically with SVV. ANTXR1 expression on tumor cells was proven to be essential for SAN infection. However, the presence of ANTXR1 on various type of solid cancer tumors is not sufficient to favor an optimal permissively and replication of SVV and thus killing of cancer cells.

SUMMARY

Provided herein are methods of treating a cancer in a subject in need thereof. The methods comprise administering to the subject an effective amount of Seneca Valley Virus (SVV) or SVV derivative, wherein the cancer is characterized by (a) an expression level of anthrax toxin receptor 1 (ANTXR1) higher than an ANTXR1 reference value, and (b) an expression level of interferon type I (IFN-I) lower than an IFN-I reference value, wherein the subject is also administered at least one IFN-I inhibiting comprising a JAK inhibitor.

Also provided herein are other methods of treating a cancer in a subject in need thereof. The methods comprise administering to the subject an IFN-I inhibiting agent comprising a JAK inhibitor and an effective amount of SVV or SVV derivative, wherein the cancer is characterized by an expression level of ANTXR1 higher than an ANTXR1 reference value, and wherein the IFN-I inhibiting agent reduces the expression level of IFN-I in the cancer thereby favoring replication of the SVV or the SVV derivative and killing of the cancer.

Also provided herein are methods of predicting the efficacy of a cancer treatment comprising an Seneca Valley Virus (SVV), or an SVV derivative, combined with at least one IFN-I inhibiting agent comprising a JAK inhibitor. The methods comprise determining the expression level of ANTXR1 and the expression level of IFN-I in the cancer from a subject, wherein (a) an expression level of ANTXR1 higher than an ANTXR1 reference value, and (a) an expression level of IFN-I lower than an IFN-I reference value are predictive that the treatment is effective, and wherein when the treatment is predicted to be effective, recommending treatment of the subject.

Further provided herein are pharmaceutical compositions for treating a cancer in a subject. The pharmaceutical compositions comprise an IFN-I inhibiting agent comprising a JAK inhibitor, an SVV or an SVV derivative and a pharmaceutical acceptable carrier.

Also provided are Seneca Valley Virus (SVV) or SVV derivatives in combination with at least one IFN-I inhibiting agent comprising a JAK inhibitor for use in the manufacture of a medicament for treatment of a cancer, wherein the cancer is characterized by an expression level of anthrax toxin receptor 1 (ANTXR1) higher than an ANTXR1 reference value, and an expression level of interferon type I (IFN-I) lower than an IFN-I reference value.

Further provided herein are kits for determining a predisposition of an efficacious response to a cancer treatment comprising an Seneca Valley Virus (SVV), or an SVV derivative, combined with at least one IFN-I inhibiting agent comprising a JAK inhibitor. The kits comprise a reagent for determining the expression level of ANTXR1 and a reagent for determining the expression level of IFN-I in the cancer from a subject.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 19 is a table listing series of data predictions for cancer cell lines and their predicted status for permissive or non-permissive SVV replication.

DETAILED DESCRIPTION OF THE INVENTION

Figure 1:
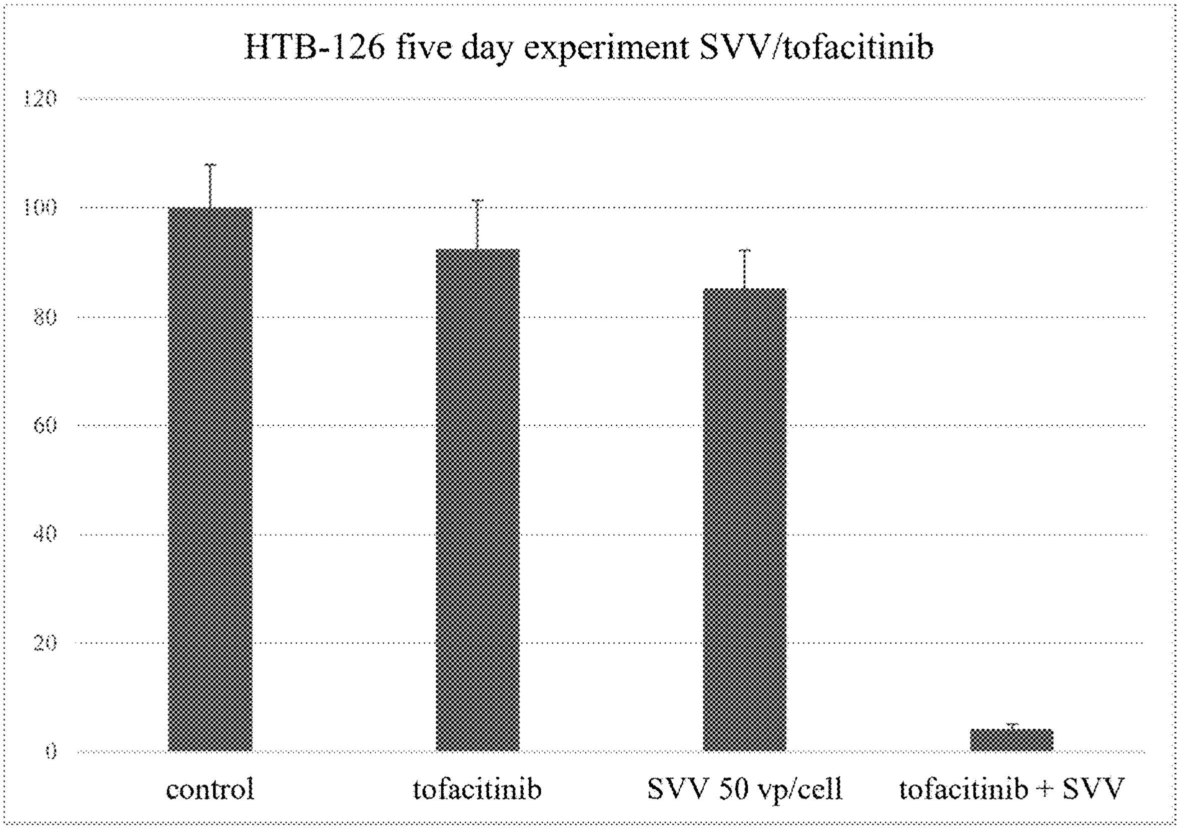
FIG. 1 is a histogram depicting an example of the use of a drug to modify susceptibility to virus mediated killing by Seneca Valley Virus (SVV). HTB-126 cells (triple negative breast cancer, TNBC) were pretreated for 24 hours in 12.5 micromolar tofacitinib then infected with 50 viral particles (VP) of SVV/cell. Standard deviations of replicates are presented as error bars (VP/cell with 1 PFU or TCID50 unit per 100 VPs).

The present invention relates to compositions and methods of using Seneca Valley Virus (SVV) or a derivative thereof for treating cancer in a subject. The SVV and SVV derivatives of the invention are useful in a variety of applications such as treating a cancer, reducing or inhibiting cancer cells growth, and increasing the survival of subject suffering from cancer. The disclosed methods particularly rely upon the level of an ANTXR1 expression and the level of IFN-I expression in a cancerous tissue from the subject. Also provided herein are methods for predicting the efficacy of an SVV treatment and a kit for determining the same.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein the terms anthrax toxin receptor 1 (ANTXR1) or Tumor Endothelial Marker 8 (TEM8), are used interchangeably. The protein encoded by ANTXR1 gene is a type I transmembrane protein. ANTXR1/TEM8 is a tumor-specific endothelial marker that has been implicated tumor vasculature formation of various cancers (e.g. colorectal).

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "biological" or "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

As used herein, the terms "comprising," "including," "containing" and "characterized by" are exchangeable, inclusive, open-ended and do not exclude additional, unrecited elements or method steps. Any recitation herein of the term "comprising," particularly in a description of components of a composition or in a description of elements of a device, is understood to encompass those compositions and methods consisting essentially of and consisting of the recited components or elements.

As used herein, the term "consisting of" excludes any element, step, or ingredient not specified in the claim element.

As used herein, the terms "derivative" specifies that a derivative of a virus can have a nucleic acid or amino acid sequence difference in respect to a template viral nucleic acid or amino acid sequence. For instance, an SVV derivative can refer to an SVV that has a nucleic acid or amino acid sequence different with respect to the wild-type SVV nucleic acid or amino acid sequence of ATCC Patent Deposit Number PTA-5343. In some embodiments, the SVV derivative encompasses an SVV mutant, an SVV variant or a modified SVV (e.g. genetically engineered SVV). In some embodiments, the modify SVV derivative is modified to be capable of recognizing different cell receptors or to be capable of evading the immune system while still being able to invade, replicate and kill the cell of interest (i.e. cancer cell). In general, an SVV or SVV derivative can be derived from an already pre-existing stock of virus that is passaged to produce more viruses. SVV or SVV derivative can also be derived from a plasmid.

As used herein, "higher" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween, than a control reference. A disclosed herein an expression level higher than a reference value refers to an expression level (mRNA or protein) that is higher than a normal or control level from an expression (mRNA or protein) measured in a healthy subject or defined or used in the art.

As used herein, "lower" refers to expression levels which are at least 10% lower or more, for example, 20%, 30%, 40%, or 50%, 60%, 70%, 80%, 90% lower or more, and/or 1.1 fold, 1.2 fold, 1.4 fold, 1.6 fold, 1.8 fold, 2.0 fold lower or more, and any and all whole or partial increments in between, than a control reference. A disclosed herein an expression level lower than a reference value refers to an expression level (mRNA or protein) that is lower than a normal or control level from an expression (mRNA or protein) measured in a healthy subject or defined or used in the art.

As used herein, the terms "control," or "reference" can be used interchangeably and refer to a value that is used as a standard of comparison.

As used herein, by "combination therapy" is meant that a first agent is administered in conjunction with another agent. "In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime.

The term "Type I interferon (IFN-I)" refers herein to interferon proteins or genes involved in regulating the activity of the immune system with antiviral, antitumor and immunoregulatory functions. As used herein, IFN-I includes any set of proteins, genes or transcripts that comprise or regulate the type I IFN pathway. Examples of IFN-I in mammals include but are not limited to IFN-α (alpha), IFN-β (beta), IFN-κ (kappa), IFN-δ (delta), IFN-ε (epsilon), IFN-τ (tau), IFN-ω (omega), and IFN-ζ (zeta). IFN-I biomarkers (mRNA or protein) may include various cytokines (interferons, interleukins or other growth factors). For instance, IFN-I biomarkers can comprise IFI35, IFN-α, IFN-β, IFN-κ, IFN-δ, IFN-ε, IFN-τ, IFN-ω, and IFN-ζ, ADAR, IRF9, IFITM3, IFITM2, USP18, LOC144383, EGR1, IFI6, GBP2, HLA-A, HLA-B, HLA-C, HLA-F, HLA-G, IRF8, IFI27, IFI35, IFIT2, IFIT1, IFIT3, IFNA1, IFNA2, IFNA4, IFNA5, IFNA6, IFNA7, IFNA8, IFNA10, IFNA14, IFNA16, IFNA17, IFNA21, IFNAR1, IFNAR2, IFNB1, IRF1, IRF2, IRF3, IRF4, IRF5, IRF6, IRF7, ISG20, JAK1, MX1, MX2, OAS1, OAS2, OAS3, IP6K2, XAF1, PSMB8, PTPN1, PTPN6, RNASEL, HLA-K, STAT1, STAT2, TYK2, HLA-B, IFITM1, OASL, SOCS1, SOCS3 and ISG15.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, plaque forming units (PFU) refers to a measure of number of infectious virus particles. It is determined by plaque forming assay.

As used herein, multiplicity of infection (MOI) refers the average number of virus particles infecting each cell. MOI can be related to PFU by the following formula:

Multiplicity of infection (MOI)=Plaque forming units (PFU) of virus used for infection/number of cells.

The term "RNA" as used herein is defined as ribonucleic acid.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intra-tumoral, intravenous, intrapleural, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the term "effective amount" or "therapeutically effective amount" means the amount of the virus particle or infectious units generated from vector of the invention which is required to prevent the particular disease condition, or which reduces the severity of and/or ameliorates the disease condition or at least one symptom thereof or condition associated therewith.

A "subject" or "patient," as used therein, may be a human or non-human mammal. Non-human mammals include, for example, livestock and pets, such as ovine, bovine, porcine, canine, feline and murine mammals. Preferably, the subject is a human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Provided herein are compositions and methods for treating a cancer in a subject based upon the expression level of an ANTXR1 and the expression level of IFN-I expression in the cancer from the subject.

Methods of the Invention

In one aspect, a method of treating a cancer in a subject in need thereof is disclosed herein. The method comprises administering an effective amount of Seneca Valley Virus (SVV) or SVV derivative, wherein the cancer is characterized by (a) an expression level of anthrax toxin receptor 1 (ANTXR1) higher than an ANTXR1 reference value, and (b) an expression level of interferon type I (IFN-I) lower than an IFN-I reference value.

In one aspect, another method of treating a cancer in a subject in need thereof is disclosed. The method comprises administering to the subject an IFN-I inhibiting agent and an effective amount of SVV or SVV derivative, wherein the cancer is characterized by an expression level of ANTXR1 higher than an ANTXR1 reference value, and wherein the IFN-I inhibiting agent reduces the expression level of IFN-I in the cancer thereby favoring replication of the SVV or SVV derivative and killing of the cancer.

In another aspect, also disclosed herein is a method of predicting the efficacy of an SVV or an SVV derivative treatment of a cancer in a subject in need thereof. The method comprises determining the expression level of ANTXR1 and the expression level of IFN-I in the cancer from the subject, wherein (a) an expression level of ANTXR1 higher than an ANTXR1 reference value, and (b) an expression level of IFN-I lower than an IFN-I reference value, are predictive that the treatment is effective, and wherein when the treatment is predicted to be effective, recommending treatment of the subject.

The treatment of cancer provided herein may include the treatment of solid tumors or the treatment of metastasis. Metastasis is a form of cancer wherein the transformed or malignant cells are traveling and spreading the cancer from one site to another. Such cancers include cancers of the skin, breast, brain, cervix, testes, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. Skin cancer includes malignant melanoma, basal cell carcinoma, squamous cell carcinoma, Karposi's sarcoma, moles dysplastic nevi, lipoma, angioma, dermatofibroma, keloids, and psoriasis.

In some embodiments, the cancer treated by the presently disclosed methods comprises a triple negative breast cancer, a small cell lung cancer, a non-small cell lung cancer, a non-small cell squamous carcinoma, an adenocarcinoma, a glioblastoma, a skin cancer, a hepatocellular carcinoma, a colon cancer, a cervical cancer, an ovarian cancer, an endometrial cancer, a neuroendocrine cancer, a pancreatic cancer, a thyroid cancer, a kidney cancer, a bone cancer, an oesophagus cancer or a soft tissue cancer.

Reference Value or Control

The methods provided herein include comparing a measured expression level of ANTXR1 or IFN-I in a cancer from a subject to a reference value (i.e. the control amount) of expression of ANTXR1 or IFN-I.

In one embodiment, the reference level of expression of ANTXR1 or IFN-I may be obtained by measuring the expression level of ANTXR1 or IFN-I in a healthy subject. Preferably, the healthy subject is a subject of similar age, gender and race and has never been diagnosed with any type of sever disease particularly any type of cancer.

In another embodiment, the reference value of expression of ANTXR1 or IFN-I is a value for expression of ANTXR1 or IFN-I that is accepted in the art. This reference value can be baseline value calculated for a group of subjects based on the average or mean values of ANTXR1 or IFN-I expression by applying standard statistically methods.

In one embodiment, the expression level is determined by a method selected from the group consisting of detecting mRNA of the gene, detecting a protein encoded by the gene, and detecting a biological activity of the protein encoded by the gene.

In certain aspects of the present invention, the expression level of ANTXR1 or IFN-I is determined in a cancerous sample from a subject. The sample preferably includes tumor cells, any fluid from the surrounding of tumor cells (e.g. leukemic blood, or tumor tissue) or any fluid that is in physiological contact or proximity with the tumor, or any other body fluid in addition to those recited herein should also be considered to be included herein.

Methods of Measurement

Any method known to those in the art can be employed for determining the expression level of ANTXR1, IFN-I and/or other biomarkers at the transcriptional or translational level. For example, a microarray can be used. Microarrays are known in the art and consist of a surface to which probes that correspond in sequence to gene products (e.g. mRNAs, polypeptides, fragments thereof etc.) can be specifically hybridized or bound to a known position. To detect at least one gene of interest, a hybridization sample is formed by contacting the test sample with at least one nucleic acid probe. A preferred probe for detecting ANTXR1 and/or IFN-I is a labeled nucleic acid probe capable of hybridizing to ANTXR1 and/or IFN-I mRNA(s). The nucleic acid probe can be, for example, a full-length nucleic acid molecule, or a portion thereof, such as an oligonucleotide of at least 10, 15, or 20 nucleotides in length and sufficient to specifically hybridize under stringent conditions to the appropriate target. The hybridization sample is maintained under conditions which are sufficient to allow specific hybridization of the nucleic acid probe to a target of interest. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe and a gene in the test sample, the sequence that is present in the nucleic acid probe is also present in the mRNA of the subject. More than one nucleic acid probe can also be used. Hybridization intensity data detected by the scanner are automatically acquired and processed by the Affymetrix Microarray Suite (MASS) software. Raw data is normalized to expression levels using a target intensity of 150. An alternate method to measure mRNA expression profiles of a small number of different genes is by e.g. either classical TaqMan® Gene Expression Assays or TaqMan® Low Density Array-micro fluidic cards (Applied Biosystems). Particularly, this invention preferably utilizes a qPCR system. Non-limiting examples include commercial kits such as the PrimePCRPathways® commercially available from Bio-rad (Berkley, California).

The transcriptional state of a sample, particularly mRNAs, may also be measured by other nucleic acid expression technologies known in the art. mRNA can be isolated from the sample using any method known to those in the art. Non-limiting examples include commercial kits, such as the RNeasy® commercially available from Qiagen (Netherlands) or the Mini Kit the TRI Reagent® commercially available from Molecular Research Center, Inc. (Cincinnati, Ohio), can be used to isolate RNA. Generally, the isolated mRNA may be amplified using methods known in the art. Amplification systems utilizing, for example, PCR or RT-PCR methodologies are known to those skilled in the art. For a general overview of amplification technology, see, for example, Dieffenbach et al., PCR Primer: A Laboratory Manual, Cold Spring Harbor Laboratory Press, New York (1995).

Another accurate method for profiling mRNA expression can the use of Next Generation Sequencing (NGS) including first, second, third as well as subsequent Next Generations Sequencing technologies.

In other aspects provided herein, determining the amount or detecting the biological activity of a peptide, polypeptide can be achieved by all known means in the art for determining the amount of a peptide or polypeptide in a sample. These means comprise immunoassay devices and methods which may utilize labeled molecules in various sandwich, competition, or other assay formats. Such assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. These methods comprise, preferably, biosensors, optical devices coupled to immunoassays, biochips, analytical devices such as mass-spectrometers, NMR-analyzers, HPLC, FPLC, or chromatography devices. Further, methods include, Western blots, micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

In some embodiments, for the various methods disclosed herein, the expression level of ANTXR1 is determined based on the level of an ANTXR1 mRNA or an ANTXR1 protein and the expression level of IFN-I is determined based on the level of an IFN-I biomarker mRNA or an IFN-I biomarker protein. In one embodiment, the IFN-I biomarker mRNA or IFN-I biomarker protein is at least one mRNA or protein selected from the group consisting of IFI35, IFN-α, IFN-β, IFN-κ, IFN-δ, IFN-ε, IFN-τ, IFN-ω, and IFN-ζ, ADAR, IRF9, IFITM3, IFITM2, USP18, LOC144383, EGR1, IFI6, GBP2, HLA-A, HLA-B, HLA-C, HLA-F, HLA-G, IRF8, IFI27, IFI35, IFIT2, IFIT1, IFIT3, IFNA1, IFNA2, IFNA4, IFNA5, IFNA6, IFNA7, IFNA8, IFNA10, IFNA14, IFNA16, IFNA17, IFNA21, IFNAR1, IFNAR2, IFNB1, IRF1, IRF2, IRF3, IRF4, IRF5, IRF6, IRF7, ISG20, JAK1, MX1, MX2, OAS1, OAS2, OAS3, IP6K2, XAF1, PSMB8, PTPN1, PTPN6, RNASEL, HLA-K, STAT1, STAT2, TYK2, HLA-B, IFITM1, OASL, SOCS1, SOCS3 and ISG15. In another embodiment, the IFN-I biomarker mRNA or IFN-I biomarker protein is IFI35 mRNA or IFI35 protein.

Combination Therapies

The compositions and methods for treating a cancer in a subject using SVV or SVV derivatives described herein may be useful when combined with at least one additional compound useful for treating cancer. The additional compound may comprise a commercially available compound, known to treat, prevent, or reduce the symptoms of cancer and/or metastasis.

In one aspect, the pharmaceutical composition disclosed herein may be used in combination with a therapeutic agent such as an anti-tumor agent, including but not limited to a chemotherapeutic agent, an anti-cell proliferation agent or any combination thereof. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents. In another aspect, the pharmaceutical composition disclosed herein may be used in combination with a radiation therapy.

Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include aclacinomycin, actinomycin, anthramycin, azaserine, bleomycins, cactinomycin, calicheamicin, carubicin, caminomycin, carzinophilin, chromomycin, dactinomycin, daunorubicin, detorubicin, 6-diazo-5-oxo-L-norleucine, doxorubicin, epirubicin, esorubicin, idarubicin, marcellomycin, mitomycins, mitoxantrone, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Miscellaneous agents include chemotherapeutics such as bleomycin, hydroxyurea, L-asparaginase, and procarbazine.

Other examples of chemotherapeutic agents include, but are not limited to, the following and their pharmaceutically acceptable salts, acids and derivatives: MEK inhibitors, such as but not limited to, refametinib, selumetinib, trametinib or cobimetinib; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone;

aldophosphamide glycoside; aminolevulinic acid; amsacrine; bestrabucil; bisantrene; edatrexate; defofamine; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K (PSK); razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOLO, Bristol-Myers Squibb Oncology, Princeton, N.J.) and docetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

An immunotherapeutic agent may be, but is not limited to, an interleukin-2 or other cytokine, an inhibitor of programmed cell death protein 1 (PD-1) signaling such as a monoclonal antibody that binds to PD-1, Ipilimumab. The immunotherapeutic agent can also block cytotoxic T lymphocytes associated antigen A-4 (CTLA-4) signaling and it can also relate to cancer vaccines and dendritic cell-based therapies.

In one embodiment the subject suffering from cancer is administered at least one anti-cancer therapeutic agent selected from the group consisting of: a checkpoint inhibitor, a PD-1 inhibitor, a PD-L1 inhibitor, a CTLA-4 inhibitor, a cytokine, a growth factor, a photosensitizing agent, a toxin, a siRNA molecule, a signaling modulator, an anti-cancer antibiotic, an anti-cancer antibody, an angiogenesis inhibitor, a chemotherapeutic compound, anti-metastatic compound, an immunotherapeutic compound, a CAR therapy, a dendritic cell-based therapy, a cancer vaccine, an oncolytic virus, an engineered anti-cancer virus or virus derivative and a combination of any thereof. In one embodiment, the least one anti-cancer therapeutic agent is administered formerly, simultaneously or subsequently to the administering of the SVV or SVV derivative.

In one embodiment, the subject is administered an IFN-I inhibiting agent. The IFN-I inhibiting agent used herein encompasses any agent known in the art for inhibiting, suppressing or reducing partially or fully and temporarily or permanently IFN type I pathway.

The inhibiting agent comprises siRNA, ribozyme, an antisense molecule, an aptamer, a peptidomimetic, a small molecule, histone deacetylase (HDAC) inhibitor, Janus kinase (JAK) inhibitor, IFN inhibitor, IFN antibody, IFN-α Receptor 1 antibody, IFN-α Receptor 2 antibody and viral peptide and a combination of any thereof. The viral peptide can be, but not limited to, NS1 protein from an Influenza virus or NS2B3 protease complex from dengue virus.

A large number of HDAC inhibitors are known and used in the art. The most common HDAC inhibitors bind to the zinc-containing catalytic domain of the HDACs. These HDAC inhibitors can be classified into several groupings named according to their chemical structure and the chemical moiety that binds to the zinc ion. Some examples include, but are not limited to, hydroxamic acids or hydroxamates (such as Trichostatin A or Vorinostat/SAHA (FDA approved)), aminobenzamides Entinostat (MS-275), Tacedinaline (CI994), and Mocetinostat (MGCD0103), cyclic peptides (Apicidin, Romidepsin (FDA approved)), cyclic tetrapeptides or epoxyketones (such as Trapoxin B), depsipeptides, benzamides, electrophilic ketones, and carboxylic aliphatic acid compounds (such as butyrate, phenylbutyrate, valproate and valproic acid). Other HDAC inhibitors include, but are not limited not, Belinostat (PXD101), LAQ824, and Panobinostat (LBH589). Examples of HDCA inhibitors in clinical trials include Panobinostat (LBH-589), Belinostat (PXD101), Entinostat (MS275), Mocetinostat (MGCD01030), Givinostat (ITF2357), Practinostat (SB939), Chidamide (CS055/HBI-8000), Quisinostat (JNJ-26481585), Abexinostat (PCI-24781), CHR-3996 and AR-Z2.

JAK inhibitors inhibit the activity of one or more of the Janus kinase family of enzymes (e.g. JAK1, JAK2, JAK3 and/or TYK2), thereby interfering with the JAK-STAT signaling pathway. Various JAK inhibitors are known and used in the art for the treatment of inflammatory diseases or cancer. Non-limiting examples of JAK inhibitors are FDA approved compounds including Ruxolitinib (Jakafi/Jakavi), Tofacitinib (Jakvinus, formerly known as tasocitinib and CP-690550), Oclacitinib (Apoquel), Baricitinib (Olumiant, LY3009104), Decernotinib (VX-509). Other JAK inhibitors are under clinical trials and/or used as experimental drugs. These include for instance Filgotinib (G-146034, GLPG-0634), Cerdulatinib (PRT062070), Gandotinib (LY-2784544), Lestaurtinib (CEP-701), Momelotinib (GS-0387, CYT-387), Pacritinib (SB1518), PF-04965842, Upadacitinib (ABT-494), Peficitinib (ASP015K, JNJ-54781532), Fedratinib (SAR302503), Cucurbitacin I, CHZ868, ABT-494, dimethyl fumarate (DMF, Tecfidera), GLPG0634, and CEP-33779.

In one embodiment, the subject is administered at least one IFN-I inhibiting agent selected from the group consisting of: HDAC inhibitor, JAK inhibitor, IFN inhibitor, IFN antibody, IFN-α Receptor 1 antibody, IFN-α Receptor 2 antibody and viral peptide and a combination of any thereof. In another embodiment, the at least one IFN-I inhibiting agent is administered formerly, simultaneously or subsequently to the administering of the SVV or SVV derivative. In some embodiments, the at least one IFN-I inhibiting agent is subsequently removed once the SVV has replicated in the tumor cells and before the addition of an anti-cancer therapeutic agent (e.g. checkpoint inhibitor).

In one embodiment, the anti-cancer therapeutic agent is administered formerly, simultaneously or subsequently to the administering of the at least one IFN-I inhibiting agent. In one embodiment, the anti-cancer therapeutic agent is administered subsequently to the administering of the at least one IFN-I inhibiting agent. In another embodiment, the anti-cancer therapeutic agent is administered subsequently to the administering of the at least one IFN-I inhibiting agent and the SVV or SVV derivative.

In one embodiment the SVV or SVV derivative treatment is preceded by the administration of IFN-I inhibiting agent. In one embodiment, once SVV replication and cancer cells death are confirmed, the administration of IFN-I inhibiting agent is terminated. For instance, cancer cells can be treated with an IFN-I inhibitor, (e.g. (5-(tetradecyloxy)-2-furoic acid), acetyl-CoA carboxylase inhibitor: TOFA), 24 hours before SVV treatment and then both treatments can be pursued for several weeks until robust SVV replication is observed and markers of cell death are detected. Then the treatment with IFN-I inhibiting agent can be terminated and an anti-cancer therapeutic agent (such as but not limited to a checkpoint inhibitor, a PD-1 inhibitor, a PD-L1 inhibitor or a CTLA-4 inhibitor) can be initiated. Upon SVV replication, various nucleic acids and cellular debris are generated which can trigger the activation of an influx of immune cells (e.g. T-cells, NK, cells, APCs, etc.) to proceed in cancer cells killing and this process of immune response is enhanced further by the termination of IFN-I inhibition.

Pharmaceutical Compositions and Formulations.

Also provided herein is the use of a pharmaceutical composition comprising an SVV or an SVV derivative depleting agent for use in the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment provided herein, the pharmaceutical composition useful for practicing the method of the invention may be administered to deliver a dose of between 1 ng/kg/day and 100 mg/kg/day. In another embodiment, the pharmaceutical composition useful for practicing the invention may be administered to deliver a dose of between 1 ng/kg/day and 500 mg/kg/day. The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. In some embodiments, the SVV or derivative thereof can be formulated in a natural capsid, a modified capsid, as a naked RNA, or encapsulated in a protective coat.

The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs. In one embodiment, the subject is a human or a non-human mammal such as but not limited to an equine, an ovine, a bovine, a porcine, a canine, a feline and a murine. In one embodiment, the subject is a human.

In one embodiment, the compositions are formulated using one or more pharmaceutically acceptable excipients or carriers. In one aspect a pharmaceutical composition is disclosed for treating a cancer in a subject. The pharmaceutical composition comprises an IFN-I inhibiting agent, an SVV or an SVV derivative and a pharmaceutical acceptable carrier. Pharmaceutically acceptable carriers, which are useful, include, but are not limited to, glycerol, water, saline, ethanol and other pharmaceutically acceptable salt solutions such as phosphates and salts of organic acids. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The disclosed composition may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition may include an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Administration/Dosing

The regimen of administration may affect what constitutes an effective amount. For example, the therapeutic formulations may be administered to the patient subject either prior to or after a surgical intervention related to cancer, or shortly after the patient was diagnosed with cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient subject, preferably a mammal, more preferably a human, may be carried out using known procedures, at dosages and for periods of time effective to treat cancer in the subject. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day.

The compound can be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient. A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

Routes of Administration

One skilled in the art will recognize that although more than one route can be used for administration, a particular route can provide a more immediate and more effective reaction than another route.

Routes of administration of the disclosed compositions include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration. Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein. In one embodiment, the SVV or SVV derivative treatment comprises an administration route selected from the group consisting of inhalation, oral, rectal, vaginal, parenteral, topical, transdermal, pulmonary, intranasal, buccal, ophthalmic, intra-hepatic arterial, intrapleural, intrathecal, intra-tumoral, intravenal and any combination thereof.

In yet another aspect, also provided herein is a kit for determining a predisposition of an efficacious response to an SVV or an SVV derivative based treatment of a cancer in a subject, the kit comprising a reagent for determining the expression level of ANTXR1 and a reagent for determining the expression level of IFN-I in the cancer from the subject.

Kit

The invention includes a set of preferred oligomers or antibodies, either labeled (e.g., fluorescer, quencher, etc.) or unlabeled, that are useful for the detection of at least ANTXR1 and/or IFN-I.

In certain embodiments, a kit is provided. Commercially available kits for use in these methods are, in view of this specification, known to those of skill in the art. In general, kits will comprise a detection reagent that is suitable for detecting the presence of a polypeptide or nucleic acid, or mRNA of interest.

In another embodiment, there is a panel of probe sets or antibodies. Preferred probe sets are designed to detect the expression level of ANTXR1 and/or IFN-I and provide information about the efficacy of an SVV or an SVV derivative based cancer treatment. Probe sets are particularly useful because they are smaller and cheaper than probe sets that are intended to detect as many polynucleotides or peptides as possible in a particular genome. As provided herein, the probe sets are targeted at the detection of polynucleotides or polypeptides that are informative about ANTXR1 and/or IFN-I in cancer cells or tissues. Probe sets may also comprise a large or small number of probes that detect polynucleotides or peptides that are not informative about cancer. Such probes are useful as controls and for normalization (e.g., spiked-in markers). Probe sets may be a dry mixture or a mixture in solution. In some embodiments, probe sets can be affixed to a solid substrate to form an array of probes. The probes may be antibodies, or nucleic acids (e.g., DNA, RNA, chemically modified forms of DNA and RNA), LNAs (Locked nucleic acids), or PNAs (Peptide nucleic acids), or any other polymeric compound capable of specifically interacting with the peptides or nucleic acid sequences of interest.

It is contemplated that kits may be designed for isolating and/or detecting peptides (e.g. ANTXR1, know cancer markers, immune activators or apoptotic proteins) or nucleic acid sequences in essentially any sample (e.g., leukemic blood, tumor cells, tumor tissue, etc. . . . ), and a wide variety of reagents and methods are, in view of this specification, known in the art.

In further embodiments a kit is provided for treating or ameliorating a cancer, as described elsewhere herein wherein the kit comprises: a) a compound or compositions as described herein; and b) an additional agent or therapy as described herein. The kit can further include instructions or a label for using the kit to treat or ameliorate the cancer. In yet other embodiments, the invention extends to kits assays for a given cancer (such as, but not limited to, small-cell lung cancer or triple negative breast cancer), as described herein. Such kits may, for example, contain the reagents from PCR or other nucleic acid hybridization technology (microarrays) or reagents for immunologically based detection techniques (e.g., ELISpot, ELISA).

ILLUSTRATIVE EMBODIMENTS

Provided here are illustrative embodiments of the disclosed technology. These embodiments are illustrative only and do not limit the scope of the present disclosure or of the claims attached Embodiment 1. A method of treating a cancer in a subject in need thereof, the method comprising administering to the subject an effective amount of Seneca Valley Virus (SVV) or SVV derivative, wherein the cancer is characterized by: an expression level of anthrax toxin receptor 1 (ANTXR1) higher than an ANTXR1 reference value, and an expression level of interferon type I (IFN-I) lower than an IFN-I reference value, wherein the subject is also administered at least one IFN-I inhibiting comprising a JAK inhibitor.

Embodiment 2. The method of embodiment 1, wherein the expression level of ANTXR1 is determined based on the level of an ANTXR1 mRNA or an ANTXR1 protein.

Embodiment 3. The method of embodiment 1, wherein the expression level of IFN-I is determined based on the level of an IFN-I biomarker mRNA or an IFN-I biomarker protein.

Embodiment 4. The method of embodiment 3, wherein the IFN-I biomarker mRNA or IFN-I biomarker protein is at least one mRNA or protein selected from the group consisting of IFI35, IFN-α, IFN-β, IFN-κ, IFN-δ, IFN-ε, IFN-τ, IFN-ω, and IFN-ζ, ADAR, IRF9, IFITM3, IFITM2, USP18, LOC144383, EGR1, IFI6, GBP2, HLA-A, HLA-B, HLA-C, HLA-F, HLA-G, IRF8, IFI27, IFI35, IFIT2, IFIT1, IFIT3, IFNA1, IFNA2, IFNA4, IFNA5, IFNA6, IFNA7, IFNA8, IFNA10, IFNA14, IFNA16, IFNA17, IFNA21, IFNAR1, IFNAR2, IFNB1, IRF1, IRF2, IRF3, IRF4, IRF5, IRF6, IRF7, ISG20, JAK1, MX1, MX2, OAS1, OAS2, OAS3, IP6K2, XAF1, PSMB8, PTPN1, PTPN6, RNASEL, HLA-K, STAT1, STAT2, TYK2, HLA-B, IFITM1, OASL, SOCS1, SOCS3 and ISG15.

Embodiment 5. The method of embodiment 3, wherein the IFN-I biomarker mRNA or IFN-I biomarker protein is IFI35 mRNA or IFI35 protein.

Embodiment 6. The method of embodiment 1, wherein the subject is administered at least one anti-cancer therapeutic agent selected from the group consisting of: a checkpoint inhibitor, a PD-1 inhibitor, a PD-L1 inhibitor, a CTLA-4 inhibitor, a cytokine, a growth factor, a photosensitizing agent, a toxin, a siRNA molecule, a signaling modulator, an anti-cancer antibiotic, an anti-cancer antibody, an angiogenesis inhibitor, a chemotherapeutic compound, anti-metastatic compound, an immunotherapeutic compound, a CAR therapy, a dendritic cell-based therapy, a cancer vaccine, an oncolytic virus, an engineered anti-cancer virus or virus derivative and a combination of any thereof.

Embodiment 7. The method of embodiment 5, wherein the least one anti-cancer therapeutic agent is administered formerly, simultaneously or subsequently to the administering of the SVV.

Embodiment 8. The method of embodiment 1, wherein the least one IFN-I inhibiting agent comprises an HDAC inhibitor, an IFN inhibitor, an IFN antibody, an IFN-α Receptor 1 antibody, an IFN-α Receptor 2 antibody, a viral peptide or a combination of any thereof.

Embodiment 9. The method of embodiment 8, wherein the least one IFN-I inhibiting agent is administered formerly, simultaneously or subsequently to the administering of the SVV.

Embodiment 10. The method of embodiment 1, wherein the administering comprises an administration route is selected from the group consisting of inhalation, oral, rectal, vaginal, parenteral, topical, transdermal, pulmonary, intranasal, buccal, ophthalmic, intra-hepatic arterial, intrathecal, intra-tumoral, intravenal and any combination thereof.

Embodiment 11. The method of embodiment 1, wherein the cancer comprises a triple negative breast cancer, a small cell lung cancer, a non-small cell lung cancer, a non-small cell squamous carcinoma, an adenocarcinoma, a glioblastoma, a skin cancer, a hepatocellular carcinoma, a colon cancer, a cervical cancer, an ovarian cancer, an endometrial cancer, a neuroendocrine cancer, a pancreatic cancer, a thyroid cancer, a kidney cancer, a bone cancer, an oesophagus cancer or a soft tissue cancer.

Embodiment 12. A method of treating a cancer in a subject in need thereof, the method comprising administering to the subject an IFN-I inhibiting agent comprising a JAK inhibitor and an effective amount of SVV or SVV derivative, wherein the cancer is characterized by an expression level of ANTXR1 higher than an ANTXR1 reference value, and wherein the IFN-I inhibiting agent reduces the expression level of IFN-I in the cancer thereby favoring replication of the SVV or the SVV derivative and killing of the cancer.

Embodiment 13. The method of embodiment 12, wherein the IFN-I inhibiting agent comprises an MAC inhibitor, an IFN inhibitor, an IFN antibody, an IFN-α Receptor 1 antibody, an IFN-α Receptor 2 antibody, a viral peptide or a combination of any thereof.

Embodiment 14. The method of embodiment 12, wherein the IFN-I inhibiting agent is administered formerly, simultaneously or subsequently to the administering of the SVV.

Embodiment 15. The method of embodiment 12, wherein the expression level of ANTXR1 is determined based on the level of an ANTXR1 mRNA or an ANTXR1 protein.

Embodiment 16. The method of embodiment 12, wherein the expression level of IFN-I is determined based on the level of an IFN-I biomarker mRNA or an IFN-I biomarker protein.

Embodiment 17. The method of embodiment 16, wherein the IFN-I biomarker mRNA or IFN-I biomarker protein is at least one mRNA or protein selected from the group consisting of IFI35, IFN-α, IFN-β, IFN-κ, IFN-δ, IFN-ε, IFN-ω, and IFN-ζ, ADAR, IRF9, IFITM3, IFITM2, USP18, LOC144383, EGR1, IFI6, GBP2, HLA-A, HLA-B, HLA-C, HLA-F, HLA-G, IRF8, IFI27, IFI35, IFIT2, IFIT1, IFIT3, IFNA1, IFNA2, IFNA4, IFNA5, IFNA6, IFNA7, IFNA8, IFNA10, IFNA14, IFNA16, IFNA17, IFNA21, IFNAR1, IFNAR2, IFNB1, IRF1, IRF2, IRF3, IRF4, IRF5, IRF6, IRF7, ISG20, JAK1, MX1, MX2, OAS1, OAS2, OAS3, IP6K2, XAF1, PSMB8, PTPN1, PTPN6, RNASEL, HLA-K, STAT1, STAT2, TYK2, HLA-B, IFITM1, OASL, SOCS1, SOCS3 and ISG15.

Embodiment 18. The method of embodiment 16, wherein the IFN-I biomarker mRNA or IFN-I biomarker protein is IFI35 mRNA or IFI35 protein.

Embodiment 19. The method of embodiment 12, wherein the subject is administered at least one anti-cancer therapeutic agent selected from the group consisting of: a checkpoint inhibitor, a PD-1 inhibitor, a PD-L1 inhibitor, a CTLA-4 inhibitor, a cytokine, a growth factor, a photosensitizing agent, a toxin, a siRNA molecule, a signaling modulator, an anti-cancer antibiotic, an anti-cancer antibody, an angiogenesis inhibitor, a chemotherapeutic compound, anti-metastatic compound, an immunotherapeutic compound, a CAR therapy, a dendritic cell-based therapy, a cancer vaccine, an oncolytic virus, an engineered anti-cancer virus or virus derivative a combination of any thereof.

Embodiment 20. The method of embodiment 18, wherein the least one anti-cancer therapeutic agent is administered formerly, simultaneously or subsequently to the administering of the IFN-I inhibiting agent and SVV.

Embodiment 21. The method of embodiment 12, wherein the administering comprises an administration route is selected from the group consisting of inhalation, oral, rectal, vaginal, parenteral, topical, transdermal, pulmonary, intranasal, buccal, ophthalmic, intra-hepatic arterial, intrathecal, intra-tumoral, intravenal and any combination thereof.

Embodiment 22. The method of embodiment 12, wherein the cancer comprises a triple negative breast cancer, a small cell lung cancer, a non-small cell lung cancer, a non-small cell squamous carcinoma, an adenocarcinoma, a glioblastoma, a skin cancer, a hepatocellular carcinoma, a colon cancer, a cervical cancer, an ovarian cancer, an endometrial cancer, a neuroendocrine cancer, a pancreatic cancer, a thyroid cancer, a kidney cancer, a bone cancer, an oesophagus cancer or a soft tissue cancer.

Embodiment 23. A method of predicting the efficacy of a cancer treatment comprising an Seneca Valley Virus (SVV), or an SVV derivative, combined with at least one IFN-I inhibiting agent comprising a JAK inhibitor, the method comprising determining the expression level of ANTXR1 and the expression level of IFN-I in the cancer from a subject, wherein: an expression level of ANTXR1 higher than an ANTXR1 reference value, and an expression level of IFN-I lower than an IFN-I reference value are predictive that the treatment is effective, and wherein when the treatment is predicted to be effective, recommending treatment of the subject.

Embodiment 24. The method of embodiment 23, wherein the expression level of ANTXR1 is determined based on the level of an ANTXR1 mRNA or an ANTXR1 protein.

Embodiment 25. The method of embodiment 23, wherein the expression level of IFN-I is determined based on the level of an IFN-I biomarker mRNA or an IFN-I biomarker protein.

Embodiment 26. The method of embodiment 25, wherein the IFN-I biomarker mRNA or IFN-I biomarker protein is at least one mRNA or protein selected from the group consisting of IFI35, IFN-α, IFN-β, IFN-κ, IFN-δ, IFN-ε, IFN-τ, IFN-ω, and IFN-ζ, ADAR, IRF9, IFITM3, IFITM2, USP18, LOC144383, EGR1, IFI6, GBP2, HLA-A, HLA-C, HLA-F, HLA-G, IRF8, IFI27, IFI35, IFIT2, IFIT1, IFIT3, IFNA1, IFNA2, IFNA4, IFNA5, IFNA6, IFNA7, IFNA8, IFNA10, IFNA14, IFNA16, IFNA17, IFNA21, IFNAR1, IFNAR2, IFNB1, IRF1, IRF2, IRF3, IRF4, IRF5, IRF6, IRF7, ISG20, JAK1, MX1, MX2, OAS1, OAS2, OAS3, IP6K2, XAF1, PSMB8, PTPN1, PTPN6, RNASEL, STAT1, STAT2, TYK2, HLA-B, IFITM1, OASL, SOCS1, SOCS3 and ISG15.

Embodiment 27. The method of embodiment 25, wherein the IFN-I biomarker mRNA or IFN-I biomarker protein is IFI35 mRNA or IFI35 protein.

Embodiment 28. The method of embodiment 23, wherein the SVV or SVV derivative treatment further comprises a treatment with at least one anti-cancer therapeutic agent selected from the group consisting of: a checkpoint inhibitor, a PD-1 inhibitor, a PD-L1 inhibitor, a CTLA-4 inhibitor, a cytokine, a growth factor, a photosensitizing agent, a toxin, a siRNA molecule, a signaling modulator, an anti-cancer antibiotic, an anti-cancer antibody, an angiogenesis inhibitor, a chemotherapeutic compound, anti-metastatic compound, an immunotherapeutic compound, a CAR therapy, a dendritic cell-based therapy, a cancer vaccine, an oncolytic virus, an engineered anti-cancer virus or virus derivative and a combination of any thereof.

Embodiment 29. The method of embodiment 27, wherein the treatment with at least one anti-cancer therapeutic agent is performed formerly, simultaneously or subsequently to the SVV or SVV derivative treatment.

Embodiment 30. The method of embodiment 23, wherein the at least one IFN-I inhibiting agent comprises an MAC inhibitor, a JAK inhibitor, an IFN inhibitor, an IFN antibody, an IFN-α Receptor 1 antibody, an IFN-α Receptor 2 antibody, a viral peptide or a combination of any thereof.

Embodiment 31. The method of embodiment 30, wherein the least one IFN-I inhibiting agent is administered formerly, simultaneously or subsequently to the SVV or SVV derivative treatment.

Embodiment 32. The method of embodiment 23, wherein SVV or SVV derivative treatment comprises an administration route selected from the group consisting of inhalation, oral, rectal, vaginal, parenteral, topical, transdermal, pulmonary, intranasal, buccal, ophthalmic, intra-hepatic arterial, intrathecal, intra-tumoral, intravenal and any combination thereof.

Embodiment 33. The method of embodiment 23, wherein the cancer comprises a triple negative breast cancer, a small cell lung cancer, a non-small cell lung cancer, a non-small cell squamous carcinoma, an adenocarcinoma, a glioblastoma, a skin cancer, a hepatocellular carcinoma, a colon cancer, a cervical cancer, an ovarian cancer, an endometrial cancer, a neuroendocrine cancer, a pancreatic cancer, a thyroid cancer, a kidney cancer, a bone cancer, an oesophagus cancer or a soft tissue cancer.

Embodiment 34. A pharmaceutical composition for treating a cancer in a subject, the pharmaceutical composition comprising an IFN-I inhibiting agent comprising a JAK inhibitor, an SVV or an SVV derivative and a pharmaceutical acceptable carrier.

Embodiment 35. The composition of embodiment 34, wherein the IFN-I inhibiting agent is at least one agent selected from the group consisting of: HDAC inhibitor, JAK inhibitor, IFN inhibitor, IFN antibody, IFN-α Receptor 1 antibody, IFN-α Receptor 2 antibody and viral peptide and a combination of any thereof.

Embodiment 36. The composition of embodiment 34, further comprises at least one anti-cancer therapeutic agent selected from the group consisting of: a checkpoint inhibitor, a PD-1 inhibitor, a PD-L1 inhibitor, a CTLA-4 inhibitor, a cytokine, a growth factor, a photosensitizing agent, a toxin, a siRNA molecule, a signaling modulator, an anti-cancer antibiotic, an anti-cancer antibody, an angiogenesis inhibitor, a chemotherapeutic compound, anti-metastatic compound, an immunotherapeutic compound, a CAR therapy, a dendritic cell-based therapy, a cancer vaccine, an oncolytic virus, an engineered anti-cancer virus or virus derivative and a combination of any thereof.

Embodiment 37. The composition of embodiment 34, wherein the cancer comprises a triple negative breast cancer, small cell lung cancer, a non-small squamous cell carcinoma, a skin cancer, a hepatocellular carcinoma, a colon cancer, a cervical cancer, an ovarian cancer, an endometrial cancer, a pancreatic cancer, a thyroid cancer, a kidney cancer, a bone cancer, an oesophagus cancer or a soft tissue cancer.

Embodiment 38. A kit for determining a predisposition of an efficacious response to a cancer treatment comprising an Seneca Valley Virus (SVV), or an SVV derivative, combined with at least one IFN-I inhibiting agent comprising a JAK inhibitor, the kit comprising a reagent for determining the expression level of ANTXR1 and a reagent for determining the expression level of IFN-I in the cancer from a subject.

Embodiment 39. The method or kit of any one of embodiments 1, 12, 23, 34 and 38, wherein the subject is a human.

Embodiment 40. A Seneca Valley Virus (SVV) or SVV derivative in combination with at least one IFN-I inhibiting agent comprising a JAK inhibitor for use in the manufacture of a medicament for treatment of a cancer, wherein the cancer is characterized by an expression level of anthrax toxin receptor 1 (ANTXR1) higher than an ANTXR1 reference value, and an expression level of interferon type I (IFN-I) lower than an IFN-I reference value.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Importance of ANTXR1 Receptor and IFN Type I Immune Pathway for SVV Replication Immunotherapies, including oncolytic virus therapies alone or in combination with agents known to modulate the tumor microenvironment, are revolutionizing the treatment of cancer, making treatments possible for incurable, hard to target and/or aggressive cancers. The antitumor activity of oncolytic viruses is a consequence of virus associated immunogenic cell death and induction of an immune response against tumor specific antigens.

Identification and description of ANTXR1/TEM 8 as the cellular receptor for the oncolytic virus SVV in combination with its discrete absence from the surface of normal healthy cells and presence on the surface of tumor cells and cells within the immediate surrounding environment, makes SVV an ideal candidate for the development of oncolytic virus immunotherapy.

Genomic analysis of the 42 ANTXR1/TEM $8^+$ cell lines refractory to SVV infection revealed robust expression of RNAs encoding components of the innate immune response. These data suggest that IFN type I (IFN-I) pathway modulates tropism of SVV infection (Miles et al., J Clin Invest. 2017; 127(8):2957-2967).

Several histone deacetylases inhibitors (HDACis) have been approved by the FDA for the treatment of cutaneous/peripheral T-cell lymphomas, hematological malignancies and solid tumors Impairing of IFN type I immune pathway will allow for controlled SVV replication in these cells. The amount of IFN-I inhibitor used for impairing the IFN-I pathway may allow maximal replication of SVV and IFN-I inhibition may be reversible upon removal of IFN-I inhibitor.

Figure 6:
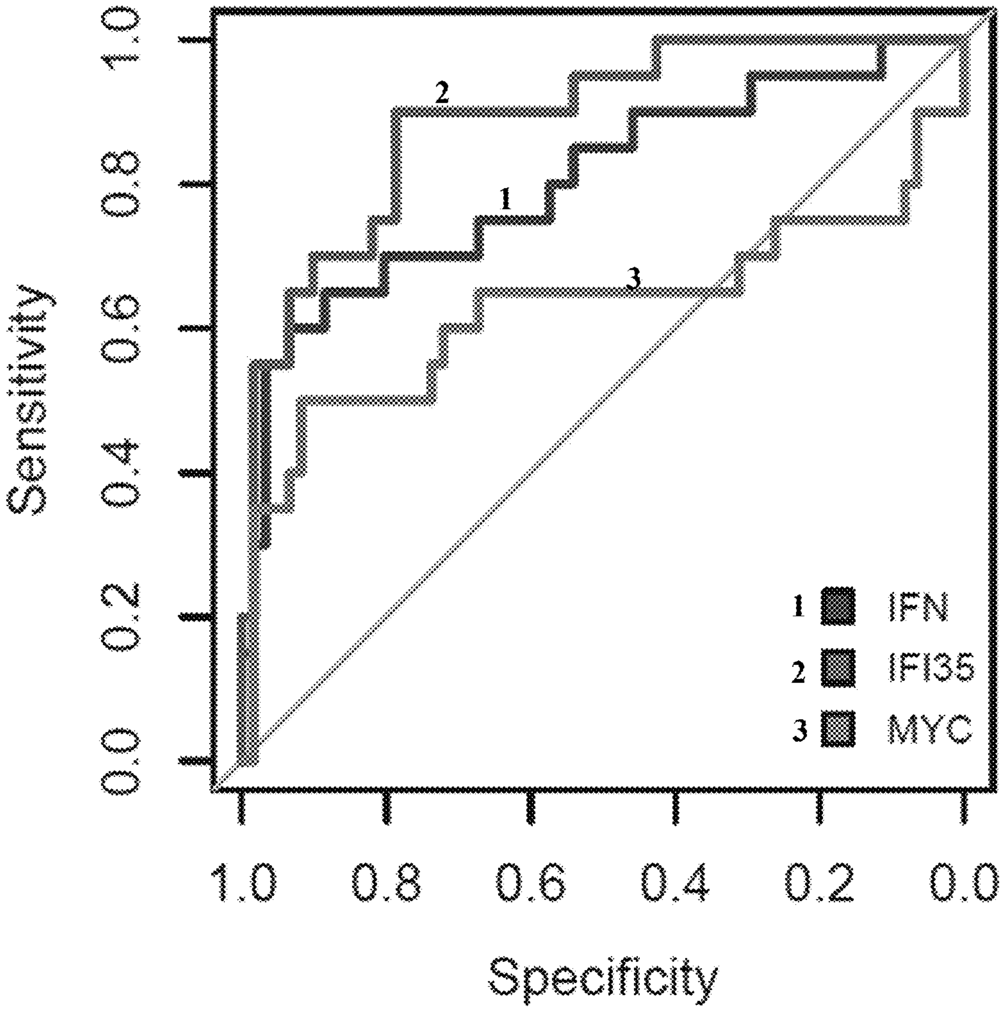
FIG. 6 is a plot representing a receiver operating characteristic curve (ROC) for an elastic net minimization of predictive genes set (IFN, Myc and IFI35). In order to identify a minimal predictive gene set, an elastic net was used. Area under the curve (AUC) of the receiver operating characteristic was calculated across a range of tuning parameters, lambda, which controls the overall strength of the elastic net penalty. Mean AUC was calculated using 6-fold cross validation (reads points). Uncertainty is expressed as standard deviation. Vertical dashed lines indicate the optimal values of lambda that give either the minimum mean cross-validation error or the model exhibiting error within one standard error of the minimum.
Figure 7:
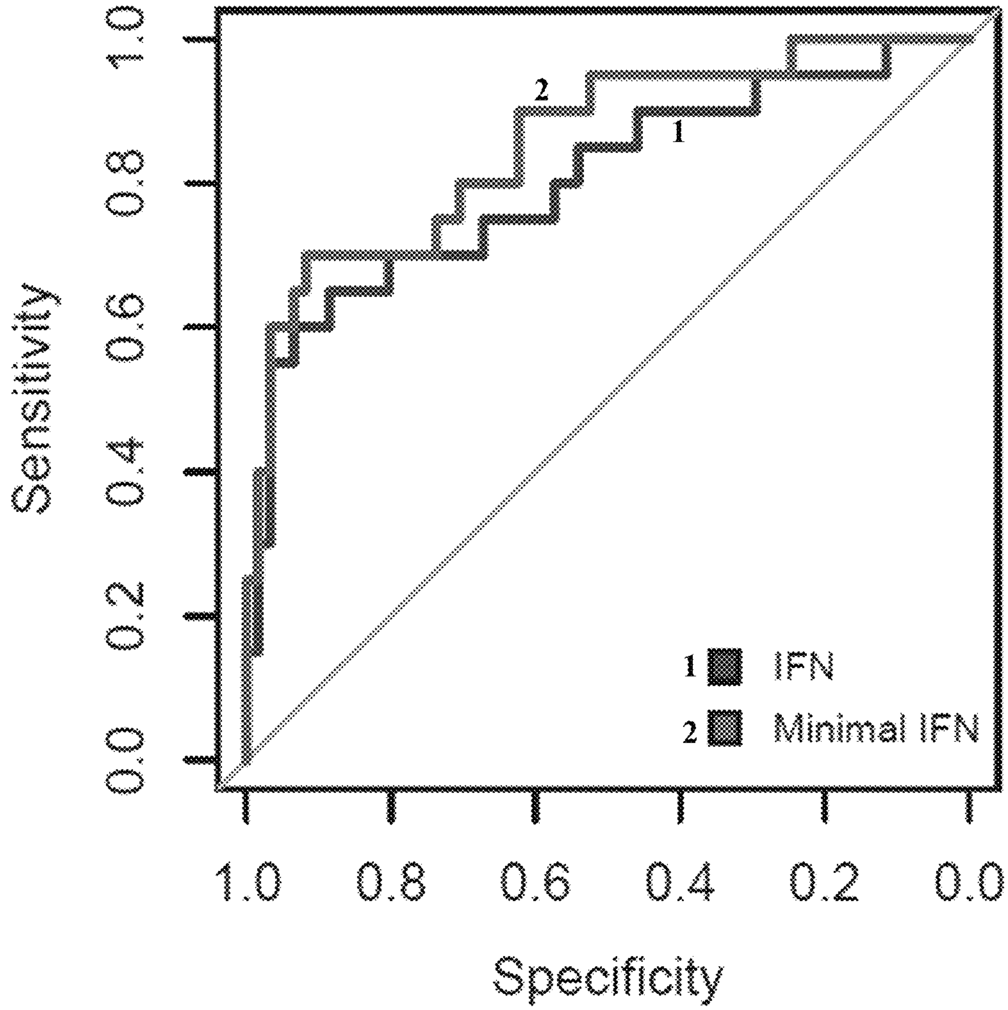
FIG. 7 is a plot representing a ROC showing that a minimal IFN signature performs as well as a complete IFN gene set (with 44 genes).
Figure 8:
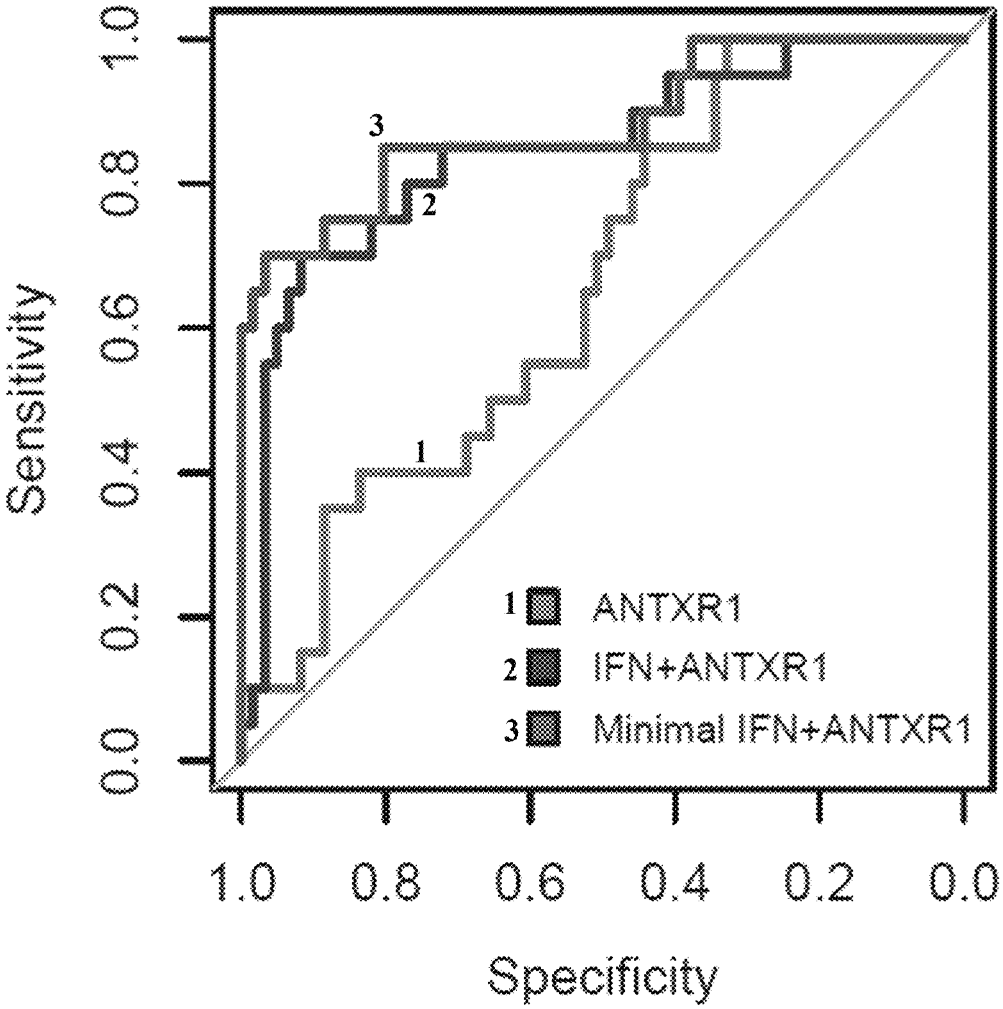
FIG. 8 is a plot representing a ROC showing that a minimal IFN signature (e.g. IFI35) performs as well as a complete IFN gene set. Receiver operating characteristic curves of minimal interferon signature or the complete IFN gene set were plotted. It was shown that a minimal IFN gene set performed similarly as the full IFN gene set based on Delong's method for comparison of two ROC curves. Sensitivity and specificity were optimal for IFN+ANTXR1 and minimal IFN+ANTXR1 as compared to ANTXR1 by itself.
Figure 9A:
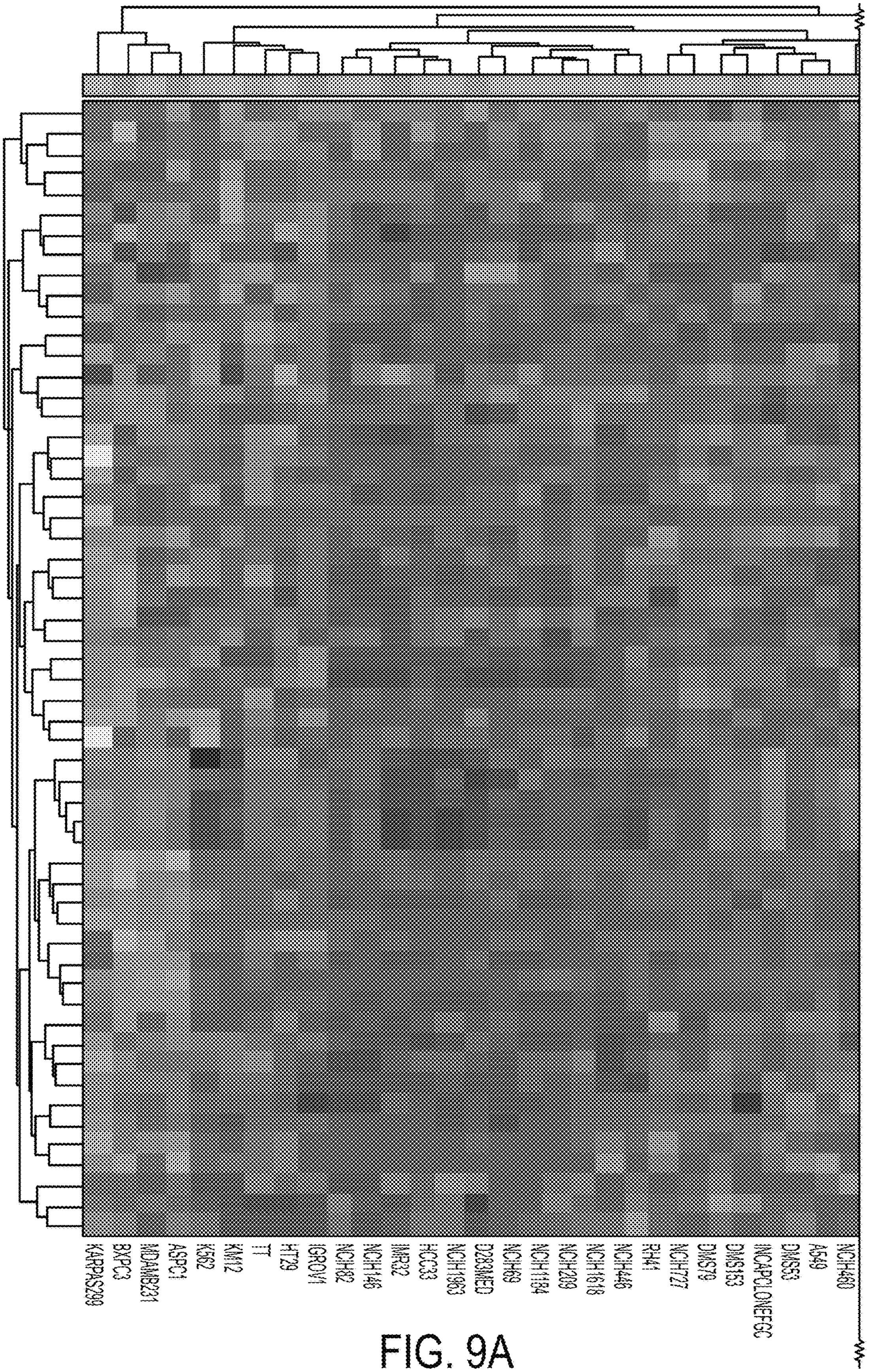
FIGS. 9A-9C depict a heatmap representing the IFN expression matrix for various IFN signature genes in various tumor samples (autonomic ganglia, bone, breast, central, haematopoietic, kidney, large intestine, liver, lung, oesophagus, ovary, pancreas, prostate, skin, soft tissue).
Figure 9B:
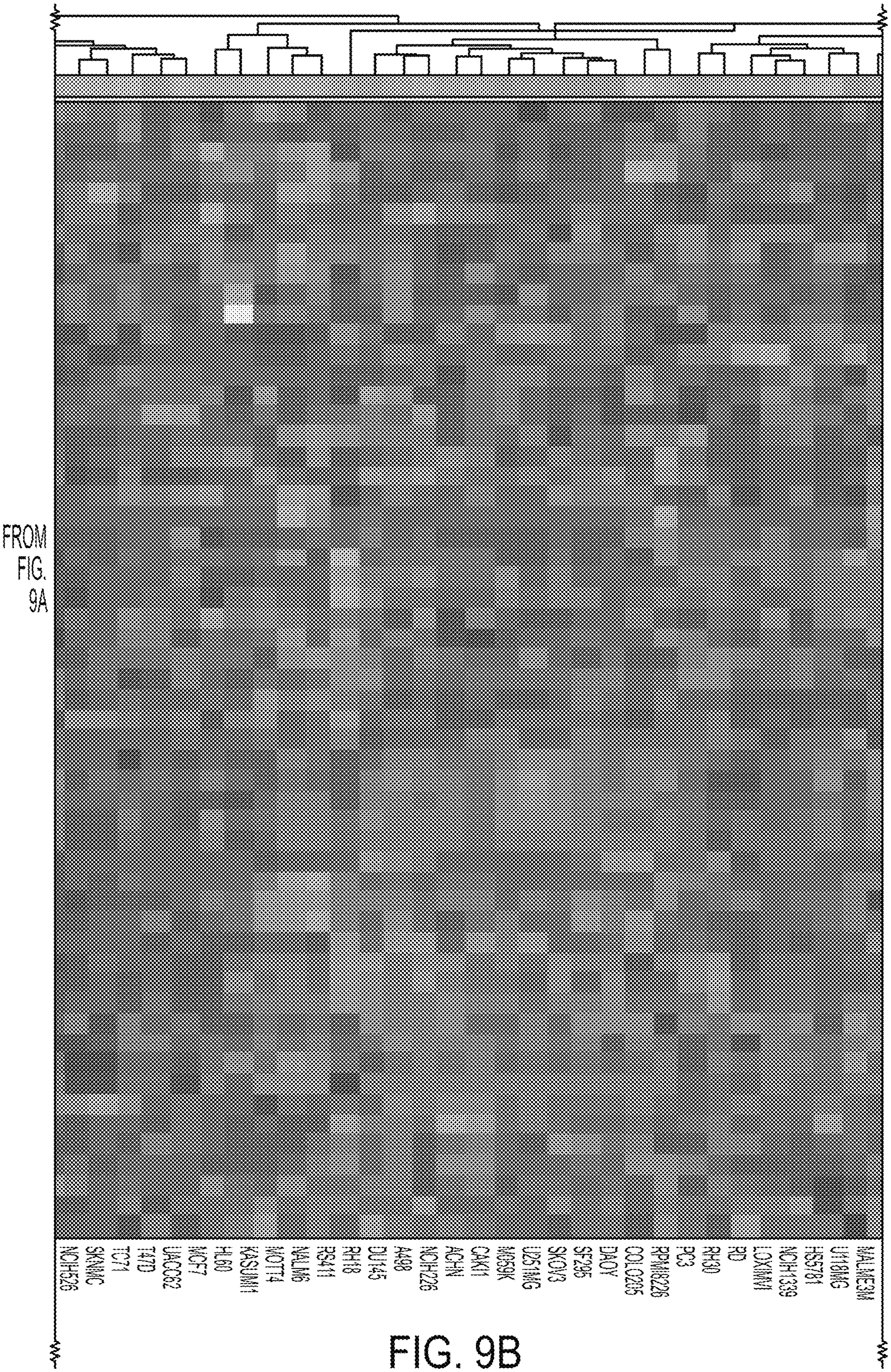
Figure 9C:
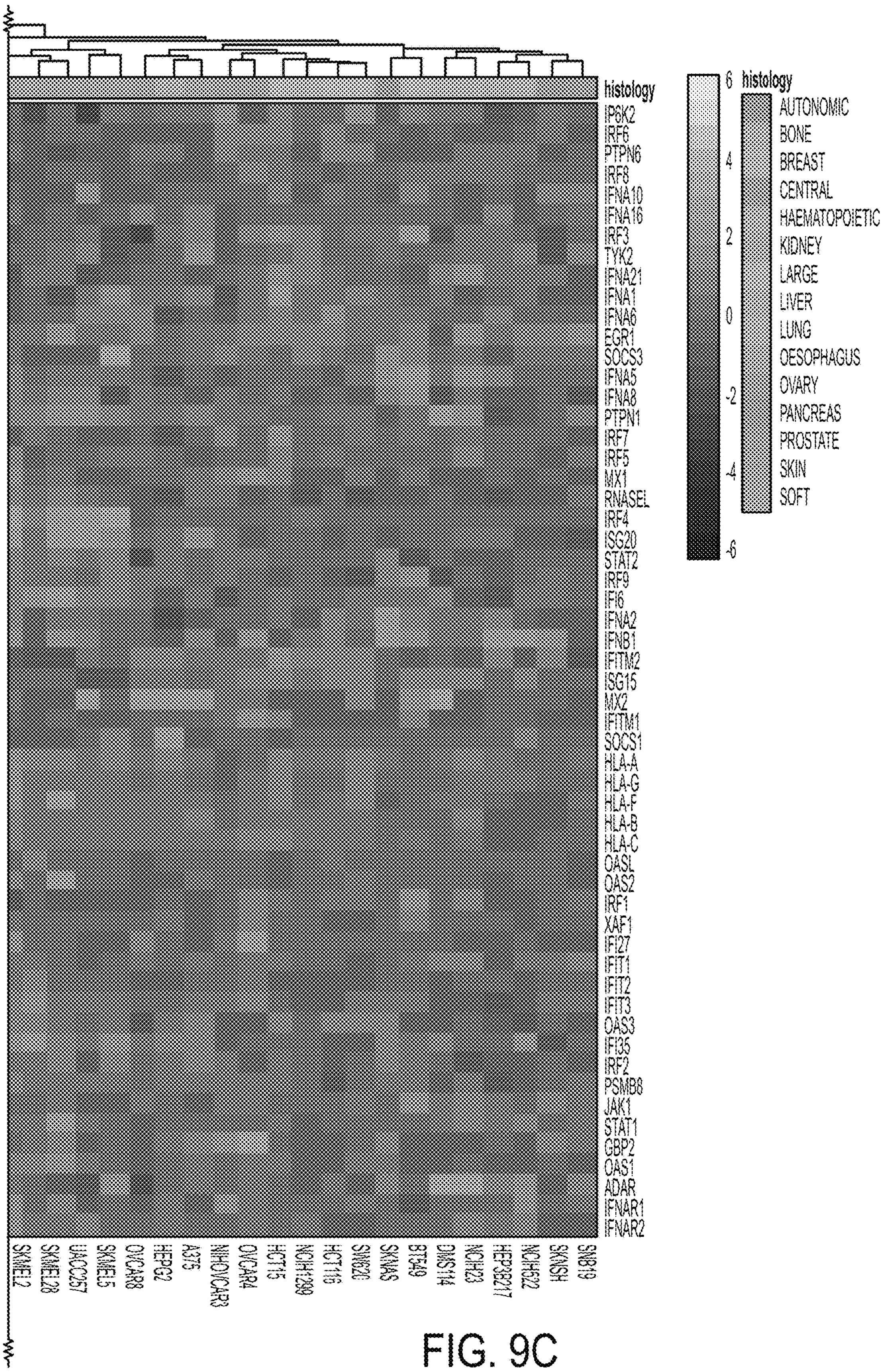
Figure 10:
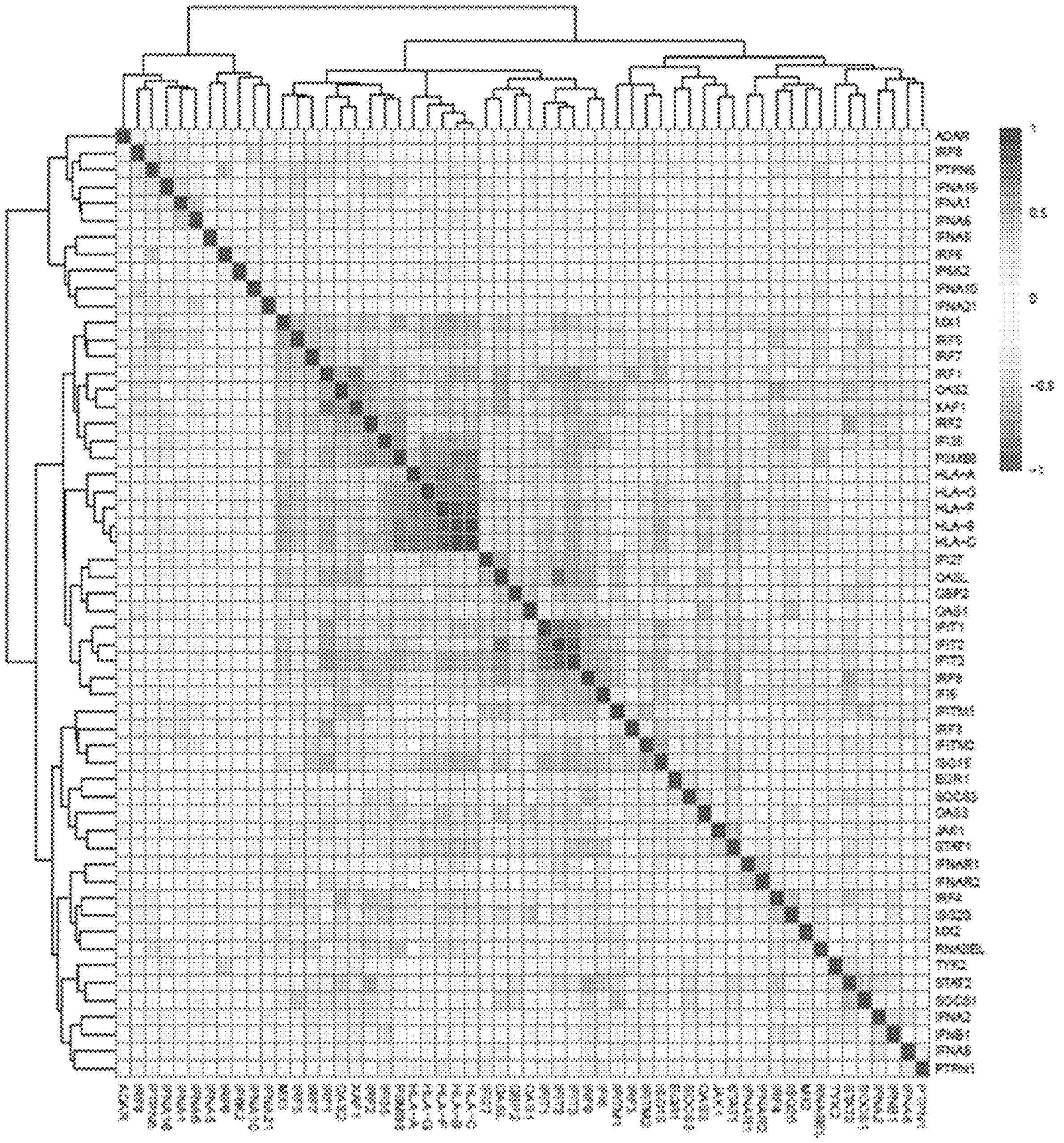
FIG. 10 is a heatmap representing the IFN correlation matrix for various IFN signature genes in various tumor samples (autonomic, bone, breast, central, haematopoietic, kidney, large intestine, liver, lung, oesophagus, ovary, pancreas, prostate, skin, soft tissue).
Figure 11:
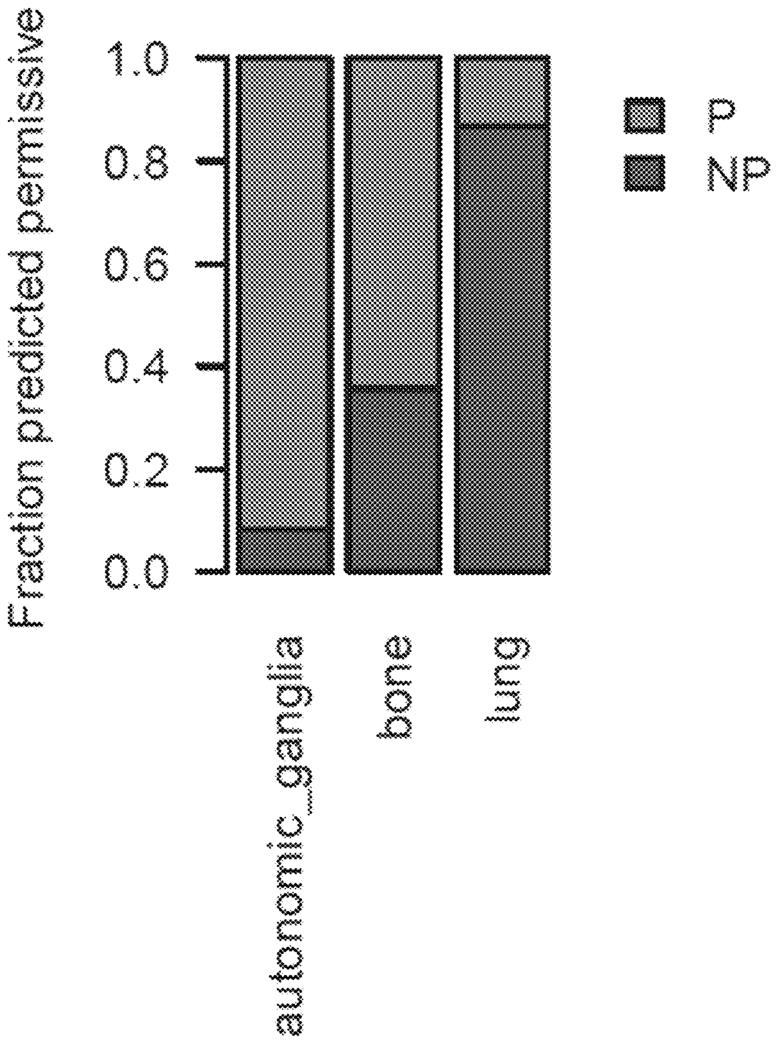
FIG. 11 is a bar graph illustrating the fractions of tumors (by Site: autonomic ganglia) that are predicted to be only permissive (P) versus non-permissive (NP).
Figure 12:
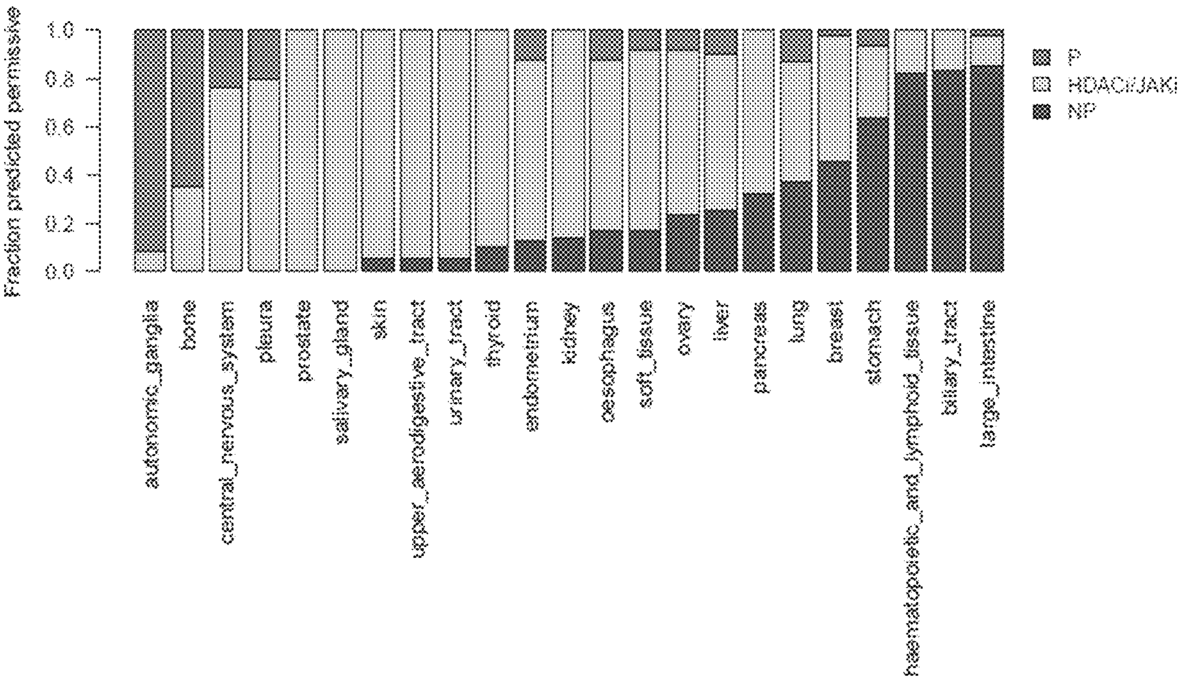
FIG. 12 is a bar graph showing that at least 65% of all solid cancer indications have ANTXR1/TEM 8 expressed a level necessary for SVV infection. 60-95% of major indications express TEM 8. 100% of all solid cancer indications have TEM 8 expressed at high levels in cancer stromal cells. P: Permissive; NP: Non-Permissive; and HDCAi/JAKi: Permissive upon treatment with HDCA and/or JAK inhibitors.
Figure 13:
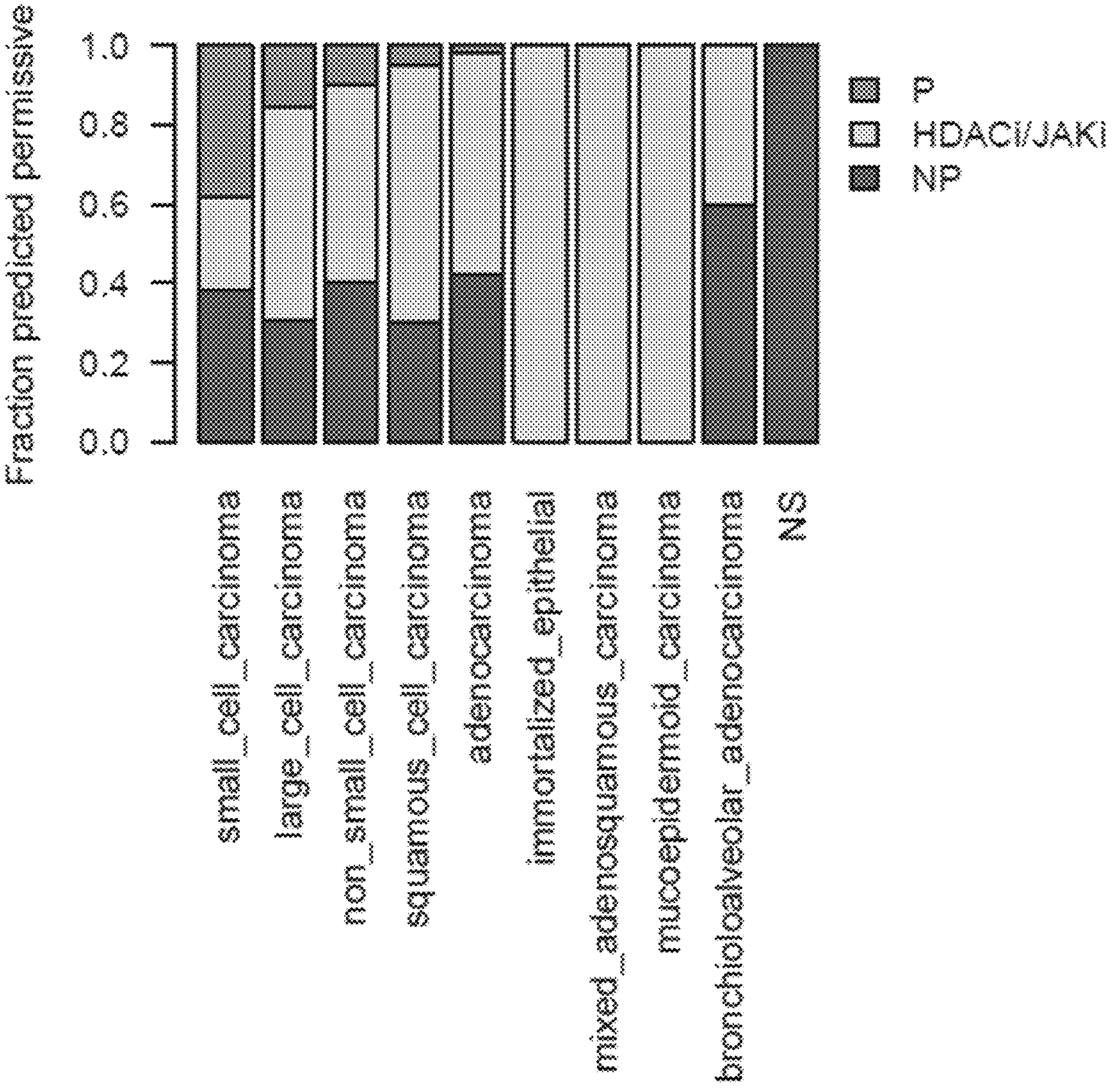
FIG. 13 is a bar graph illustrating the fractions of lung tumors that are predicted to be permissive. P: Permissive; NP: Non-Permissive; and HDCAi/JAKi: Permissive upon treatment with HDCA and/or JAK inhibitors.
Figure 14:
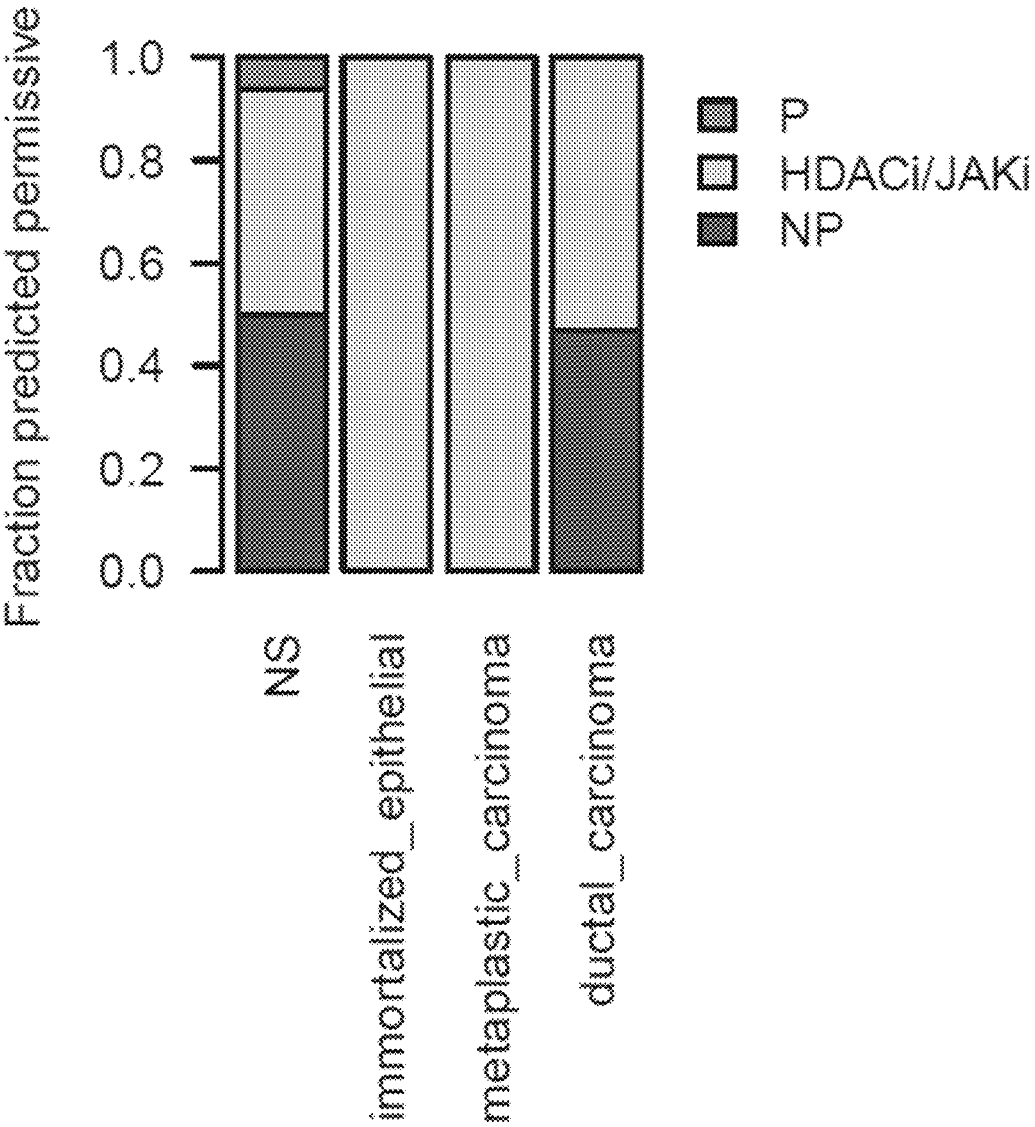
FIG. 14 is a bar graph illustrating the fractions of breast tumors that are predicted to be permissive. P: Permissive; NP: Non-Permissive; and HDCAi/JAKi: Permissive upon treatment with HDCA and/or JAK inhibitors.
Figure 15:
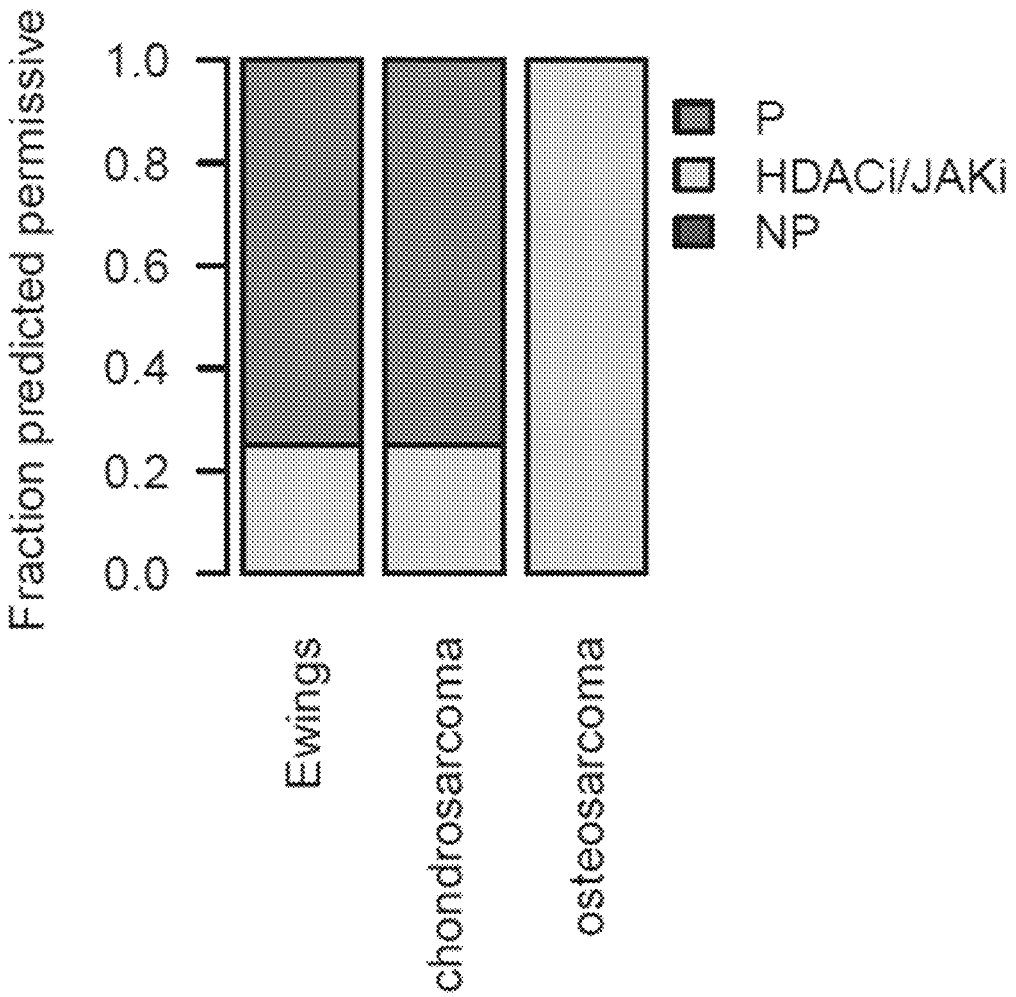
FIG. 15 is a bar graph illustrating the fractions of bone tumors that are predicted to be permissive. P: Permissive; NP: Non-Permissive; and HDCAi/JAKi: Permissive upon treatment with HDCA and/or JAK inhibitors.
Figure 16:
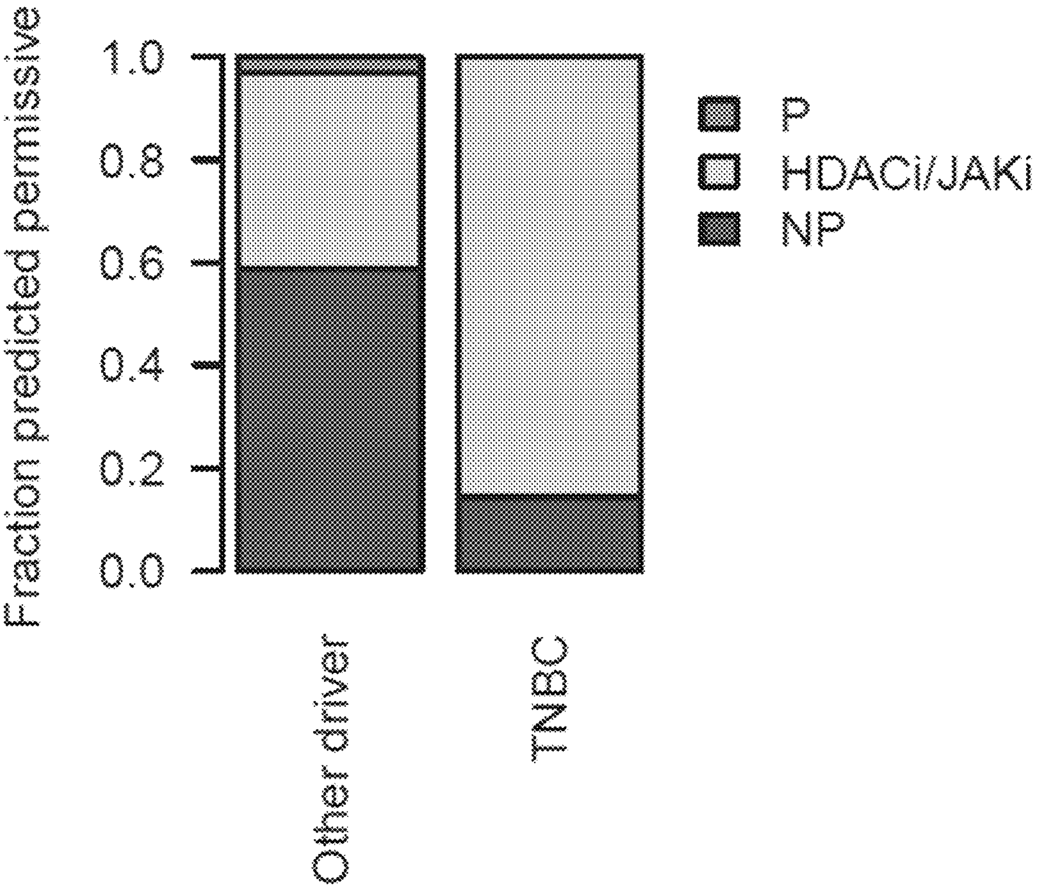
FIG. 16 is a bar plot illustrating the fractions of breast tumors that are predicted to be permissive (by driver). P: Permissive; NP: Non-Permissive; and HDCAi/JAKi: Permissive upon treatment with HDCA and/or JAK inhibitors.
Figure 17:
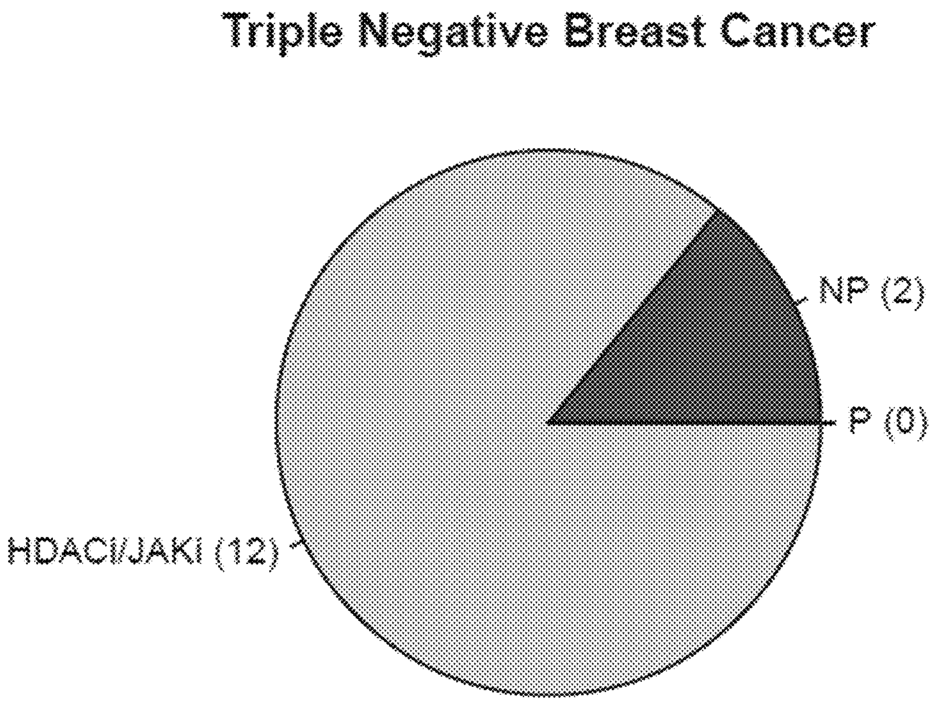
FIG. 17 is a graph illustrating the fractions of breast tumors that are predicted to be permissive (by driver). P: Permissive; NP: Non-Permissive; and HDCAi/JAKi: Permissive upon treatment with HDCA and/or JAK inhibitors.
Figure 18:
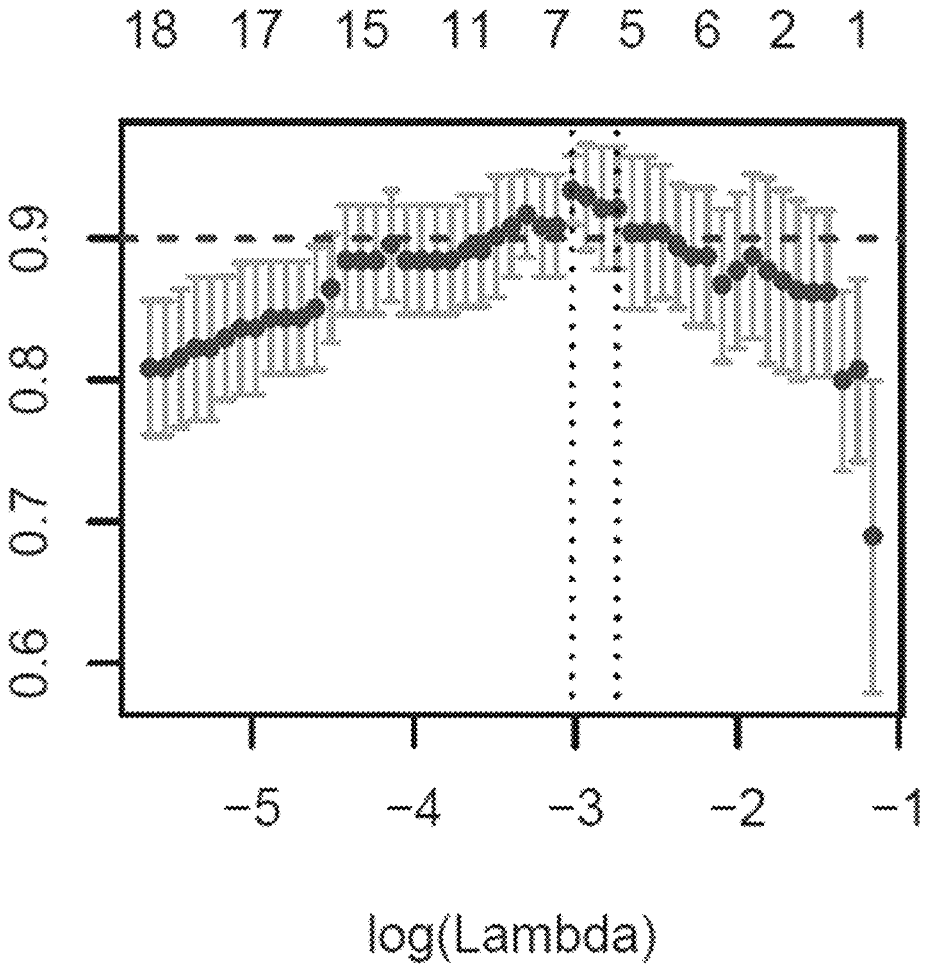
FIG. 18 is a graph representing the AUC minimization with a 0.9 cut off value for the predictive analysis.

Demonstrated herein is a very high correlation (~0.9) between the expression of these two factors above a specific threshold (FIG. 18) and permissivity and ability of SVV to efficiently replicate in the cell line. The model fit in FIG. 18 through 6-fold cross-validation was used to predict whether a given cell line in the entire set could be permissive based on a minimal interferon gene set using a tuning parameter, lambda, of 0.1.

Using computational analysis, ANTXR1/TEM 8 was shown to be above the specific threshold in over 60% of solid cancer cell lines in an extensive human cancer cell line database of over 700 cell lines (CCLE) and in the majority of lines in most major solid cancer indications including, but not limited to, triple negative breast cancer, ovarian cancer, NSCLC LC, SCC, adenocarcinoma, endometrial cancer, soft tissue sarcoma, head and neck cancer and bladder cancer. However, the majority of these cancer cell lines had a level of Type I INF gene(s) to predict that they would not be permissive to SVV infection. IFN-I expression, including the entire IFN-I pathway, was shown herein to be efficiently represented by few key biomarkers such as but not limited to biomarker gene IFI35. Other factors that can be relevant for assessing SVV infection and the efficacy of SVV treatment include, but are not limited to, genes involved in SVV cellular entry, uncoating, translation and replication (e.g. TEX2). The results of present analysis highlight the importance of reducing or eliminating, at least temporarily, IFN-I response to reach a sufficient level of replication of SVV to kill tumor cells by immunogenic cell death and activate an anti-tumor immune response.

Example 2: SVV Administration and Combination Therapy for Cancer Treatment

Contemplated herein is the treatment of patient's tumors in indications known to express above threshold levels of ANTXR1/TEM 8 by multiple intratumoral administration of SVV. This procedure can create a high ratio between the number of SVV infecting viruses and the number of host cancerous cells (high multiplicity of infection (MOI)) and a higher probability of sustained replication, activation of danger signals, immunogenic cells death and induction of an anti-tumor response. Multiple intravenous (IV) administrations at high doses utilizing agents that repress or eliminate the production of neutralizing antibodies can also be considered among others. Further, in order to ensure SVV efficiently replicates, agents known to inhibit, suppress or reduce (temporarily or permanently) IFN-I response can be used to maximize sufficient replication and induce immunogenic cell death and stimulate an anti-tumor immune response.

Combination of check point inhibitors (CPI) I, IFN-I inhibitors along with SVV may provide the optimal result for cancer treatment as this combination prevents an immune response from the host and favors SVV replication and killing of the cancerous tissue(s).

Figure 2:
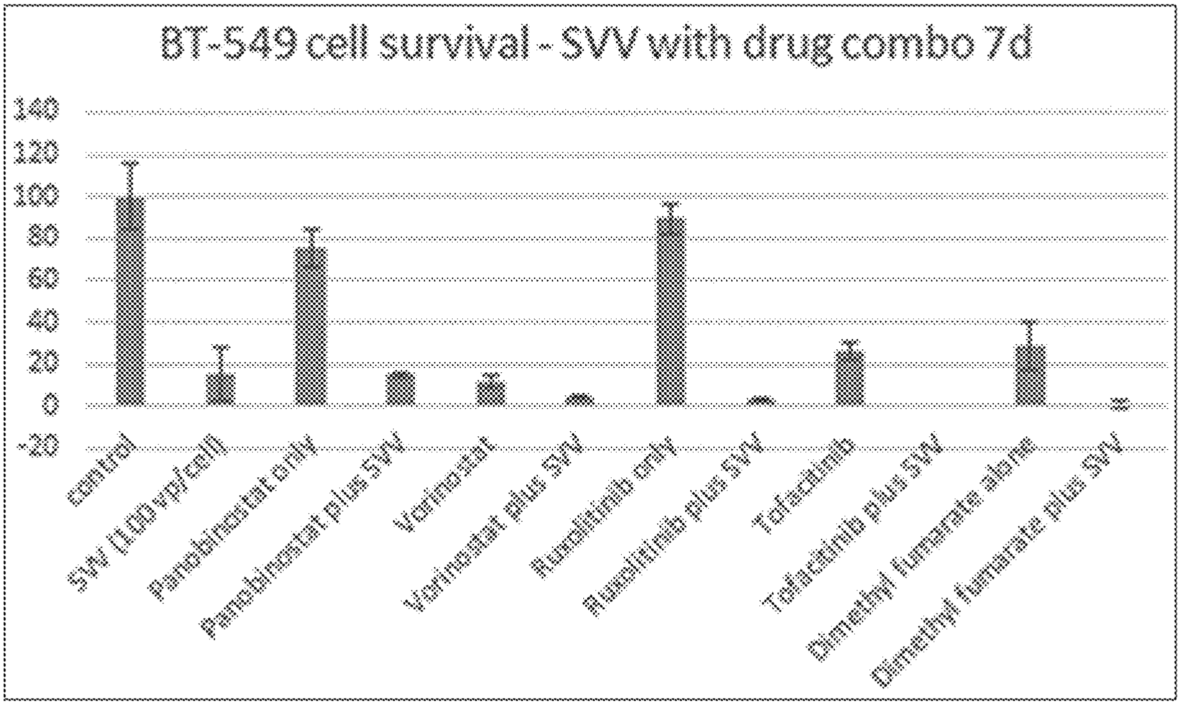
FIG. 2 is a histogram depicting an example of triple negative breast cancer cells (BT-549) that are susceptible to infection by Seneca Valley Virus. Treatment with various drug compounds showed a substantial enhancement of SVV replication in TNBC cell lines and cell death.
Figure 5:
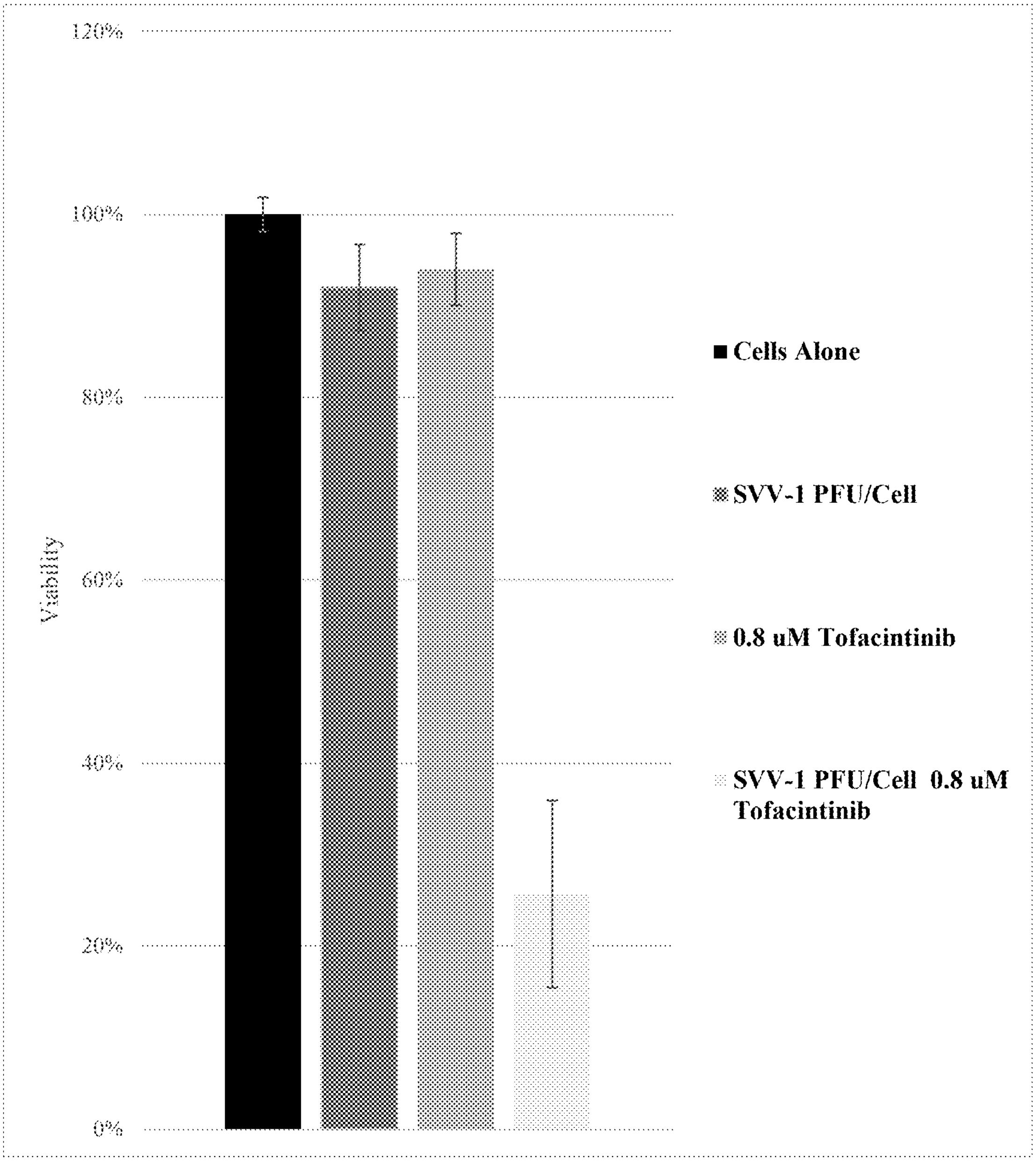
FIG. 5 is a histogram showing that the combination SVV and JAKi synergistically kills Triple Negative Breast Cancer (TNBC) lines. SVV is extremely selective toward killing only tumor cells even with inhibiting Type I IFN as the receptor ANTXR1/TEM 8 is extremely selective toward tumor cells. Treatment with Tofacintinib compound (1PFU/cell of SVV and 0.8 uM of Tofacintinib) showed a substantial enhancement of SVV replication in TNBC cell lines and cell death.

Example 3: Positive Effect of MAC Inhibitors and JAK Inhibitors for SVV Cancer Cells Infection and Killing In certain instances, infection with Seneca Valley Virus can be toxic to triple negative breast cancer cell lines. In these cases, it is necessary to reduce innate antiviral responses through the use of certain approved pharmaceutical compounds (see FIG. 1, FIG. 2 and FIG. 5). As shown in FIG. 1 and FIG. 5, the treatment of HTB-126 cells (triple negative breast cancer cell lines) with Tofacitinib modified and favored the susceptibility to virus mediated killing by SVV. As shown in FIG. 2, the treatment of BT-549 cells (triple negative breast cancer cell lines) with Tofacitinib or Vorinostat or Ruxolitinib modified and favored the susceptibility to virus mediated killing by SVV.

Figure 3:
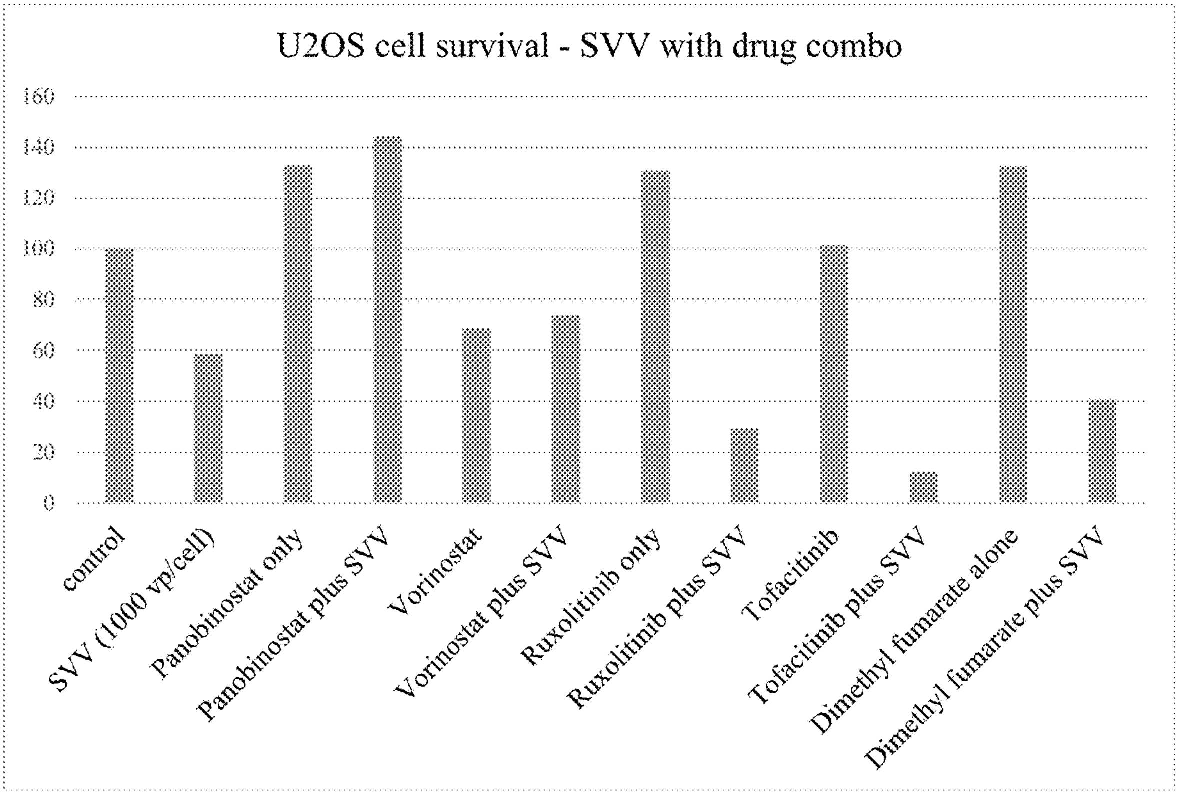
FIG. 3 is a histogram depicting an example of the use of a drug to modify susceptibility to virus mediated killing by Seneca Valley Virus (SVV). U2OS cells (osteosarcoma) were pretreated for 24 hours in pharmaceutical compounds to disrupt innate antiviral responses to allow increased viral mediated killing. Ruxolitinib, tofacitinib, and dimethyl fumarate increased Seneca Valley Virus mediated cell killing.

Osteosarcoma cell lines (U2OS) also showed augmented SVV mediated cell killing by similar compounds (e.g. Tofacitinib or Ruxolitinib) that increase cell killing in triple negative breast cancer cell lines (see FIG. 3).

Figure 4:
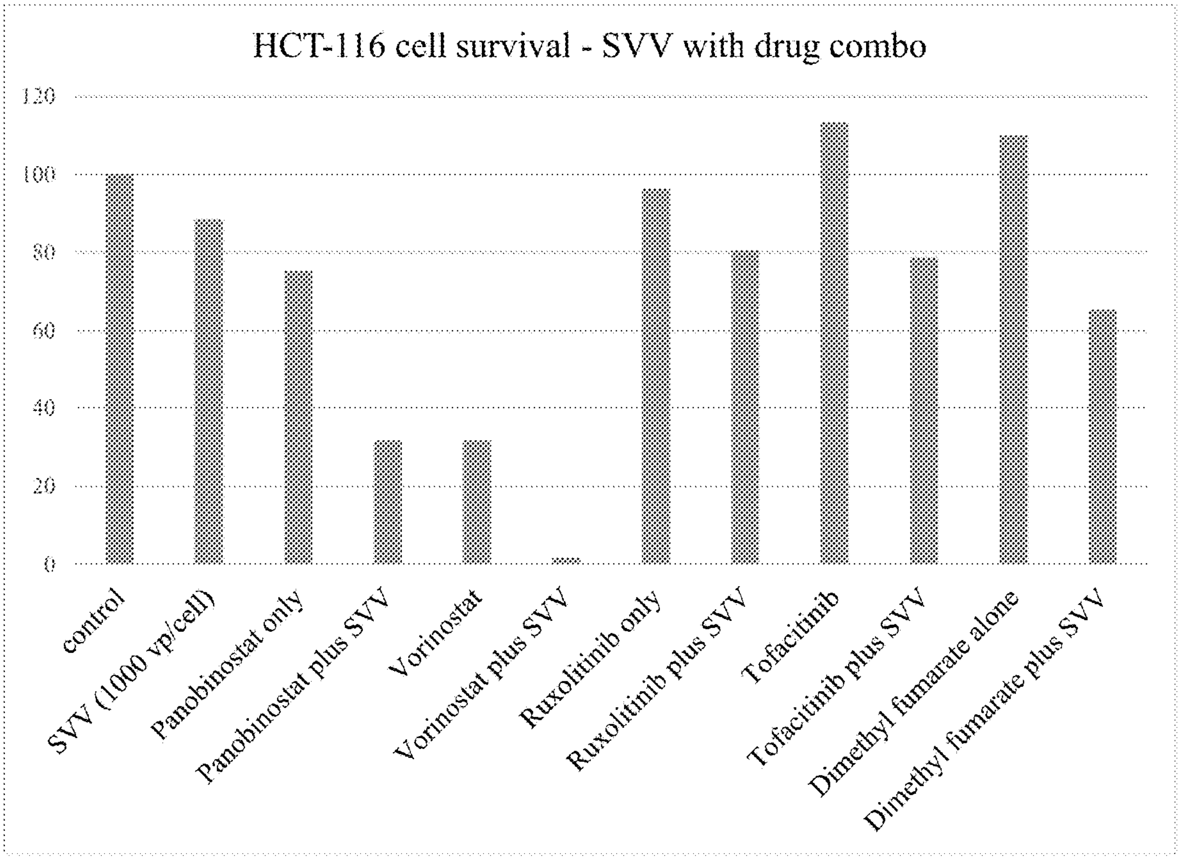
FIG. 4 is a histogram depicting an example of the use of a drug to modify susceptibility to virus mediated killing by Seneca Valley Virus (SVV). HCT-116 cells (Colorectal cancer cells) were pretreated for 24 hours in pharmaceutical compounds to disrupt innate antiviral responses to allow increased viral mediated killing. Panobinostat and vorinostat increased Seneca Valley Virus mediated cell killing with a smaller effect shown by tofacitnib and dimethyl fumarate.

The augmentation of SVV cell killing was also demonstrated in human colorectal cancer cell lines (HCT-116) but the increase in cell killing was mainly caused by MAC inhibitors (Panobinostat or Vorinostat) instead of the JAK inhibitors (Ruxolitinib, Tofacitinib or Dimethyl fumarate) which modified SVV's killing susceptibility in triple negative breast cancer and osteosarcoma cell lines (see FIG. 4).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of increasing Seneca Valley Virus (SVV) or SVV derivative replication in a cancer cell non-permissive to SWV or SVV derivative replication, the method comprising contacting the cancer cell with a JAK inhibitor and an effective amount of SVV or SVV derivative, wherein the cancer cell is characterized by an expression level of ANTXR1 higher than an ANTXR1 reference value and is non-permissive of the SVV or the SVV derivative replication, the JAK inhibitor reduces the expression level of IFN-I in the cancer cell, and the replication of the SWV or the SVV derivative in the cancer cell is increased to a level of replication in an SVV permissive cell not contacted with the JAK inhibitor.

2. The method of claim 1, wherein the JAK inhibitor is selected from ruxolitinib, tofacitinib, dimethyl fumarate, or a combination of any thereof.

3. The method of claim 1, wherein the cancer cell is contacted with the JAK inhibitor formerly, simultaneously or subsequently to contacting the cancer cell with the SVV.

4. The method of claim 1, wherein:

(a) the expression level of ANTXR1 is determined based on the level of an ANTXR1 mRNA or an ANTXR1 protein; and/or (b) the expression level of IFN-I is determined based on the level of an IFN-I biomarker mRNA or an IFN-I biomarker protein.

5. The method of claim 4, wherein the IFN-I biomarker mRNA or IFN-I biomarker protein is at least one mRNA or protein selected from the group consisting of IFI35, IFN-α, IFN-β, IFN-κ, IFN-δ, IFN-ε, IFN-τ, IFN-ω, and IFN-ζ, ADAR, IRF9, IFITM3, IFITM2, USP18, LOC144383, EGR1, IFI6, GBP2, HLA-A, HLA-B, HLA-C, HLA-F, HLA-G, IRF8, IFI27, IFI35, IFIT2, IFIT1, IFIT3, IFNA1, IFNA2, IFNA4, IFNA5, IFNA6, IFNA7, IFNA8, IFNA10, IFNA14, IFNA16, IFNA17, IFNA21, IFNAR1, IFNAR2, IFNB1, IRF1, IRF2, IRF3, IRF4, IRF5, IRF6, IRF7, ISG20, JAK1, MX1, MX2, OAS1, OAS2, OAS3, IP6K2, XAF1, PSMB8, PTPN1, PTPN6, RNASEL, HLA-K, STAT1, STAT2, TYK2, HLA-B, IFITM1, OASL, SOCS1, SOCS3 and ISG15.

6. The method of claim 1, wherein the cancer cell comprises a triple negative breast cancer cell, a small cell lung cancer cell, a non-small cell lung cancer cell, a non-small cell squamous carcinoma cell, an adenocarcinoma cell, a glioblastoma cell, a skin cancer cell, a hepatocellular carcinoma cell, a colon cancer cell, a cervical cancer cell, an ovarian cancer cell, an endometrial cancer cell, a neuroendocrine cancer cell, a pancreatic cancer cell, a thyroid cancer cell, a kidney cancer cell, a bone cancer cell, an esophagus cancer cell, or a soft tissue cancer cell.

* * * * *